US011420922B2

(12) United States Patent
Tavis et al.

(10) Patent No.: US 11,420,922 B2
(45) Date of Patent: Aug. 23, 2022

(54) HYDROXYLATED TROPOLONE INHIBITORS OF NUCLEOTIDYL TRANSFERASES IN HERPESVIRUS AND HEPATITIS B AND USES THEREFOR

(71) Applicants: Saint Louis University, St Louis, MO (US); Research Foundation of the City University of New York, New York, NY (US)

(72) Inventors: John Edwin Tavis, Kirkwood, MO (US); Lynda Anne Morrison, Webster Groves, MO (US); Ryan P. Murelli, Belleville, NJ (US)

(73) Assignees: Saint Louis University, St. Louis, MO (US); Research Foundation of the City University of New York, New York, NY (US)

( * ) Notice: Subject to any disclaimer, the term of this patent is extended or adjusted under 35 U.S.C. 154(b) by 0 days.

(21) Appl. No.: 15/735,195

(22) PCT Filed: Jun. 10, 2016

(86) PCT No.: PCT/US2016/036914
§ 371 (c)(1),
(2) Date: Dec. 10, 2017

(87) PCT Pub. No.: WO2016/201243
PCT Pub. Date: Dec. 15, 2016

(65) Prior Publication Data
US 2018/0297924 A1 Oct. 18, 2018

Related U.S. Application Data

(60) Provisional application No. 62/309,266, filed on Mar. 16, 2016, provisional application No. 62/174,350, filed on Jun. 11, 2015.

(51) Int. Cl.

| | | |
|---|---|---|
| *A61K 31/675* | (2006.01) | |
| *A61K 31/122* | (2006.01) | |
| *A61K 31/7072* | (2006.01) | |
| *A61K 31/522* | (2006.01) | |
| *A61K 31/708* | (2006.01) | |
| *A61K 31/513* | (2006.01) | |
| *A61K 45/06* | (2006.01) | |
| *A61K 9/00* | (2006.01) | |
| *A61P 31/22* | (2006.01) | |
| *C07C 49/733* | (2006.01) | |
| *C07C 69/757* | (2006.01) | |
| *C07C 49/717* | (2006.01) | |
| *A61K 38/21* | (2006.01) | |

(52) U.S. Cl.
CPC .......... *C07C 49/717* (2013.01); *A61K 9/0048* (2013.01); *A61K 31/122* (2013.01); *A61K 31/513* (2013.01); *A61K 31/522* (2013.01); *A61K 31/675* (2013.01); *A61K 31/708* (2013.01); *A61K 31/7072* (2013.01); *A61K 38/212* (2013.01); *A61K 45/06* (2013.01); *A61P 31/22* (2018.01); *C07C 49/733* (2013.01); *C07C 69/757* (2013.01); *C07C 2601/14* (2017.05); *C07C 2601/18* (2017.05)

(58) Field of Classification Search
CPC ................ A61K 31/675; A61K 31/122; A61K 31/7072; A61K 31/522; A61K 31/708; A61K 31/513; A61K 31/22; A61K 45/06; A61K 9/0048; A61K 9/00; A61K 38/212; A61K 2300/00; C07C 49/733; C07C 49/717; C07C 69/757; C07C 2601/14; C07C 2601/18; A61P 31/22
See application file for complete search history.

(56) References Cited

U.S. PATENT DOCUMENTS

| 4,950,686 A | 8/1990 | Kondo et al. |
|---|---|---|
| 2007/0054967 A1 | 3/2007 | Schmaus et al. |
| 2010/0152301 A1 | 6/2010 | Pommier et al. |
| 2014/0249181 A1 | 9/2014 | Beutler et al. |

FOREIGN PATENT DOCUMENTS

WO WO 2013-192554 12/2013

OTHER PUBLICATIONS

Lu et al.—abstract, 2015, caplus an 2015:226906.*
Lu et al., 2015, Antimicrobial Agents and Chemotherapy, 59(2), 1070-1079.*
Lu et al., 2015, supplemental material for Antimicrobial Agents and Chemotherapy, 59(2), 1070-1079, Figure 1S.*
RN4356-35-8, registry database compound, (1984).*
RN4356-35-8-pubchem,(2005), pubchem record for compound RN4356-35-8.*
RN1414861-14-5, registry database compound, entry date Dec. 14, 2012.*
Hirsch et al., Bioorganic and Medicinal Chemistry Letters, 2014, 24, 4943-4947.*
Meek et al., 2012, caplus an 2012:1695748.*
Hirsch et al. 2, 2014, caplus an 2014:1631625.*
RN1803246-34-5, Sep. 3, 2015, registry database compound.*
Masaoka et al., 2016, Biochemistry, 55, 809-819.*
Extended European Search Report issued in European Application No. 16808385.5, dated Jan. 14, 2019.
Meek et al., "An oxidopyrylium eyelization/ring-opening route to polysubstituted α-hydroxytropolones," *Organic Letters*, 14(23):5988-5991, 2012.

(Continued)

*Primary Examiner* — Sun Jae Yoo
(74) *Attorney, Agent, or Firm* — Parker Highlander PLLC

(57) ABSTRACT

The present disclosure relates to inhibitors of herpesvirus nucleic acid metabolism and inhibitors of Hepatitis B virus. Also provided are methods of treatment using these agents.

14 Claims, 7 Drawing Sheets
Specification includes a Sequence Listing.

(56) References Cited

OTHER PUBLICATIONS

Williams et al., "Triflic acid-mediated rearrangements of 3-methoxy-8-oxabicyclo[3.2.1]octa-3,6-dien-2-ones: synthesis of methoxytropolones and furans," *Journal of Organic Chemistry*, 78(23):11707-11713, 2013.
Alba et al., "Genomewide Function Conservation and Phylogeny in the Herpesviridae," *Genome Res.*, 11:43-54, 2001.
Ariyoshi et al., "*Atomic structure of the RuvC resolvase: a Holliday junction-specific endonuclease from E. coli*," *Cell*, 78:1063-1072, 1994.
Billamboz et al., "Magnesium Chelating 2-Hydroxyisoquinoline-1,3(2H,4H)-diones, as Inhibitors of HIV-1 Integrase and/or the HIV-1 Reverse Transcriptase Ribonuclease H Domain: Discovery of a Novel Selective Inhibitor of the Ribonuclease H Function," *J. Med. Chem.*, 54:1812-1824, 2011.
Bogner et al., "The gene product of human cytomegalovirus open reading frame UL56 binds the pac motif and has specific nuclease activity,"*J. Virol.*, 72:2259-2264, 1998.
Bogner, "Human cytomegalovirus terminase as a target for antiviral chemotherapy," *Rev. Med. Virol.*, 12:115-127, 2002.
Bokesch et al., "IV-1 Ribonuclease H Inhibitory Phenolic Glycosides from *Eugenia hyemalis*," *J. Nat. Prod.* 71, 1634-1636, 2008.
Bortner et al., "Herpes simplex virus 1 single-strand DNA-binding protein (ICP8) will promote homologous pairing and strand transfer," *J. Mol. Biol.*, 231:241-250, 1993.
Budihas et al., "Selective inhibition of HIV-1 reverse transcriptase-associated ribonuclease H activity by hydroxylated tropolones," *Nucleic Acids Res.*, 33:1249-1256, 2005.
Cai et al., "Hepatitis B virus replication is blocked by a 2-hydroxyisoquinoline-1, 3 (2H, 4H)-dione (HID) inhibitor of the viral ribonuclease H activity," *Antiviral Res.*, 108:48-55, 2014.
Chen et al., "The relationship of herpes simplex virus latency associated transcript expression to genome copy number: a quantitative study using laser capture microdissection," *J. Neurovirol.*, 8:204-210, 2002.
Chung et al., "Structure-activity analysis of vinylogons urea inhibitors of human immunodeficiency virus-encoded ribonuclease H," *Antimicrob. Agents Chemother.*, 54, 3913-3921, 2010.
Chung et al., "Synthesis, activity, and structural analysis of novel α-hydroxytropolone inhibitors of human immunodeficiency virus reverse transcriptase-associated ribonuclease H," *J. Med. Chem.*, 54, 4462-4473, 2011.
Coen, "Viral DNA polymerases," In: *DNA Replication in Eukaryotic Cells*, 495-523, 1996.
Didierjean et al., "Inhibition of human immunodeficiency virus type 1 reverse transcriptase, RNase H, and integrase activities by hydroxytropolones," *Antimicrob. Agents Chemother.*, 49, 4884-4894, 2005.
Dyda et al., "Crystal structure of the catalytic domain of HIV-1 integrase: similarity to other polynucleotidyltransferases," *Science*, 266:1981-1986, 1994.
Frank et al., "Cloning of the cDNA encoding the large subunit of human RNase HI, a homologue of the prokaryotic RNase HII," *Proc. Natl. Acad. Sci. USA*, 95:12872-12877, 1998.
Frank et al., "Cloning, subcellular localization and functional expression of human RNase HII," *Biol. Chem.*, 379:1407-1412, 1998.
Freed and Martin, "HIVs and their replication," In: *Fields Virology*, Knipe, D.M., Howley, P.M., Griffin, D.E., Lamb, R.A., Martin, M.A., Roizman, B., Straus, S.E. (Eds.), Lippincott Williams & Wilkins, Philadelphia, pp. 2107-2185, 2007.
Fuji et al., "Derivatives of 5-nitro-furan-2-carboxylic acid carbamoylmethyl ester inhibit RNase H activity associated with HIV-1 reverse transcriptase," *J. Med. Chem.*, 52, 1380-1387, 2009.
Gao et al., "Functional conservations of the alkaline nuclease of herpes simplex type 1 and human cytomegalovirus," *Virology*, 249:460-470, 1998.
Goedken et al., "Co-crystal of *Escherichia coli* RNase HI with Mn2+ Ions Reveals Two Divalent Metals Bound in the Active Site," *J. Biol. Chem.*, 276:7266-7271, 2001.
Grandi et al., "Small molecule inhibitors of HIV RT Ribonuclease H," *Bioorg. Med. Chem. Lett.* 20, 398-402, 2010.
Himmel et al., "HIV-1 reverse transcriptase structure with RNase H inhibitor dihydroxy benzoyl naphthyl hydrazone bound at a novel site," *ACS Chem. Biol.*, 1:702-712, 2006.
Himmel et al., "Structure of HIV-1 reverse transcriptase with the inhibitor β-thujaplicinol bound at the RNase H active site," *Structure*, 17:1625-1635, 2009.
Hostomsky et al., "Ribonuclease H," In: *Nucleases*, Linn, S.M., Lloyd, R.S., Roberts, R.J. (Eds.), Cold Spring Harbor Laboratory Press, Plainview, NY, pp. 341-376, 1993.
Hu et al., "β-Thujaplicinol inhibits hepatitis B virus replication by blocking the viral ribonuclease H activity," *Antiviral Res.*, 99:221-229, 2013.
Hwang and Bogner, "ATPase activity of the temunase subunit pUL56 of human cytomegalovirus," *J. Biol. Chem.*, 277:6943-6948, 2002.
International Preliminary Report on Patentability issued in corresponding PCT Application No. PCT/US2016/036914, dated Dec. 21, 2017.
International Search Report and Written Opinion issued in corresponding PCT Application No. PCT/US2016/036914, dated Sep. 7, 2016.
Ireland et al., "Synthetic α-hydroxytropolones inhibit replication of wild-type and acyclovir-resistant herpes simplex viruses," *Antimicrob. Agents Chemother.*, 60(4):2140-2149, 2016.
Katayanagi et al., "Three-dimensional structure of ribonuclease H from *E. coli*," *Nature*, 347: 306-309, 1990.
Keck et al., "Activation/Attenuation Model for RNase H: A One-Metal Mechanism with Second-Metal Inhibition," *J. Biol. Chem.*, 273, 34128-34133, 1998.
Kirschberg et al., "RNase H active site inhibitors of human immunodeficiency virus type 1 reverse transcriptase: design, biochemical activity, and structural information," *J. Med. Chem.*, 52:5781-5784, 2009.
Klarmann et al., "Uncovering the complexities of retroviral ribonuclease H reveals its potential as a therapeutic target," *AIDS Rev.*, 4:183-194, 2002.
Klumpp and Mirzadegan, "Recent progress in the design of small molecule inhibitors of HIV RNase H," *Curr. Pharm. Des* 12:1909-1922, 2006.
Klumpp et al., "Two-metal ion mechanism of RNA cleavage by HIV RNase H and mechanism-based design of selective HIV RNase H inhibitors," *Nucleic Acids Res.*, 31(23):6852-6859, 2003.
Lai et al., "Crystal structure of archaeal RNase HII: a homologue of human major RNase H," *Structure*, 8:897-904, 2000.
Lima et al., "Human RNases H,"*Methods Enzymol.* 341:430-440, 2001.
Liu et al., "Crystal structure of the herpes simplex virus 1 DNA polymerase," *J. Biol. Chem.*, 281:18193-18200, 2006.
Longnecker et al., "Epstein-Barr Virus," In: *Fields Virology*, 6th ed., 1898-1959, 2013.
Lu et al., "Hydroxylated Tropolones Inhibit Hepatitis B Virus Replication by Blocking Viral Ribonuclease H Activity," *Antimicrob. Agents Chemother.*, 59(2):1070-1079, 2015.
Lu et al., "Supplemental Material: Hydroxylated Tropolones Inhibit Hepatitis B Virus Replication by Blocking Viral Ribonuclease H Activity," *Antimicrob. Agents Chemother.*, 1-2, 2015.
Masaoka, et al., "Characterization of the C-terminal nuclease domain of herpes simplex virus pUL15 as a target of nucleotidyltransferase inhibitors," *Biochem.*, 55(5):809-819, 2016.
Mettenleiter et al., "Herpesvirus assembly: an update," *Virus Res.*, 143:222-234, 2009.
Mohni et al., "DNA mismatch repair proteins are required for efficient herpes simplex vims type I replication," *J. Virol.*, 85:12241-12253, 2011.
Nimonkar and Boehmer, "The herpes simplex virus type-1 single-strand DNA-binding protein (ICP8) promotes strand invasion," *J Biol Chem.*, 278:9678-9682, 2003.

(56) References Cited

OTHER PUBLICATIONS

Nowotny et al., "Crystal structures of RNase H bound to an RNA/DNA hybrid: substrate specificity and metal-dependent catalysis," *Cell*, 121:1005-1016, 2005.
Nowotny, "Retroviral integrase superfamily: the structural perspective," *EMBO Rep.*, 10:144-151, 2009.
Parker et al., "Crystal structure of a PIWI protein suggests mechanisms for siRNA recognition and slicer activity," *EMBO J.*, 23:4727-4737, 2004.
PubChem-CID Database Entry: 73055489, Mar. 10, 2014.
PubChem-SID Database Entry: 275526085, Dec. 25, 2015.
PubChem-SID Database Entry: 7437574, Sep. 18, 2005.
Scheffczik et al., "The terminase subunits pUL56 and pUL89 of human cytomegalovirus are DNA-metabolizing proteins with toroidal structure," *Nucleic Acids Res.*, 30:1695-1703, 2002.
Scholz et al., "Identification of the ATP-binding site in the terminase subunit pUL56 of human cytomegalovirus," *Nucleic Acids Res.*, 31:1426-1433, 2003.
Schumacher et al., "The HSV-1 exonuclease, UL12, stimulates recombination by a single strand annealing mechanism," *PLoS Pathog.*, 8:e1002862, 2012.
Shaw-Reid et al., "Inhibition of HIV-1 ribonuclease H by a novel diketo acid, 4-[5-(benzoylamino) thien-2-yl]-2,4-dioxobutanoic acid," *J. Biol. Chem.*, 278, 2777-2780, 2003.
Song et al., "Crystal structure of Argonaute and its implications for RISC slicer activity," *Science*, 305:1434-1437, 2004.
Su et al., "Structural basis for the inhibition of RNase H activity of HIV-1 reverse transcriptase by RNase H active site-directed inhibitors," *J. Virol.*, 84:7625-7633, 2010.
Takada et al., "An HIV RNase H Inhibitory 1,3,4,5-Tetragalloylapiitol from the African Plant *Hylodendron gabunensis*," *J. Nat. Prod.* 70, 1647-1649, 2007.
Tavis et al., "The hepatitis B virus ribonuclease H is sensitive to inhibitors of the human immunodeficiency virus ribonuclease H and integrase enzymes," *PLoS Pathog.*, 9:e1003125, 2013.
Wang et al., "Laser-Capture Microdissection: Refining Estimates of the Quantity and Distribution of Latent Herpes Simplex Virus 1 and Varicella-Zoster Virus DNA in Human Trigeminal Ganglia at the Single-Cell Level," *J. Virol.*, 79:14079-14087, 2005.
Weizman and Weller, "Interactions between HSV-1 and the DNA damage response," In: *Alphaherpesviruses: Molecular Virology*, 257-268, 2011.
Weller and Coen, "Herpes simplex viruses: mechanisms of DNA replication," *Cold Spring Harbor Perspect. Biol.*, 4:a013011, 2012.
Wendeler et al., "Vinylogous ureas as a novel class of inhibitors of reverse transcriptase-associated ribonuclease H activity," *ACS Chem. Biol.*, 3:635-644, 2008.
Williams et al., "Potent and selective HIV-1 ribonuclease H inhibitors based on a 1-hydroxy-1, 8-naphthyridin-2 (IH)-one scaffold," *Bioorg. Med. Chem. Lett.*, 20:6754-6757, 2010.
Yang and Steitz, "Recombining the structures of HIV integrase, RuvC and RNase H," *Structure*, 3:131-134, 1995.
Yang et al., "Structure of ribonuclease H phased at 2 A resolution by MAD analysis of the selenomethionyl protein," *Science*, 249:1398-1405, 1990.
Zhu et al., "Processing of lagging-strand intermediates in vitro by herpes simplex virus type 1 DNA polymerase," *J. Virol.*, 84:7459-7472, 2010.

* cited by examiner

HYDROXYLATED TROPOLONE INHIBITORS OF NUCLEOTIDYL TRANSFERASES IN HERPESVIRUS AND HEPATITIS B AND USES THEREFOR

The present application is a national phase application under 35 U.S.C. § 371 of International Application No. PCT/US2016/036914, filed Jun. 10, 2016, which claims benefit of priority to U.S. Provisional Application Ser. No. 62/174,350, filed Jun. 11, 2015, and U.S. Provisional Application Ser. No. 62/309,266, filed Mar. 16, 2016, the entire contents of each of which are hereby incorporated by reference.

The invention was made with government support under Grants No. R01 AI104494, U01 DK082871, and R03 AI109460 awarded by the National Institutes of Health and UL1 TR0000448 awarded by the National Institutes of Health and the National Center for Advanced Translational Sciences. The government has certain rights in the invention.

BACKGROUND

I. Field

The disclosure relates to the fields of pathology, virology, molecular biology and pharmaceuticals. More specifically, the disclosure relates to the identification of candidate inhibitors for the treatment and prevention of herpesvirus diseases and Hepatitis B.

II. Related Art

For example, Herpesviridae is a large family of DNA viruses that cause diseases in vertebrates, including humans. These viruses are significant pathogens and, in addition to primary infections, cause latent, recurring infections. At least six species of Herpesviridae—herpes simplex virus 1 (HSV-1) and HSV-2 (both of which can cause orolabial herpes and genital herpes), Varicella-zoster virus (which causes chickenpox and shingles), Epstein-Barr virus (which causes mononucleosis), Cytomegalovirus (which causes mental retardation and deafness in neonates), and Human herpesvirus 6B (which causes roseola infantum and febrile seizures)—are extremely widespread among humans. More than 90% of adults have been infected with at least one of these, and a latent form of the virus remains in most people. Other viruses with human tropism include human herpesvirus 6A, human herpesvirus 7 and Kaposi's sarcoma-associated herpesvirus. There are more than 130 herpesviruses, including those that infect non-human mammals, birds, fish, reptiles, amphibians, and mollusks.

The drugs, acyclovir and ganciclovir, are considered the standard treatments and prophylactic agents for infections caused by HSV, VZV and CMV. Until a decade ago, the impact of acyclovir on the control of severe and life-threatening herpesvirus infections was unprecedented. Recently, approval of new drugs (i.e., penciclovir and the oral prodrugs, valaciclovir, famciclovir, cidofovir, fomivirsen, and foscarnet) has increased the number of therapeutic options for medical practitioners. Newer agents, such as brivudin and benzimidavir, are in ongoing clinical development, while others have been suspended because of safety concerns. Regardless, new anti-herpes agents are needed to face clinical issues such as drug resistance, increased use of anti-herpes prophylaxis, and safety concerns in small children or pregnant women.

Hepatitis B virus (HBV) is a hepatotropic DNA virus that replicates by reverse transcription (Hostomsky et al., 1993). It chronically infects >350 million people world-wide and kills up to 1.2 million patients annually by inducing liver failure and liver cancer (Steitz, 1995; Katayanagi et al., 1990; Yang et al., 1990; Lai et al., 2000). Reverse transcription is catalyzed by a virally-encoded polymerase that has two enzymatic activities: a DNA polymerase that synthesizes new DNA and a ribonuclease H (RNAseH) that destroys the viral RNA after it has been copied into DNA (Hostomsky et al., 1993; Rice et al., 2001; Hickman et al., 1994; Ariyoshi et al., 1994). Both activities are essential for viral replication.

HBV infections are treated with interferon α or one of five nucleos(t)ide analogs (Parker et al., 2004; Song et al., 2004; Lima et al., 2001). Interferon α leads to sustained clinical improvement in 20-30% of patients, but the infection is very rarely cleared (Hostomsky et al., 1993; Katayanagi et al., 1990; Braunshofer-Reiter et al., 1998). The nucleos(t)ide analogs are used more frequently than interferon. They inhibit DNA synthesis and suppress viral replication by 4-5 $\log_{10}$ in up to 70-90% patients, often to below the standard clinical detection limit of 300-400 copies/ml (Braunshofer-Reiter et al., 1998; Nowotny et al., 2005; Klumpp et al., 2003. However, treatment eradicates the infection as measured by loss of the viral surface antigen (HBsAg) from the serum in only 3-6% of patients even after years of therapy (Braunshofer-Reiter et al., 1998; Nowotny et al., 2005; Klumpp et al., 2003; Nowotny et al., 2006). Antiviral resistance was a major problem with the earlier nucleos(t)ide analogs, but resistance to the newer drugs entecavir and tenofovir is very low (Parker et al., 2004; Keck et al., 1998; Goedken et al., 2001; Li et al., 1995). This has converted HBV from a steadily worsening disease into a controllable condition for most individuals (McClure, 1993). The cost of this control is indefinite administration of the drugs (probably life-long; (Song et al., 2004), with ongoing expenses of $400-600/month (Poch et al., 1989; Hu et al. 1996; Hu et al., 1997) and unpredictable adverse effects associated with decades-long exposure to the drugs.

As such, there remains a need to develop new therapeutic options for these diseases.

SUMMARY

Thus, in accordance with the present disclosure, there is provided compounds which may be useful for inhibiting a cellular or herpesvirus nucleic acid metabolism enzyme. In other aspects, the compounds may be used in the treatment of hepatitis B viral infections.

In some aspects, the present disclosure provides compounds of the formula:

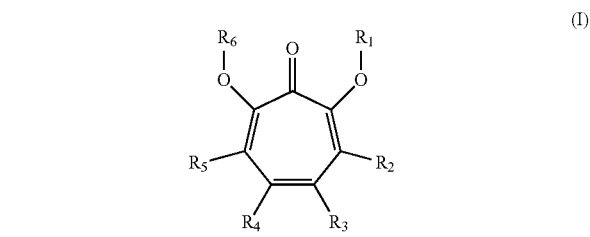

(I)

wherein:
R₁ and R₆ are each independently selected from hydrogen, alkyl$_{(C≤8)}$, substituted alkyl$_{(C≤8)}$, acyl$_{(C≤8)}$, or substituted acyl$_{(C≤8)}$;
R₂ and R₅ are each independently selected from hydrogen, hydroxy, alkyl$_{(C≤8)}$, substituted alkyl$_{(C≤8)}$, cycloalkyl$_{(C≤12)}$, substituted cycloalkyl$_{(C≤12)}$, aryl$_{(C≤8)}$, substituted aryl$_{(C≤8)}$, heteroaryl$_{(C≤8)}$, substituted heteroaryl$_{(C≤8)}$, alkoxy$_{(C≤8)}$, substituted alkoxy$_{(C≤8)}$, acyl$_{(C≤8)}$, or substituted acyl$_{(C≤8)}$; and
R₃ and R₄ are each independently selected from hydrogen, hydroxy, alkyl$_{(C≤12)}$, substituted alkyl$_{(C≤12)}$, cycloalkyl$_{(C≤12)}$, substituted cycloalkyl$_{(C≤12)}$, aryl$_{(C≤18)}$, substituted aryl$_{(C≤18)}$, heteroaryl$_{(C≤12)}$, substituted heteroaryl$_{(C≤12)}$, acyl$_{(C≤12)}$, substituted acyl$_{(C≤12)}$, or —C(O)R$_a$, wherein:
R$_a$ is alkyl$_{(C≤18)}$, cycloalkyl$_{(C≤18)}$, aryl$_{(C≤18)}$, heteroaryl$_{(C≤18)}$, alkoxy$_{(C≤18)}$, aryloxy$_{(C≤18)}$, -alkanediyl$_{(C≤6)}$-cycloalkyl$_{(C≤12)}$; or a substituted version of any of these groups; or
R₃ and R₄ are taken together and are a group of the formula:

—(CH₂)$_m$C(O)A(CH₂)$_n$—, wherein:

A is O or NR$_b$, wherein:
R$_b$ is hydrogen, alkyl$_{(C≤6)}$, or substituted alkyl$_{(C≤6)}$; and
m and n are each independently selected from 0, 1, 2, or 3;
or a pharmaceutically acceptable salt or tautomer thereof. In some embodiments, the compound is further defined as:

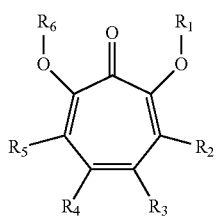

(I)

wherein:
R₁ and R₆ are each independently selected from hydrogen, alkyl$_{(C≤8)}$, substituted alkyl$_{(C≤8)}$, acyl$_{(C≤8)}$, or substituted acyl$_{(C≤8)}$;
R₂ and R₅ are each independently selected from hydrogen, hydroxy, alkyl$_{(C≤8)}$, substituted alkyl$_{(C≤8)}$, cycloalkyl$_{(C≤12)}$, substituted cycloalkyl$_{(C≤12)}$, aryl$_{(C≤8)}$, substituted aryl$_{(C≤8)}$, heteroaryl$_{(C≤8)}$, substituted heteroaryl$_{(C≤8)}$, alkoxy$_{(C≤8)}$, substituted alkoxy$_{(C≤8)}$, acyl$_{(C≤8)}$, or substituted acyl$_{(C≤8)}$; and
R₃ and R₄ are each independently selected from hydrogen, hydroxy, alkyl$_{(C≤12)}$, substituted alkyl$_{(C≤12)}$, cycloalkyl$_{(C≤12)}$, substituted cycloalkyl$_{(C≤12)}$, aryl$_{(C≤12)}$, substituted aryl$_{(C≤12)}$, heteroaryl$_{(C≤8)}$, substituted heteroaryl$_{(C≤8)}$, acyl$_{(C≤12)}$, substituted acyl$_{(C≤12)}$, or —C(O)R$_a$, wherein:
R$_a$ is alkyl$_{(C≤12)}$, cycloalkyl$_{(C≤12)}$, aryl$_{(C≤12)}$, heteroaryl$_{(C≤8)}$, alkoxy$_{(C≤12)}$, aryloxy$_{(C≤12)}$, -alkanediyl$_{(C≤6)}$-cycloalkyl$_{(C≤12)}$; or a substituted version of any of these groups;
or a pharmaceutically acceptable salt or tautomer thereof. In some embodiments, the compound is further defined as:

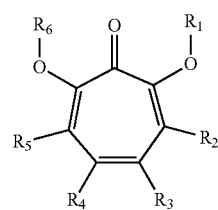

(I)

wherein:
R₁ and R₆ are each independently selected from hydrogen, alkyl$_{(C≤8)}$, substituted alkyl$_{(C≤8)}$, acyl$_{(C≤8)}$, or substituted acyl$_{(C≤8)}$;
R₂ and R₅ are each independently selected from hydrogen, hydroxy, alkyl$_{(C≤8)}$, substituted alkyl$_{(C≤8)}$, cycloalkyl$_{(C≤12)}$, substituted cycloalkyl$_{(C≤12)}$, aryl$_{(C≤8)}$, substituted aryl$_{(C≤8)}$, heteroaryl$_{(C≤8)}$, substituted heteroaryl$_{(C≤8)}$, alkoxy$_{(C≤8)}$, substituted alkoxy$_{(C≤8)}$, acyl$_{(C≤8)}$, or substituted acyl$_{(C≤8)}$; and
R₃ and R₄ are each independently selected from hydrogen, hydroxy, alkyl$_{(C≤12)}$, substituted alkyl$_{(C≤12)}$, cycloalkyl$_{(C≤12)}$, substituted cycloalkyl$_{(C≤12)}$, aryl$_{(C≤12)}$, substituted aryl$_{(C≤12)}$, heteroaryl$_{(C≤8)}$, substituted heteroaryl$_{(C≤8)}$, acyl$_{(C≤12)}$, substituted acyl$_{(C≤12)}$, or —C(O)R$_a$, wherein:
R$_a$ is alkyl$_{(C≤12)}$, cycloalkyl$_{(C≤12)}$, aryl$_{(C≤12)}$, heteroaryl$_{(C≤8)}$, alkoxy$_{(C≤12)}$, aryloxy$_{(C≤12)}$, -alkanediyl$_{(C≤6)}$-cycloalkyl$_{(C≤12)}$; or a substituted version of any of these groups;
or a pharmaceutically acceptable salt or tautomer thereof. In some embodiments, the compounds are further defined as:

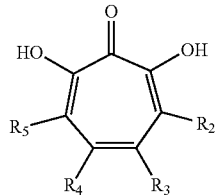

(II)

wherein: R₂, R₃, R₄, and R₅ are as defined above; or a pharmaceutically acceptable salt or tautomer thereof.

In some embodiments, R₁ is hydroxy. In some embodiments, R₆ is hydroxy. In some embodiments, R₂ is hydrogen, hydroxy, alkyl$_{(C≤8)}$, substituted alkyl$_{(C≤8)}$, acyl$_{(C≤8)}$, or substituted acyl$_{(C≤8)}$. In some embodiments, R₅ is hydrogen. In some embodiments, R₄ is alkyl$_{(C≤12)}$ or substituted alkyl$_{(C≤12)}$. In some embodiments, R₃ is aryl$_{(C≤12)}$, substituted aryl$_{(C≤12)}$, acyl$_{(C≤12)}$, substituted acyl$_{(C≤12)}$, or —C(O)R$_a$, wherein: R$_a$ is alkyl$_{(C≤12)}$, cycloalkyl$_{(C≤12)}$, aryl$_{(C≤12)}$, alkoxy$_{(C≤12)}$, aryloxy$_{(C≤12)}$, -alkanediyl$_{(C≤6)}$-cycloalkyl$_{(C≤12)}$; or a substituted version of any of these groups.

In some embodiments, the compounds are further defined as:
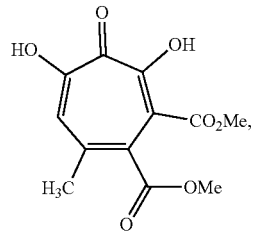 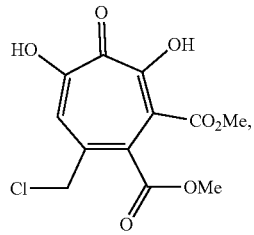
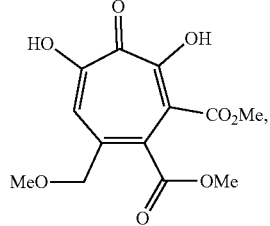 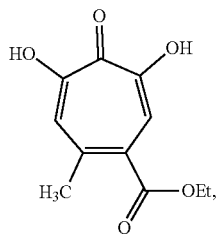
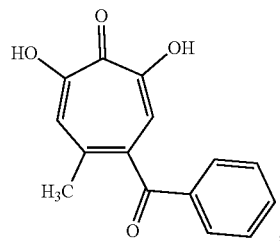 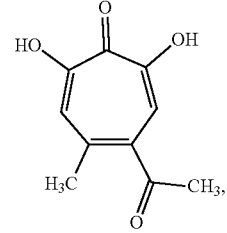
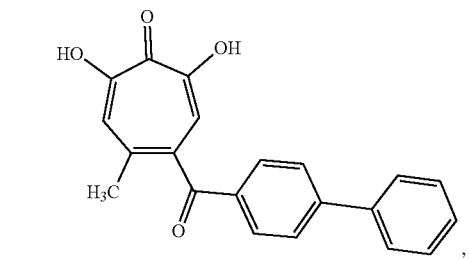
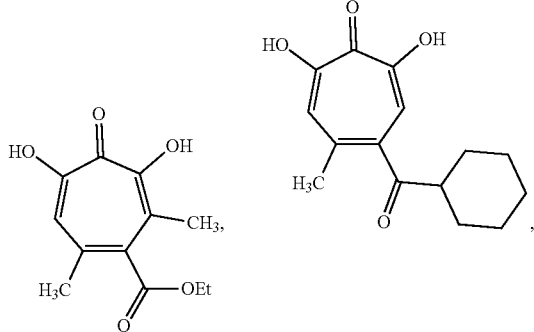
-continued
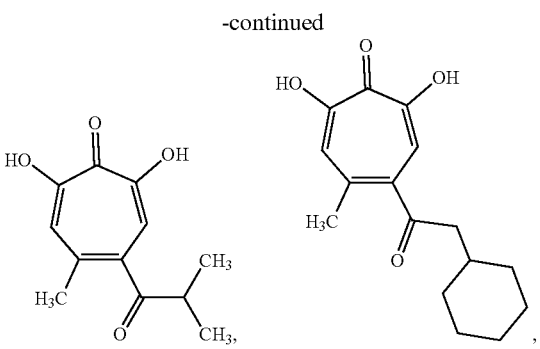
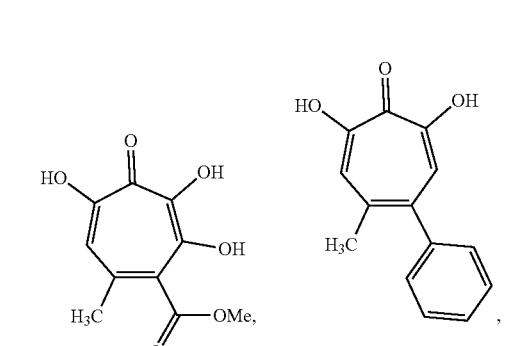
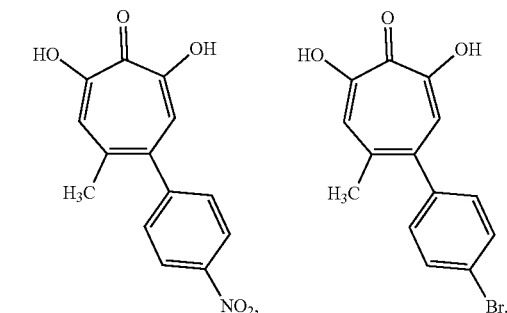
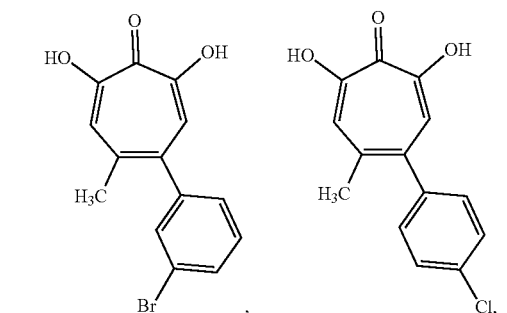
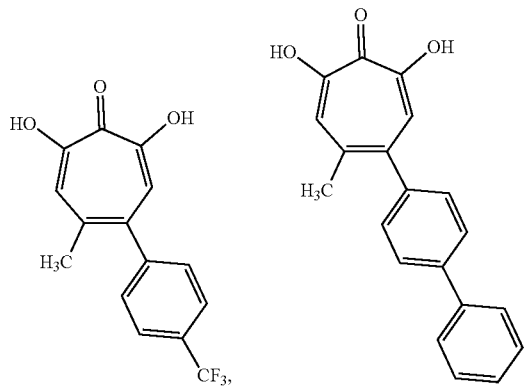

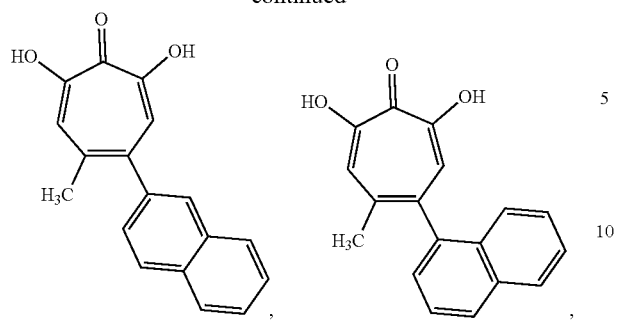
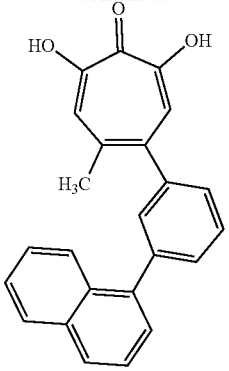
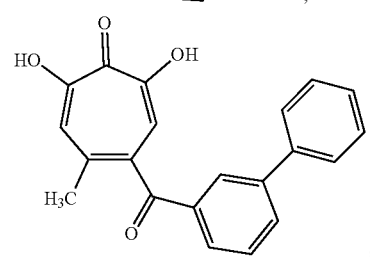
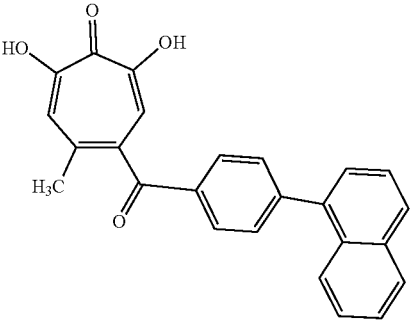
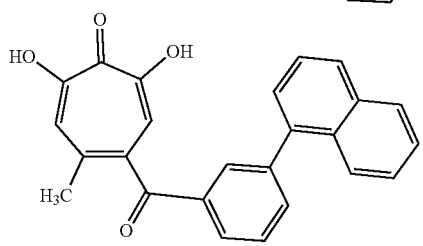
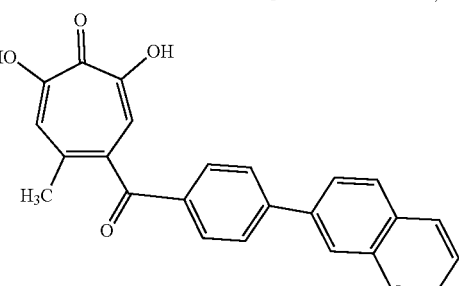
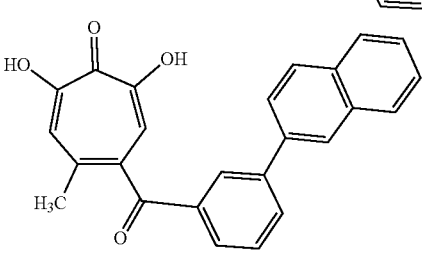

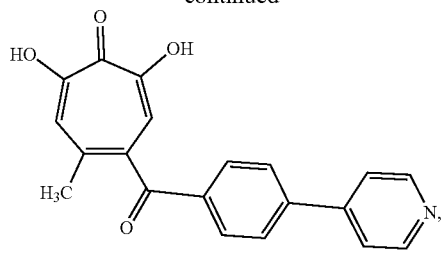
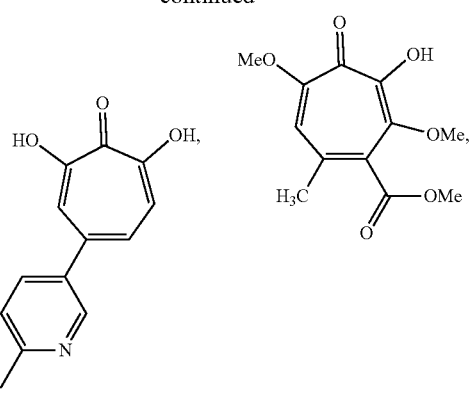
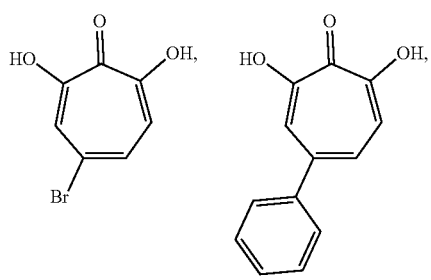
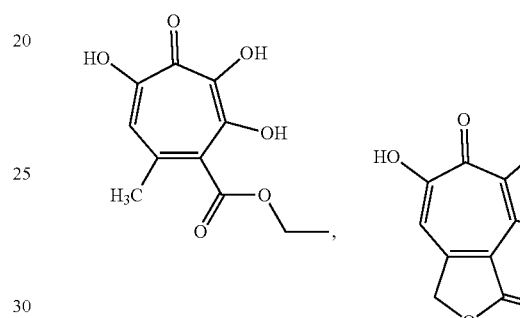
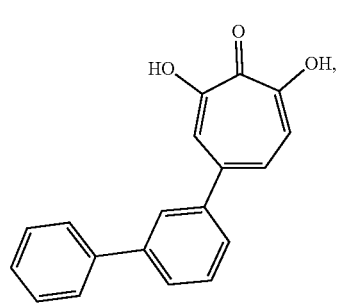
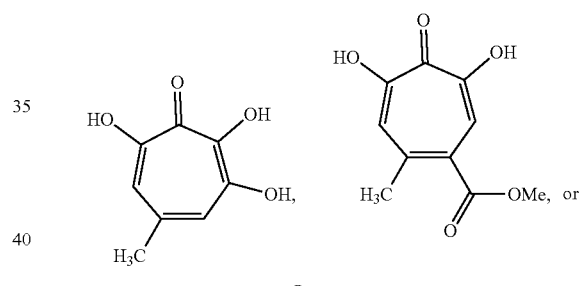
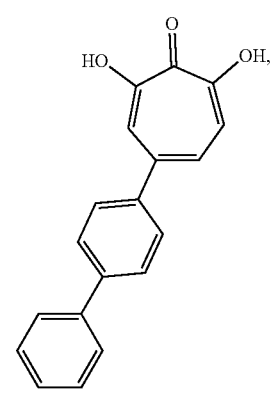
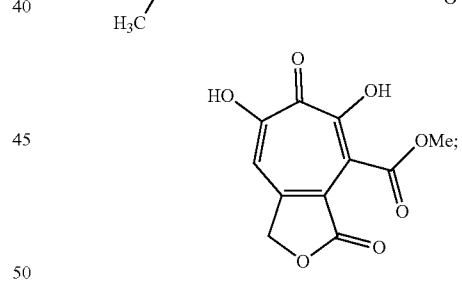
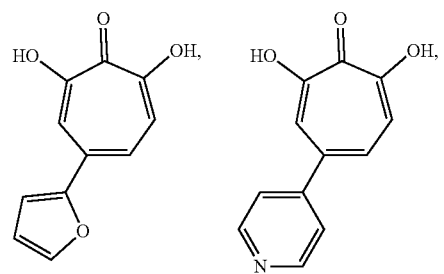
or a pharmaceutically acceptable salt or tautomer thereof. In some embodiments, the compounds are further defined as:
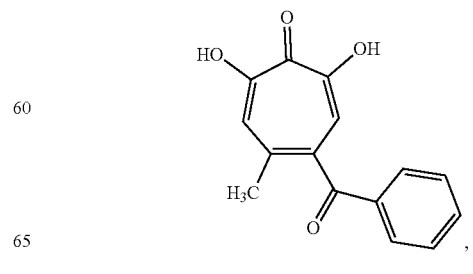

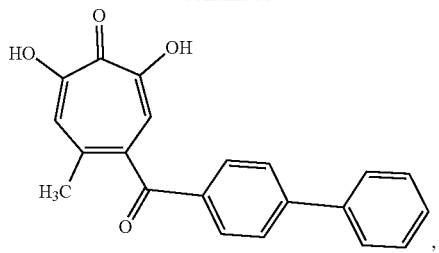
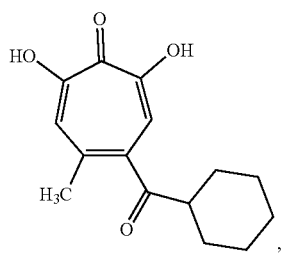
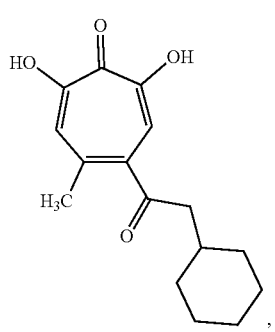
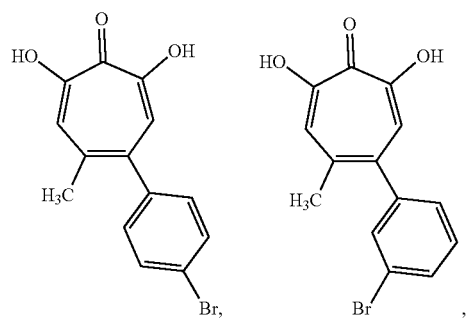
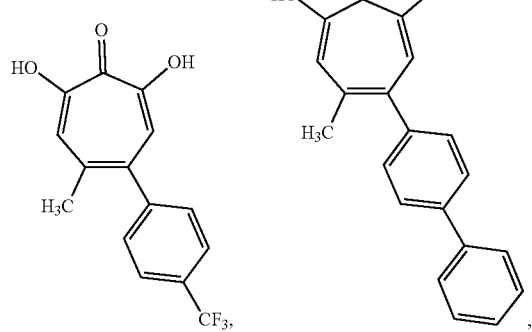
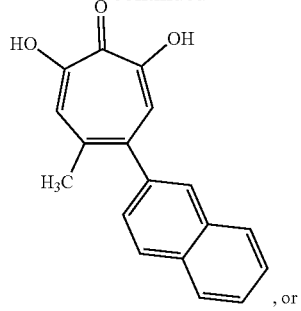
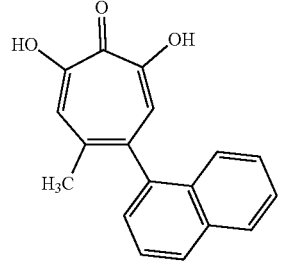
or a pharmaceutically acceptable salt or tautomer thereof. In some embodiments, the compound is further defined as:
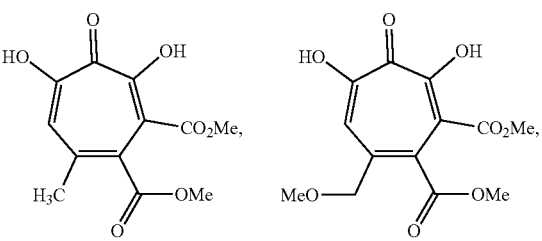
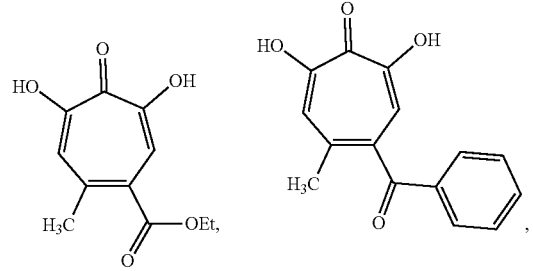
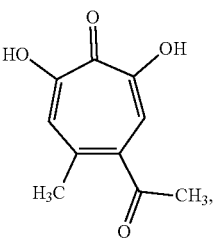
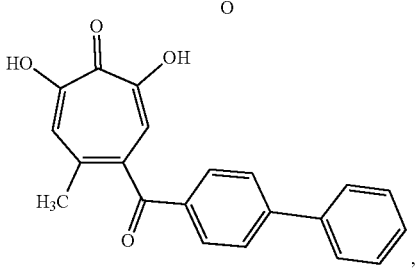

-continued
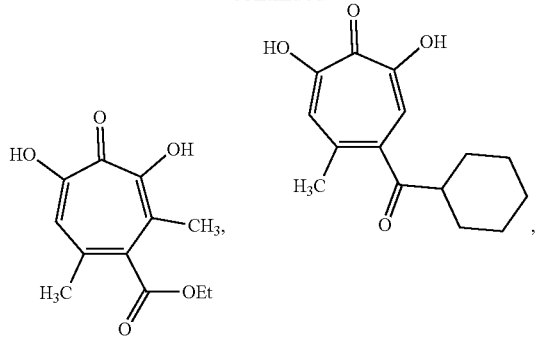
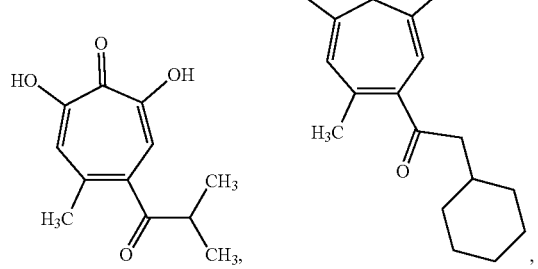
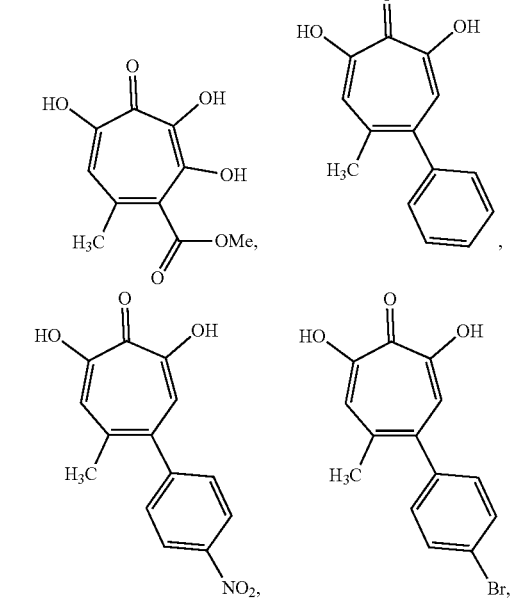
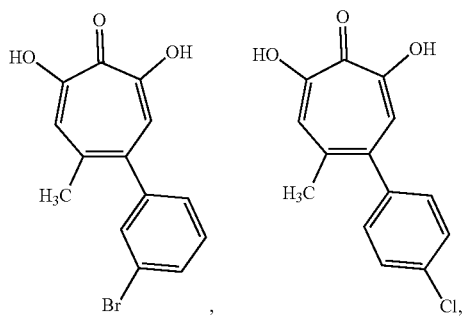
-continued
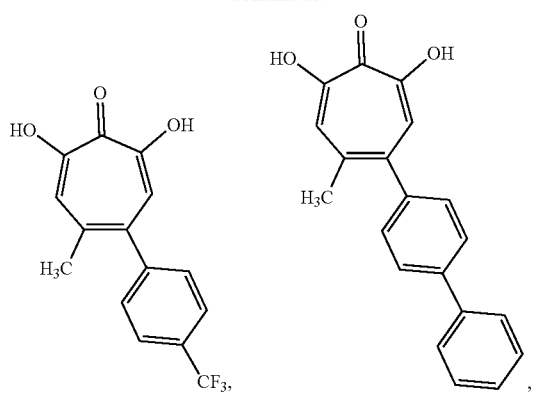
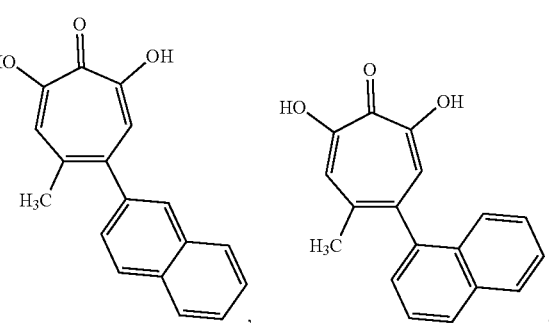
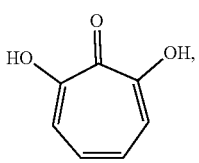
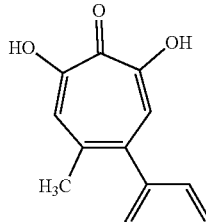
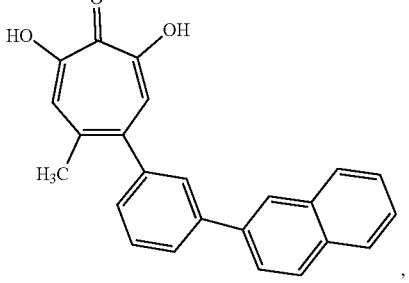

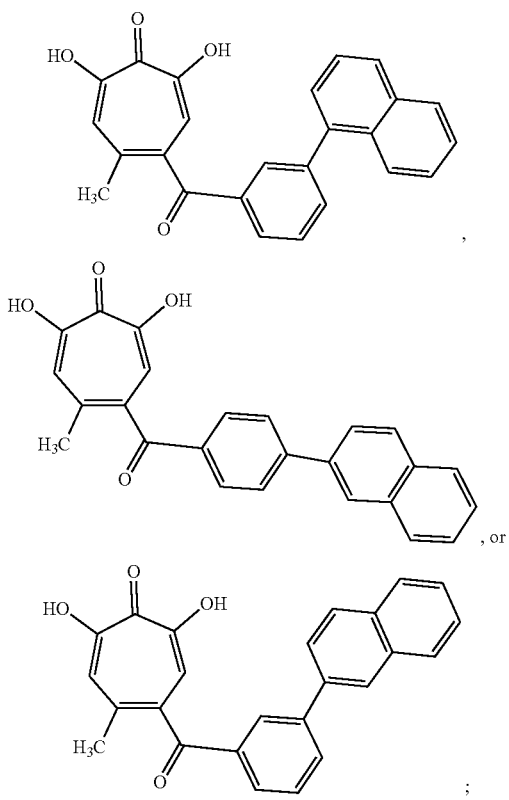
or a pharmaceutically acceptable salt or tautomer thereof. In some embodiments, the compound is further defined as:
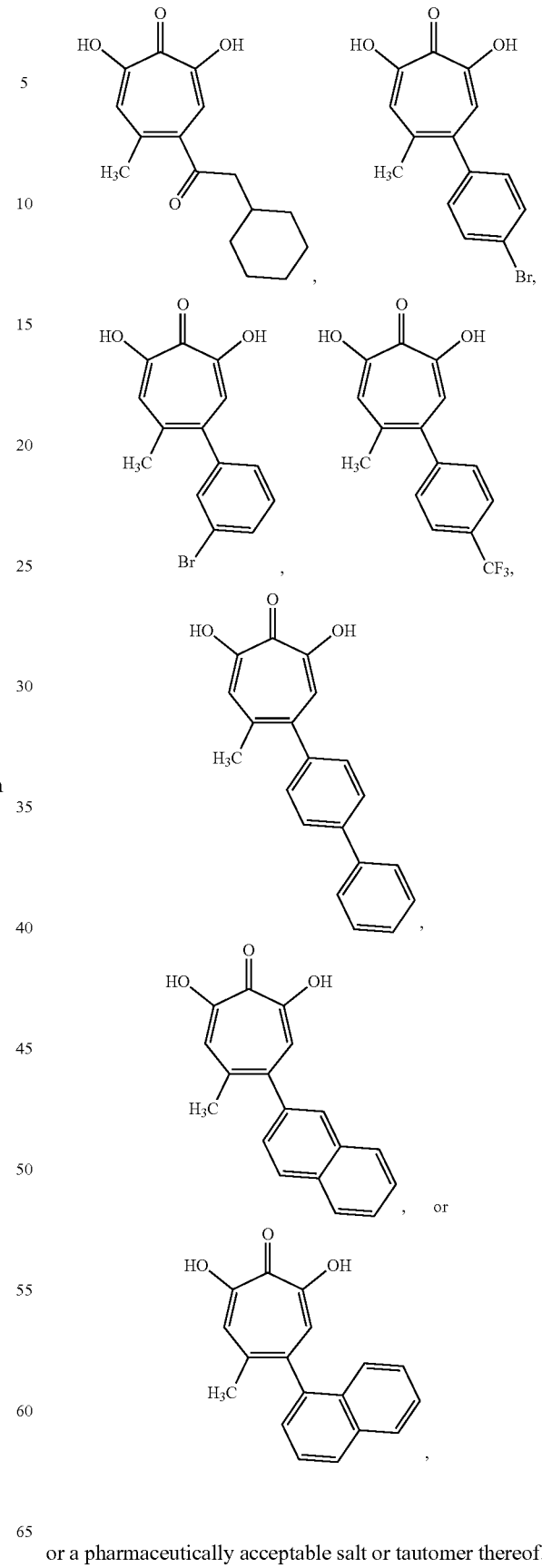
or a pharmaceutically acceptable salt or tautomer thereof. In some embodiments, the compound is further defined as:

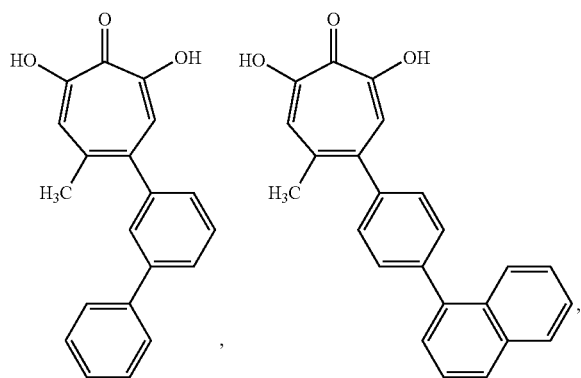

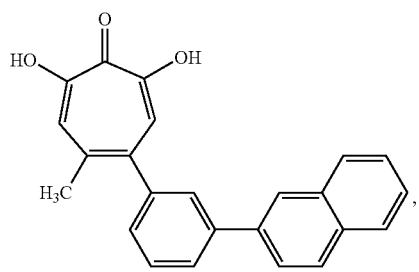

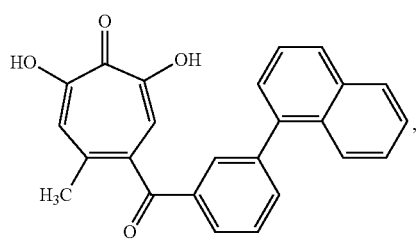

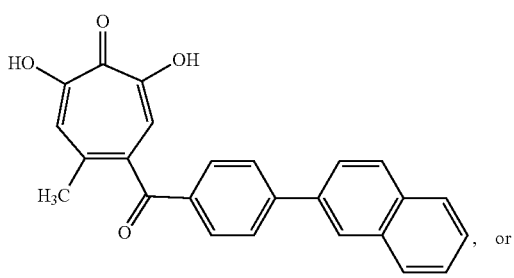

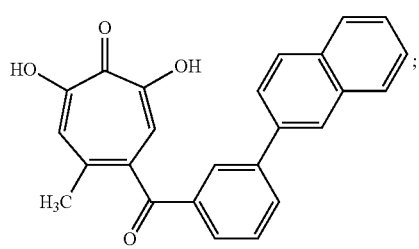

or a pharmaceutically acceptable salt or tautomer thereof.

In yet another aspect, the present disclosure provides a compound of the formula:

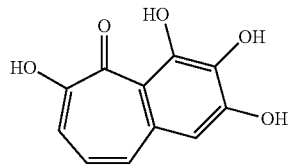 [SMILES: O=c1c(O)cccc2cc(O)c(O)c(O)c12]

or a pharmaceutically acceptable salt or tautomer thereof.

In still another aspect, the present disclosure provides pharmaceutical compositions comprising:
(a) a compound of the present disclosure; and
(b) a pharmaceutically acceptable carrier.

In some embodiments, the pharmaceutical compositions are formulated for administration: intravenously, intra-arterially, ocularly, orally, buccally, nasally, rectally, vaginally, topically, intramuscularly, intradermally, cutaneously or subcutaneously. In some embodiments, the pharmaceutical compositions are formulated for topical administration to the cornea.

In still yet another aspect, the present disclosure provides methods of inhibiting a cellular or herpesvirus nucleic acid metabolism enzyme comprising contacting said enzyme with a compound or composition of the present disclosure. The method may further comprise contacting said enzyme with a second inhibitor of said enzyme, or further comprise contacting said enzyme with said compound a second time. The enzyme may be located in a cell, which cell may be located in vitro or located in a living subject. The subject may be a vertebrate infected with a herpesvirus. The compound may be administered intravenously, intra-arterially, orally, buccally, ocularly, nasally, rectally, vaginally, topically, intramuscularly, intradermally, cutaneously or subcutaneously. The subject may be further administered a second anti-herpesvirus therapy distinct from the compound. The second anti-herpesvirus therapy may be foscarnet or a nucleoside analog, such as acyclovir, famciclovir, valaciclovir, penciclovir, or ganciclovir. The second anti-herpesvirus therapy may be administered to the subject before or after said compound. The second anti-herpesvirus therapy may be administered to said subject at the same time as said compound.

The subject may have previously received a first-line anti-herpesvirus therapy, and further may have developed resistance to said first-line anti-herpesvirus therapy. The herpevirus may be selected from a human alpha herpesvirus, a human beta herpesvirus or a human gamma herpesvirus. The human alpha herpesvirus may be selected from herpes simplex virus 1 (HSV-1), herpes simplex virus 2 (HSV-2), and Varicella-Zoster virus (VZV). The human beta herpesvirus may be selected from human cytomegalovirus (HCMV), human herpesvirus 6A (HHV-6A), human herpesvirus 6B (HHV-6B), and human herpesvirus 7 (HHV-7). The human gamma herpesvirus may be selected from Epstein-Barr virus (EBV) and Kaposi's sarcoma herpesvirus (KSHV). The herpesvirus may be a non-human herpesvirus, such as Marek's disease virus, equine herpesviruses, Bovine herpeviruses, pseudorabies virus, or herpesvirus of fish. In some embodiments, the compound is administered in a therapeutically effective amount sufficient to treat the subject infected with a herpesvirus.

In another aspect, the present disclosure provides methods of inhibiting a hepatitis B virus (HBV) nucleic acid metabolism enzyme comprising contact the enzyme with a compound or composition described herein. In some embodiments, the methods further comprise contacting the enzyme with a second inhibitor of HBV replication or with an anti-HBV drug that does not direct target the HBV enzymes.

In some embodiments, the second inhibitor is a nucleoside or nucleotide analog. In some embodiments, the second inhibitor is interferon alpha or pegylated interferon alpha. In some embodiments, the method further comprises contacting the enzyme with the compound a second time. In some embodiments, the enzyme is located in a cell. In some embodiments, the cell is located in vitro. In some embodiments, the cell is located in a living subject. In some embodiments, the subject is a mammal infected with HBV such as a human subject.

In some embodiments, the compound is administered intravenously, intra-arterially, orally, or subcutaneously. In some embodiments, the subject is further administered a second inhibitor of HBV replication. In some embodiments, the second inhibitor is a nucleoside or nucleotide analog. In some embodiments, the second inhibitor is interferon alpha or pegylated interferon alpha. In some embodiments, the second inhibitor is lamivudine, adefovir, telbivudine, entecavir, or tenofovir. In some embodiments, the second inhibitor is administered to the subject before or after said compound. In some embodiments, the second inhibitor is administered to the subject at the same time as said compound.

In some embodiments, the subject has previously received a first-line HBV therapy. In some embodiments, the HBV has developed resistance to the first-line HBV therapy. In some embodiments, the subject is administered interferon alpha or pegylated interferon alpha. In some embodiments, the compound is administered in a therapeutically effective amount sufficient to treat the subject infected with HBV.

In yet another aspect, the present disclosure provides methods of treating an infection of hepatitis B virus in a patient comprising administering to the patient a therapeutically effective amount of a compound or composition described herein.

In still yet another aspect, the present disclosure provides methods of treating an infection of herpesvirus in a patient comprising administering to the patient a therapeutically effective amount of a compound or composition described herein.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

In FIGS. 8B and 8C, the x axis indicates the effective concentration in this experiment for compound 118 alone, and the y axis indicates the effective concentration for ACV alone. The colored lines represent efficacy expected from mixing compound 118 and ACV at various proportions if the effects of the compounds are additive. The area below the lines indicates synergism, and the area above indicates antagonism. $EC_{90}$, $EC_{75}$, and $EC_{50}$ values were calculated in this experiment from the combinations of compound 118 and ACV.

DETAILED DESCRIPTION

Figure 1:
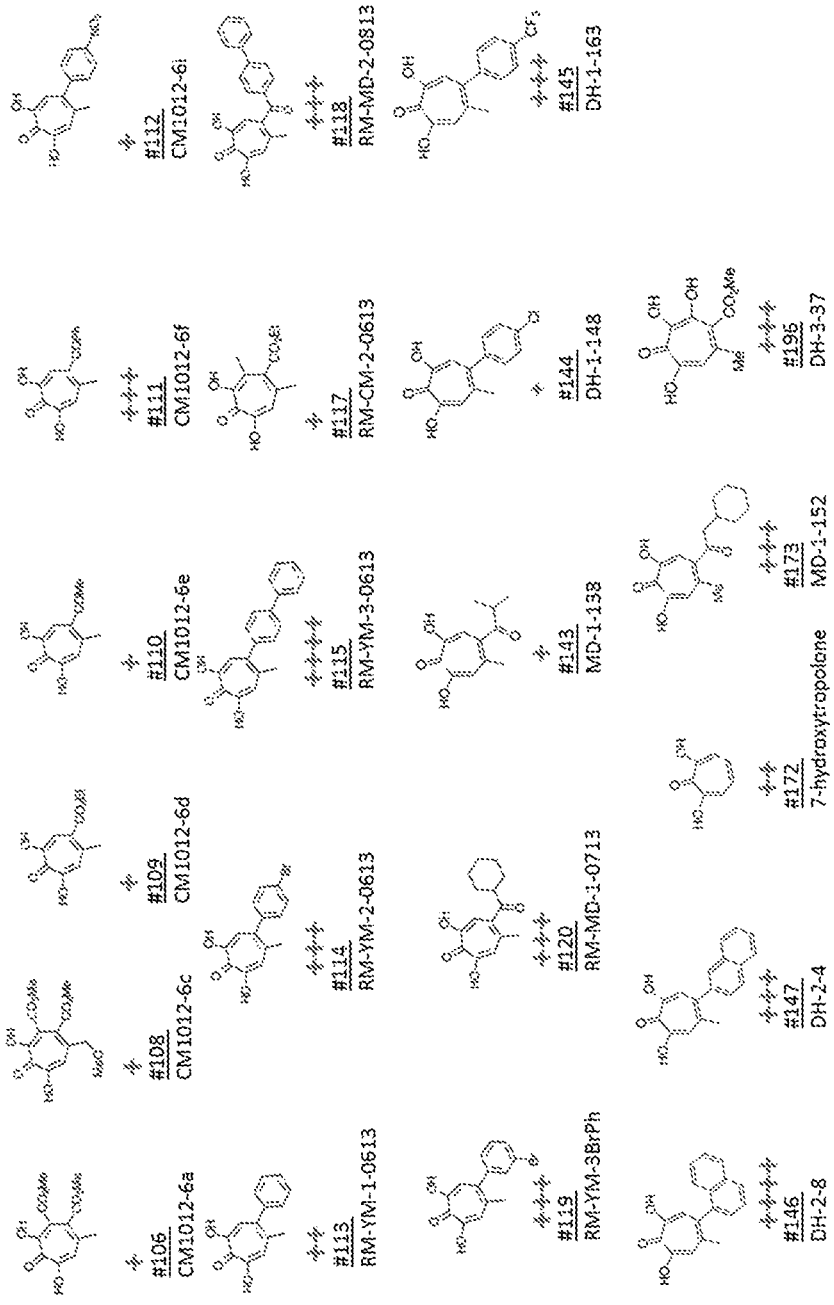
FIG. 1. Structure of some exemplary hydroxylated tropolones.

The inventors have previously demonstrated that inhibitors of nucleotidyl-transferase superfamily (NTS) enzymes can come from multiple different chemical classes. These compounds can profoundly suppress replication of HSV-1 and HSV-2 with no measurable toxicity in short-term cell culture assays. Here, the compounds described may have equal or superior activity as compared to the approved anti-herpesvirus drug acyclovir. Indeed, these compounds may already be superior to the many of the drugs that are used for herpesvirus infection. In other embodiments, these compounds may be used as inhibitors of hepatitis B virus. These compounds may be used in combination with another hepatitis B treatment to achieve synergistic results. Inhibitors of NTS enzymes like these compounds may well have a high barrier to development of antiviral resistance, and its unique mode of action suggests that they should be good candidates for combination therapy with the existing anti-herpesvirus drugs to improve overall efficacy of antiviral therapy. These and other aspects of the disclosure are discussed in detail below.

A. HERPESVIRUS

Herpesviruses are a diverse group of enveloped viruses having a large, double-stranded DNA genome enclosed in an icosahedral capsid (Pellet & Roizman 2013). The herpesviruses rely on the host cell RNA polymerase II for transcription, but encode all of the enzymes needed for replication of their genomes, including DNA polymerase, helicase, primase, terminase, ribonucleotide reductase, and thymidine kinase. All herpesviruses share the capacity to establish latency in host cells, allowing them to maintain the infection for the life of the host. Periodic reactivation from latency in response to cues in the cellular environment leads to lytic replication at mucosal surfaces, causing recurrent disease and providing the opportunity for transmission to uninfected individuals.

The herpesviruses are divided into three subclasses based primarily on their cellular tropism and characteristics of the latent infection. The human alpha herpesviruses herpes simplex virus 1 (HSV-1) (Roizman et al., 2013), herpes simplex virus 2 (HSV-2) (Roizman et al., 2013) and Varicella-Zoster virus (VZV) (Arvin & Gilden 2013) establish latency in sensory neurons where they may remain quiescent for long periods of time. HSV-1 and HSV-2 are similar viruses with colinear genomes and 83% nucleotide sequence identity in protein coding regions (Dolan et al., 1998); VZV contains a smaller, less homologous genome. The human beta herpesviruses human cytomegalovirus (HCMV), human herpesvirus 6A (HHV-6A), human herpesvirus 6B (HHV-6B), and human herpesvirus 7 (HHV-7) (Yamanishi et al., 2013) establish latency predominantly in mononuclear cells. The human gamma herpesviruses Epstein-Barr virus (EBV) (Longnecker et al., 2013) and Kaposi's sarcoma herpesvirus (KSHV) (Damania & Cesarman, 2013) stimulate cellular proliferation upon infection. EBV infects B lymphocytes, where it establishes latency, and also epithelial cells. By contrast, endothelial cells harbor the latent reservoir of KSHV, although the virus infects numerous other cell types as well. The genomes of latent beta and gamma herpesviruses are replicated as the host cell divides in order to maintain latent infection.

Herpesviruses related the human alpha, beta, and gamma herpesviruses infect numerous animal species, including several of significant economic importance. Key among these are pseudorabies virus which infects pigs, Marek's disease virus which infects chickens, bovine herpesvirus, equine herpesvirus, and salmonid and related herpesviruses that infect game fish.

1. Pathology

Primary infections with herpesviruses produce a broad spectrum of disease. HSV-1 causes numerous maladies (Roizman et al., 2013): gingivostomatitis; eczema herpeticum; herpes gladiatorum; less common but frequently fatal encephalitis; and an increasing proportion of ulcerative anogential lesions (Gilbert et al., 2011; Horowitz et al., 2011; Pena et al., 2010; Smith & Roberts 2009). Nearly two-thirds of the U.S. population has been exposed to HSV-1 (Xu et al., 2006). HSV-2 infects approximately 17% of Americans (Xu et al., 2006) and up to 75% of some demographics world-wide (Obasi et al., 1999 and Kamali et al., 1999), with an estimated global disease burden of more than half a billion people (Looker, et al., 2008). HSV-2 is the primary cause of ulcerative anogenital lesions. In addition, HSV-1 and HSV-2 may be transmitted from a pregnant woman to her child during birth, often causing potentially fatal disseminated disease in the newborn (Kimberlin 2007). HCMV is the most common in utero virus infection (Manicklal et al., 2013), and approximately 8,000 HCMV-infected infants born each year in the U.S. suffer sensorineural deafness, chorioretinitis, and/or mental retardation (James et al., 2009). In immunocompromised individuals, HCMV can cause mononucleosis, retinitis, colitis, pneumonitis, and esophagitis. These serious HCMV infections are associated with increased morbidity and mortality (Komatsu et al., 2014). EBV causes the vast majority of infectious mononucleosis, which strikes nearly half of young adults (Luzuriaga & Sullivan 2010). Notably, of the eight human herpesviruses, a vaccine is available only for VZV.

The novel capacity of herpesviruses to establish and reactivate from latency is also associated with numerous pathologies. HSV-1 causes recurrent cold sores; a significant proportion of devastating viral encephalitis; and corneal scarring known as herpetic stromal keratitis which is the most frequent infectious cause of blindness, afflicting nearly 400,000 persons annually in the U.S. (Roizman et al., 2013). HSV-2 frequently reactivates to cause genital ulcers and prior HSV-2 infection is associated with an increased risk of human immunodeficiency virus (HIV) acquisition (Roizman et al., 2013). Infants who survive HSV-1 or HSV-2 infections often experience life-long sequellae and periodic recurrent lesions (Kimberlin 2007 and James et al., 2009). VZV reactivates in up to half of older adults (Cohen 2013), and pain associated with the classic Zoster (shingles) rash and post-rash neuralgia can be excruciating. HCMV reactivation is associated with increased incidence of restenosis after angioplasty (Popovic et al., 2012), and also causes significant morbidity and mortality in recipients of bone marrow and solid organ transplants (Snydman 2008). Latent EBV infection is associated with a variety of cancers including Burkitt's lymphoma, two types of Hodgkin's lymphoma, non-Hodgkin's lymphoma, nasopharyngeal carcinoma, and post-transplant lymphoproliferative disease. Latent KSHV infection can lead to three types of cancer: Kaposi's sarcoma, pleural effusion lymphoma, and Castleman's disease (Damania & Cesarman 2013).

Veterinary herpesviruses also take a significant toll on livestock. Marek's disease is highly contagious, spreading rapidly through flocks of chickens that have not been vaccinated. It causes T cell lymphoma with infiltration of nerves and somatic organs, leading to paralysis and death in up to 80% of infected birds (Hirari, 2001). In addition, vaccine efficacy has declined with a concomitant increase in Marek's virus virulence (Gimeno, 2008). Pseudorabies (PRV) is the second most economically important viral disease of swine. Although PRV does not cause illness in adult swine, infection of pregnant sows results in a high incidence of fetal abortion or resorption (Smith, 1997). Piglets infected with PRV suffer coughing, sneezing, fever, constipation, and a variety of neurologic symptoms. Mortality in piglets less than one month of age is close to 100%, but declines rapidly with age (Nauwynck et al., 2007). Ruminants and dogs and cats are also susceptible to lethal PRV infection (Fenner et al., 1993). In cattle, symptoms include intense itching followed by neurological signs and death. In dogs, intense itching is accompanied by jaw and pharyngeal paralysis and subsequent death (Decaro et al., 2008). In cats, usually no symptoms are observed because the disease is so rapidly fatal (Gaskell et al., 2007). Bovine herpesviruses (BHV) cause a variety of illnesses in young cattle, and can also cause abortion. Although the illnesses caused by BHVs are mostly not life-threatening, they are economically important diseases because infection may trigger a decline in meat and milk production and affect trade restrictions (Nandi et al., 2009). Equine herpesviruses typically cause respiratory disease, but certain species also cause myeloencephalopathy in horses, abortion and occasionally neonatal mortality due to pneumonia (Fortier et al., 2010). The herpesviruses of various fish species can cause significant mortality in aquaculture settings, particularly at the fingerling stage (Hanson et al., 2011). Importantly, all of these viruses share the same basic genomic replication mechanisms, so if the presumed mechanism by which the NTS enzymes inhibit HSV-1 and HSV-2 is correct, most of the other herpesvirus pathogens should also be highly sensitive to NTS inhibitors. Development of NTS inhibitors into anti-herpesvirus drugs would be particularly valuable in cases like HCMV, where current antiviral therapies frequently drive resistance and are plagued by toxicity issues (Weller and Kuchta, 2013). Finally, NTS inhibitors may be promising candidates for pan anti-herpesvirus drug development due to similarities in replication mechanisms of all the herpesviruses.

2. Infection and Latency

Enveloped herpesvirus particles fuse with the plasma membrane of a cell, releasing viral regulatory proteins and the viral capsid containing the linear double-stranded DNA genome into the cytoplasm. The capsids deliver the viral genome to the nucleus via release through nuclear pores, whereupon the genome circularizes and becomes transcriptionally active. Viral infection at this point can proceed by two patterns, lytic or latent. In the lytic cycle, coordinated phases of viral transcription lead to expression of the viral regulatory proteins, viral enzymes, and concurrently with the onset of DNA replication, the viral structural proteins. Nascent viral capsids assemble in the nucleus and then bud through the nuclear membranes to acquire their envelope (Mettenleiter et al., 2009). Release from the cells is primarily lytic, resulting in the death of the cell. Alternatively, the virus may enter a latent state, where transcription is limited to a few viral regulatory loci and viral DNA replication is strictly limited. Upon recognition of appropriate cellular stimuli, viral transcription reverts to the lytic pattern and productive viral replication occurs.

Initial infections with alpha herpesviruses are lytic, resulting in dispersion of the virus to other cells and organs. These viruses establish latency in the unique environment of the neuron, and also in satellite cells in the case of VZV. During latency, replication of alpha herpesvirus DNA may occur at a low level because latently infected neurons contain multiple copies of the genome (Chen et al., 2002; Wang et al., 2005). Once latency is established, DNA replication increases markedly only during a reactivation event. Initial infections with beta herpesviruses are typically non-lytic but may cause cell-cell fusion. The gamma herpesviruses stimulate proliferation of infected cells, replicating their DNA along with cellular DNA replication to transmit copies of the viral genome to daughter cells (Longnecker et al., 2013). All the herpesviruses cause episodic lytic infection of at least some cell types, allowing them to be shed from mucosal surfaces to facilitate transmission to uninfected individuals.

3. Genomic Replication

Circularization of the linear double-stranded herpesvirus DNA occurs in the nucleus shortly after viral uncoating, presumably through a recombination-mediated event. Replication of the viral DNA occurs in the nucleus within three-dimensional domains termed replication compartments (Quinlan et al., 1984). DNA replication is thought to employ a double-stranded rolling circle mechanism [reviewed in (Weller & Coen 2012; Lehman & Boehmer 1999)]. In preparation for viral DNA replication, virus-encoded transcriptional activators upregulate expression of proteins involved in nucleic acid metabolism. DNA replication then initiates at one of three viral origins of DNA replication and is mediated through action of the viral ICP6 origin binding protein. (All viral gene names in this section are for HSV-1). DNA synthesis is primed by the viral helicase/primase complex (pUL5, pUL8, and pUL52). DNA elongation occurs by coupled leading- and lagging-strand DNA synthesis through formation of a replication fork that is grossly similar to the forks that replicate cellular DNA. DNA synthesis is catalyzed by the pUL30 DNA polymerase/UL42 processivity protein complex that also possesses 5'-3' exonuclease, 3'-5' exonuclease, and RNase H activities. Helical torsion is relieved by the viral helicase/primase complex, and proper replication fork initiation, architecture and dynamics are promoted by the ICP8 single-stranded DNA binding protein. The initial product of DNA replication is a head-to-tail concatamer, but later in the replication cycle complex branched concatamers accumulate through recombination and/or re-initiation mechanisms. The concatamer is cleaved to unit length by the terminase complex (pUL15, pUL28, and pUL33) (Selvarajan et al., 2013) during encapsidation of the viral genome into pre-formed viral capsids. Without wishing to be bound by any theory it is believed that some of the compounds may interact with the pUL15 terminase subunit.

4. Therapeutic Targets

Possible Targets for Nucleotidyl Transferase Superfamily Inhibitors in the Herpesvirus Genomes.

The inhibitors screened here function against HIV by binding to the viral RNase H or integrase active sites and chelating the essential divalent cations within the active site (Fuji et al., 2009; Su et al., 2010; Chung et al., 2011; Billamboz et al., 2011; Himmel et al., 2009; Kirschberg et al., 2009). Other compounds screened here are chemically related to inhibitors of the HIV RNase H and integrase. Therefore, their presumed mechanism of action is to inhibit one or more of the viral and/or cellular NTS enzymes essential for herpesviral genomic replication. This mechanism has not yet been tested.

For the herpes simplex viruses, candidate genes include the RNase H activity of the pUL30 DNA polymerase (Liu et al., 2006), the 3'-5' exonuclease activity of pUL30 (Coen 1996), the strand transfer activity of ICP8 (Bortner et al., 1993; Nimonkar & Boehmer, 2003), or the 5'-3' exonuclease activity of the pUL12 polymerase accessory protein (Schumacher et al., 2012) that are directly involved in virus replication (Weller & Coen 2012). The pUL15 terminase protein that cleaves the concatameric viral DNA produced by DNA replication into the mature linear monomers is also a prime candidate (Selvarajan et al., 2013).

Other herpesviruses encode proteins with functions consistent with NTS enzymes that could be plausible targets. For example, pUL98 is the HCMV ortholog of HSV pUL12 and is functionally conserved, as demonstrated by trans-complementation experiments (Gao et al., 1998). At least two of the seven HCMV proteins involved in encapsidation form an essential terminase complex which likely functions as both an endonuclease and a DNA translocase during DNA cleavage and packaging (Bogner, 2002; Hwang & Bogner, 2002; Scheffczik et al., 2002; Scholz et al., 2003). These genes are conserved throughout the herpesvirus family (Alba et al., 2001) and deletion of any of the seven results in accumulation of empty capsids in the nucleus. The human cytomegalovirus (HCMV) terminase subunits pUL56 and pUL89, encoded by the UL56 and UL89 genes, have been extensively studied. Both gene products form toroidal structures, bind DNA, and have nuclease activity (Bogner et al., 1998; Scheffczik et al., 2002). While pUL56 mediates the specific binding to pac sequences on DNA concatamers and provides energy and structural assistance for DNA translocation into the procapsids, pUL89 cleaves the DNA concatomers (Bogner, 2002). These are the orthologs of HSV terminase subunits pUL15 and pUL28.

Cellular proteins are also plausible targets for the action of the NTS inhibitors, especially because DNA recombination events appear to be important during productive replication (Weller & Coen 2012). These proteins include the human RNase H1 that could assist in removal of RNA primers for DNA synthesis. Other candidates include the Fen1 endonuclease that may assist in removal of primers (Zhu et al., 2010), and the double-stranded break repair enzymes Mre11, Rad50, NBS1, Rad51 (Weizman & Weller 2011), and Rad52 (Schumacher et al., 2012). The base-excision repair enzymes SSH2 and MLH1 which form complexes that are recruited to viral replication sites and contribute to HSV genomic replication (Mohni et al., 2011) are also plausible targets.

5. Treatments

Herpesvirus DNA polymerase inhibitors (nucleoside analogs), including acyclovir, famciclovir, valaciclovir, penciclovir, and ganciclovir are the most common forms of treatment. A pyrophosphate analog, foscarnet, also inhibits the herpesvirus DNA polymerases. A DNA helicase-primase inhibitor, AIC316 (pritelivir), was shown to reduce HSV-2 shedding and number of days without lesions in a phase 2 clinical trial (Wald et al., 2014). However, a subsequent double-blind trial by the same group was terminated by the sponsor because of concurrent findings of toxicity in monkeys (De et al., 2015). Similarly, the helicase-primase inhibitor Amenamevir (ASP2151) is active against HSV-1 and HSV-2 in culture (Chono et al., 2010) and significantly reduced the median time to lesion healing in a phase II clinical trial (Tyring et al., 2012), but a subsequent trial was terminated due to adverse effects (De et al., 2015). CMX001 (brincidofovir), an orally bioavailable lipid conjugate of cidofovir, potentiates the antiviral effect of acyclovir in mice inoculated intranasally with HSV-1 or HSV-2 (Prichard et al., 2011). N-Methanocarbathymidine (N-MCT) reduces lethality in a mouse model of HSV-2 infection (Quenelle et al., 2011) and a guinea pig model of neonatal herpes (Bemstein et al., 2011). N-MCT also reduces acute and recurrent disease caused by HSV-2 in an adult guinea pig model. The monoamine oxidase inhibitor tranylcypromine (TCP), which also blocks the activity of histone demethylase LSD1, reduces HSV-1 infection of the cornea, trigeminal ganglia and brain of mice, corneal disease, and percentage of mice shedding virus upon induced reactivation (Yao et al., 2014). TCP has also been tested in a rabbit eye model of recurrent infection with HSV-1 and the mouse and guinea pig models of HSV-2 genital infection. An acyclic nucleoside phosphonate, PMEO-DAPym, inhibits HSV replication in a variety of cultured cell types by targeting the viral DNA polymerase (Balzarini et al., 2013). The HIV integrase inhibitor, Raltegravir, has a small amount of inhibitory activity against replication of several herpesviruses in cultured cells (Zhou et al., 2014; Yan et al., 2014) and appears to target the polymerase processivity factor UL42 (Zhou et al., 2014). Two other integrase inhibitors, XZ15 and XZ45, reduce replication of HSV-1 in cell culture by approximately 800- to 8000-fold, respectively (Yan et al., 2014). XZ45 also inhibits HCMV replication and KSHV gene expression (Yan et al., 2014).

Therapy based on existing drugs such as acyclovir is incompletely effective (Johnston et al., 2012), and viral resistance to current nucleos(t)ide analog therapies is relatively common. Acyclovir resistant variants are particularly prevalent among children, the immunocompromised, and patients with herpetic stromal keratitis (Duan et al., 2008; Wang et al., 2011; Field & Vere Hodge, 2013; Morfin & Thouvenot, 2003; Andrei & Snoeck, 2013). Ganciclovir-resistant variants occur in the naturally circulating viral population (Drew et al., 1993) and can be selected in patients over time (Marfori et al., 2007; Imai et al., 2004; Drew et al., 2001; Drew et al., 1999).

B. HEPATITIS B VIRUS

1. Biology

Hepatitis B virus, abbreviated HBV, is a species of the genus *Orthohepadnavirus*, which is likewise a part of the Hepadnaviridae family of viruses. This virus causes the disease hepatitis B. In addition to causing hepatitis B, infection with HBV can lead to hepatic fibrosis, cirrhosis and hepatocellular carcinoma. It has also been suggested that it may increase the risk of pancreatic cancer.

The hepatitis B virus is classified as the type species of the *Orthohepadnavirus*, which contains at least five other species: the pomona roundleaf bat hepatitis virus, long-fingered bat hepatitis virus, the Ground squirrel hepatitis virus, Woodchuck hepatitis virus, and the Woolly monkey hepatitis B virus. The genus is classified as part of the Hepadnaviridae family, which contains two other genera, the *Avihepadnavirus* and a second which has yet to be assigned. This family of viruses have not been assigned to a viral order. Viruses similar to hepatitis B have been found in all the Old World apes (orangutan, gibbons, gorillas and chimpanzees) and from a New World woolly monkey suggesting an ancient origin for this virus in primates.

The virus is divided into four major serotypes (adr, adw, ayr, ayw) based on antigenic epitopes present on its envelope proteins, and into at least eight genotypes (A-H) according to overall nucleotide sequence variation of the genome. The genotypes have a distinct geographical distribution and are used in tracing the evolution and transmission of the virus. Differences between genotypes affect the disease severity, course and likelihood of complications, and response to treatment and possibly vaccination.

The virus particle (virion) consists of an outer lipid envelope and an icosahedral nucleocapsid core composed of protein. The nucleocapsid encloses the viral DNA and a DNA polymerase that has reverse transcriptase activity similar to retroviruses. The outer envelope contains embedded proteins which are involved in viral binding of, and entry into, susceptible cells. The virus is one of the smallest enveloped animal viruses with a virion diameter of 42 nm, but pleomorphic forms exist, including filamentous and spherical bodies that both lack a core. These particles are not infectious and are composed of the lipid and protein that forms part of the surface of the virion, which is called the surface antigen (HBsAg), and are produced in excess during the life cycle of the virus. The HBV virus itself is called a Dane particle and consists of HBsAg, a lipid envelope, the core protein (HBcAg), the viral genome, and the Hepatitis B virus DNA polymerase. The functions of the small regulatory protein (HBx) are not yet well known but may be related to interfering with transcription, signal transduction, signal transduction, cell cycle progress, protein degradation, apoptosis, or chromosomal stability. The virus also produces a secreted protein called HBeAg that is an amino-terminal extension of HBcAg initiating from an upstream start codon that is involved in suppressing antiviral immune responses.

The genome of HBV in virions is made of circular DNA, but it is unusual because the DNA is not fully double-stranded. One end of the full length strand is linked to the viral DNA polymerase. The genome is 3020-3320 nucleotides long (for the full length strand) and 1700-2800 nucleotides long (for the short length strand). The negative-sense, (non-coding), strand is the complete strand and it is complementary to the viral mRNA. The viral DNA is found in the nucleus soon after infection of the cell. The partially double-stranded DNA is rendered fully double-stranded shortly after infection of a cell by completion of the (+) sense strand and removal of a protein molecule from the (−) sense strand and a short sequence of RNA from the (+) sense strand. A short terminal duplication of are removed from the ends of the (−)sense strand and the ends are rejoined. The mature nuclear form of the genome is called the "cccDNA." The cccDNA is the template for transcription of all of the viral mRNAs.

There are four known genes encoded by the genome called C, X, P, and S. The core protein (HBcAg) is coded for by gene C, and its start codon is preceded by an upstream in-frame AUG start codon from which the pre-core protein is produced. HBeAg is produced by proteolytic processing of the pre-core protein. The DNA polymerase is encoded by gene P. Gene S is the gene that codes for the surface antigens (HBsAg). The HBsAg gene is one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced. The function of the protein coded for by gene X is not fully understood, but it has pleiotropic regulatory functions in both the cytoplasm and nucleus.

There are at least eight known genotypes labeled A through H. A possible new "I" genotype has been described, but acceptance of this notation is not universal. Different genotypes may respond to treatment in different ways. The genotypes differ by at least 8% of the sequence and have distinct geographical distributions and this has been associated with anthropological history. Type F which diverges from the other genomes by 14% is the most divergent type known. Type A is prevalent in Europe, Africa and South-east Asia, including the Philippines. Type B and C are predominant in Asia; type D is common in the Mediterranean area, the Middle East and India; type E is localized in sub-Saharan Africa; type F (or H) is restricted to Central and South America. Type G has been found in France and Germany. Genotypes A, D and F are predominant in Brazil and all genotypes occur in the United States with frequencies dependent on ethnicity. The E and F strains appear to have originated in aboriginal populations of Africa and the New World, respectively. Within these genotypes, 24 subtypes have been described which differ by 4-8% of the genome:

Type A has two subtypes: Aa (A1) in Africa/Asia and the Philippines and Ae (A2) in Europe/United States.

Type B has two distinct geographical distributions: Bj/B1 ('j'—Japan) and Ba/B2 ('a'—Asia). Type Ba has been further subdivided into four clades (B2-B4).

Type C has two geographically subtypes: Cs (C1) in South-east Asia and Ce (C2) in East Asia. The C subtypes have been divided into five clades (C1-C5). A sixth clade (C6) has been described in the Philippines but only in one isolate to date. Type C1 is associated with Vietnam, Myanmar and Thailand; type C2 with Japan, Korea and China; type C3 with New Caledonia and Polynesia; C4 with Australia; and C5 with the Philippines. A further subtype has been described in Papua, Indonesia.

Type D has been divided into 7 subtypes (D1-D7).

Type F has been subdivided into 4 subtypes (F1-F4). F1 has been further divided in to 1a and 1b. In Venezuela subtypes F1, F2, and F3 are found in East and West Amerindians. Among South Amerindians only F3 was found. Subtypes Ia, III, and IV exhibit a restricted geographic distribution (Central America, the North and the South of South America respectively) while clades Ib and II are found in all the Americas except in the Northern South America and North America respectively.

The life cycle of hepatitis B virus is complex. Hepatitis B is one of a few known non-retroviral viruses which use reverse transcription as a part of its replication process:

Attachment—The virus gains entry into the cell by binding to a receptor on the surface of the cell and enters it by endocytosis.

Penetration—The virus membrane then fuses with the host cell's membrane releasing the DNA and core proteins into the cytoplasm.

Uncoating—Because the virus multiplies via RNA made by a host enzyme, the viral genomic DNA has to be transferred to the cell nucleus by host proteins. The core proteins dissociate from the partially double-stranded viral DNA is then made fully double-stranded and transformed into covalently closed circular DNA (cccDNA) that serves as a template for transcription of four viral mRNAs.

Replication—The cccDNA is the transcriptional template for all of HBV's RNAs. The largest of the mRNAs is called the pre-core mRNA that encodes HBeAg. A slightly shorter mRNA is called the pregenomic RNA that encodes the HBcAg and the viral DNA polymerase. Both the precore and pregenomic RNAs are longer than the viral genome, but only the pregenomic RNA is packaged into nascent core particles along with the viral polymerase. Reverse transcription within the capsids is catalyzed by the coordinate activity of the viral DNA polymerase's reverse transcriptase and ribonuclease H activities and results in the partially double-stranded viral DNA found within HBV virions.

Assembly and Release—Progeny virions are formed budding of the viral capsid particles containing the viral DNA into endoplasmic-reticulum-derived membranes, where they pick up their envelope and HBsAgs are released from the cell by non-cytolytic secretion or are returned to the nucleus and re-cycled to produce even more copies of the nuclear cccDNA.

2. Treatment

Currently, there are seven FDA approved drugs in the U.S. to treat chronic HBV: Intron A® (Interferon Alpha), Pegasys® (Pegylated Interferon), Epivir HBV® (Lamivudine), Hepsera® (Adefovir), Baraclude® (Entecavir), Tyzeka® (Telbivudine), and Viread® (Tenofovir).

Adefovir, previously called bis-POM PMEA, with trade names Preveon® and Hepsera®, is an orally-administered nucleotide analog reverse transcriptase inhibitor (ntRTI). It can be formulated as the pivoxil prodrug adefovir dipivoxil. Adefovir works by blocking reverse transcriptase, the enzyme that is crucial for the hepatitis B virus (HBV) to reproduce in the body because it synthesizes the viral DNA. It is approved for the treatment of chronic hepatitis B in adults with evidence of active viral replication and either evidence of persistent elevations in serum aminotransferases (primarily ALT) or histologically active disease. The main benefit of adefovir over drugs like lamivudine (below) is that it takes a much longer period of time before the virus develops resistance to it. Adefovir dipivoxil contains two pivaloyloxymethyl units, making it a prodrug form of adefovir.

Lamivudine (2',3'-dideoxy-3'-thiacytidine, commonly called 3TC) is a potent nucleoside analog reverse transcriptase inhibitor (nRTI). It is marketed by GlaxoSmithKline with the brand names Zeffix®, Heptovir®, Epivir®, and Epivir-HBV®. Lamivudine has been used for treatment of chronic hepatitis B at a lower dose than for treatment of HIV. It improves the seroconversion of HBeAg positive hepatitis B and also improves histology staging of the liver. Long term use of lamivudine unfortunately leads to emergence of a resistant hepatitis B virus mutants with alterations in the key YMDD reverse transcriptase motif. Despite this, lamivudine is still used widely as it is well tolerated and as it is less expensive than the newer drugs and is the only anti-HBV drug many people in emerging economies can afford.

Lamivudine is an analogue of cytidine. It can inhibit both types (1 and 2) of HIV reverse transcriptase and also the reverse transcriptase of hepatitis B. It is phosphorylated to active metabolites that compete for incorporation into viral DNA. It inhibits the HIV reverse transcriptase enzyme competitively and acts as a chain terminator of DNA synthesis. The lack of a 3'-OH group in the incorporated nucleoside analogue prevents the formation of the 5' to 3' phosphodiester linkage essential for DNA chain elongation, and therefore, the viral DNA growth is terminated. Lamivudine is administered orally, and it is rapidly absorbed with a bio-availability of over 80%. Some research suggests that lamivudine can cross the blood-brain barrier.

Entecavir, abbreviated ETV, is an oral antiviral drug used in the treatment of hepatitis B infection. It is marketed under the trade names Baraclude® (BMS) and Entaliv® (DRL).

Entecavir is a nucleoside analog (more specifically, a guanosine analogue) that inhibits reverse transcription and DNA replication thus preventing transcription in the viral replication process. The drug's manufacturer claims that entecavir is more efficacious than previous agents used to treat hepatitis B (lamivudine and adefovir). Entecavir was approved by the U.S. FDA in March 2005 and is used to treat chronic hepatitis B. It also helps prevent the hepatitis B virus from multiplying and infecting new liver cells. Entecavir is also indicated for the treatment of chronic hepatitis B in adults with HIV/AIDS infection. However, entecavir is not active against HIV.

Telbivudine is an antiviral drug used in the treatment of hepatitis B infection. It is marketed by Swiss pharmaceutical company Novartis under the trade names Sebivo® (Europe) and Tyzeka® (United States). Clinical trials have shown it to be significantly more effective than lamivudine or adefovir, and less likely to cause resistance. Telbivudine is a synthetic thymidine nucleoside analogue; it is the L-isomer of thymidine. It is taken once daily.

Tenofovir disoproxil fumarate (TDF or PMPA), marketed by Gilead Sciences under the trade name Viread®, it is also a nucleotide analogue reverse transcriptase inhibitor (nRTIs) which blocks the HBV reverse transcriptase, an enzyme crucial to viral production. Tenofovir disoproxil fumarate is a prodrug form of tenofovir. Tenofovir is indicated in combination with other antiretroviral agents for the treatment of HIV-1 infection in adults. This indication is based on analyses of plasma HIV-1 RNA levels and CD4 cell counts in controlled studies of tenofovir in treatment-naive and treatment-experienced adults. There are no study results demonstrating the effect of tenofovir on the clinical progression of HIV. It also has activity against wild-type and lamivudine-resistant HBV.

C. NUCLEOTIDYL TRANSFERASE SUPERFAMILY ENZYMES

The inhibitors screened in this project were selected for their ability to inhibit the HIV RNAse H and/or integrase enzymes (or to be close chemical analogs of known inhibitors). The RNAse H and integrase are members of the nucleotidyl transferase superfamily (NTS) whose members share a similar protein fold and enzymatic mechanisms (Yang 1995). Therefore, the presumed targets of the antiherpesvirus compounds claimed here are viral and/or cellular NTS enzymes. RNAse H enzymes (Hostomsky et al., 1993a; 1993b; 1993c) digest RNA when it is hybridized to DNA. Their physiological roles include removal of RNA primers during DNA synthesis, removal of abortive transcription products, and removal of RNA strands following reverse transcription by viruses or retrotransposons. Integrase enzymes cleave DNA strands and catalyze the covalent insertion of another DNA strand at the cleavage site. Consequently, the presumed mechanism of action for the herpesvirus inhibitors is through suppression of one or more of the nucleolytic or recombination-related activities essential for replication of the herpesvirus DNA.

The NTS family of enzymes includes *E. coli* RNase H I and II (Katayanagi et al., 1990, Yang et al., 1990 and Lai et al., 2000); human RNase H 1 and 2 (Lima et al., 2001, Frank et al., 1998 and Frank et al., 1998); the RuvC Holiday junction resolvase (Ariyoshi et al., 1994); and the Argonaute RNAse (Parker et al., 2004 and Song et al., 2004); retroviral RNase H enzymes including the HIV enzyme (Nowotny 2009); retroviral integrases including the HIV integrase (Dyda et al., 1994); and the hepatitis B virus (HBV) RNase H (Tavis et al., 2013). These enzymes function in a wide range of nucleic acid metabolic events, including RNA and DNA digestion, DNA recombination, DNA integration, DNA excision, replication fork repair, DNA repair, miRNA maturation, and miRNA-directed RNA cleavage. The canonical RNase H structure contains about 100 amino acids that fold into a 5-stranded β-sheet overlaid with 3 α-helices arranged like an "H". Within the active site are four conserved carboxylates (the "DEDD" motif) that coordinate two divalent cations (Nowotny et al., 2005).

The RNase H enzymatic mechanism is believed to involve both divalent cations (Klumpp et al., 2003; Yang and Steitz, 1995), although a 1-ion mechanism has been proposed (Goedken and Marqusee, 2001; Keck et al., 1998). There are three classes of RNAse Hs distinguished by how they bind to their substrates. RNA binding by the "stand-alone" class typified by E. coli RNAse H I is promoted by a basic "handle" region (Hostomsky et al., 1993; Kwun et al., 2001). Eukaryotic RNase Hs typically contain a "RHBD" domain that influences nucleic acid binding. Finally, substrate binding by the retroviral enzymes can either be a property of the RNase H domain itself (e.g., Moloney murine leukemia virus) or may require the reverse transcriptase domain to provide sufficient affinity for the nucleic acid substrate (e.g., HIV) (Hostomsky et al., 1993; Smith et al., 1994).

The HBV RNase H is a NTS enzyme. Mutational analysis of the HBV RNase H revealed the DEDD active site residues to be D702, E731, D750, and D790 (numbering for HBV strain adw2) (Gerelsaikhan et al., 1996; Tavis et al., 2013).

HIV reverse transcription requires a virally encoded RNase H activity to remove the viral RNA after it has been copied into DNA (Freed and Martin, 2007). Consequently, the HIV RNase H activity has attracted much attention as a drug target (Billamboz et al., 2011; Bokesch et al., 2008; Budihas et al., 2005; Chung et al., 2011; Chung et al., 2010; Di et al., 2010; Didierjean et al., 2005; Fuji et al., 2009; Himmel et al., 2009; Himmel et al., 2006; Kirschberg et al., 2009; Klarmann et al., 2002; Klumpp et al., 2003; Klumpp and Mirzadegan, 2006; Shaw-Reid et al., 2003; Su et al., 2010; Takada et al., 2007; Wendeler et al., 2008; Williams et al., 2010). Over 100 anti-HIV RNase H compounds, based on a wide variety of chemical scaffolds, have been reported (Chung et al., 2011; Klumpp and Mirzadegan, 2006). They typically have inhibitory concentration-50% ($IC_{50}$) values in the low µM range. The large majority of these compounds inhibit the RNase H by chelating divalent cations in the active site (Billamboz et al., 2011; Chung et al., 2011; Fuji et al., 2009; Himmel et al., 2009; Kirschberg et al., 2009; Su et al., 2010), but compounds that alter the enzyme's conformation or its interaction with nucleic acids have also been reported (Himmel et al., 2006; Wendeler et al., 2008). The inhibitors typically have $EC_{50}$ values~10× higher than the $IC_{50}$ values, and they often cause modest cytotoxicity, leading to therapeutic indexes (TI) that are usually <10. Second-generation inhibitors with substantially improved efficacy have been reported, (Billamboz et al., 2011; Chung et al., 2011; Williams et al., 2010), and compounds with efficacy and TI values appropriate for a human drug exist (Himmel et al., 2006; Williams et al., 2010).

None of the anti-HIV RNase H compounds have entered clinical trials yet. This is due in part to their relatively low TI values but also to the large number of approved and developmental anti-HIV drugs, raising doubts about the marketability of anti-HIV RNase H compounds. Despite these challenges, the HIV RNase H remains a target of intensive ongoing drug development, as is evidenced by the large number of groups working in the field (Billamboz et al., 2011; Bokesch et al., 2008; Budihas et al., 2005; Chung et al., 2011; Chung et al., 2010; Di et al., 2010; Didierjean et al., 2005; Fuji et al., 2009; Himmel et al., 2009; Himmel et al., 2006; Kirschberg et al., 2009; Klarmann et al., 2002; Klumpp et al., 2003; Klumpp and Mirzadegan, 2006; Shaw-Reid et al., 2003; Su et al., 2010; Takada et al., 2007; Wendeler et al., 2008; Williams et al., 2010).

Because both the RNase H and integrase are NTS enzymes, some anti-RNase H compounds can inhibit the HIV integrase, and some anti-integrase compounds can inhibit the RNase H (Klarmann et al., 2002, Williams et al., 2010; Billamboz et al., 2011). Despite this cross-inhibitory potential, resistance mutations to HIV DNA polymerase or integrase drugs have not led to cross-resistance to RNase H inhibitors (Billamboz et al., 2011 and Himmel et al., 2006).

HBV reverse transcription requires two viral enzymatic activities that are both located on the viral reverse transcriptase protein. The DNA polymerase activity synthesizes new DNA and is targeted by the nucleos(t)ide analogs. The RNase H destroys the viral RNA after it has been copied into DNA. Inhibiting the RNAse H would block DNA synthesis and consequently halt viral replication, but anti-HBV RNase H drugs have not been developed because enzyme suitable for drug screening could not be readily made. One of the inventors recently produced active recombinant HBV RNase H and identified 21 inhibitors of the RNase H (Table 1; Tavis et al., 2013; Hu et al., 2013).

These examples of cross-inhibition of NTS enzymes by RNase H and integrase inhibitors provide the precedent upon which these studies with the herpesviruses rest and they directly led to the studies on HBV inhibition.

D. CHEMICAL ENTITY

1. Chemical Genus and Species

The compounds of the present disclosure appears to inhibit a different enzymatic activity than the existing anti-herpesvirus drugs, and does so with a striking capacity to suppress virus replication at very low toxicity to uninfected cells. This implies that they may be effective against viral isolates resistant to the existing drugs and suggests that these drugs could be combined effectively with the existing drugs to both increase efficacy and to reduce the rate of resistance development to either drug. Furthermore, the compounds were more effective than a currently accepted first line therapy, acyclovir, indicating that it may be more effective than the existing drugs when formulated for pharmaceutical delivery. These compounds may be used to treat acyclovir resistant viral mutants. In other embodiment, these compounds work against HBV by inhibiting the viral RNase H, which is a new mechanism of inhibition for HBV. As they directly bind to the viral RNaseH active site which is physically distinct from the HBV DNA polymerase active site targeted by the anti-HBV nucleos(t)ide analogs, they may be used to treat nucleos(t)ide analog-resistant HBV mutants.

The compound of the present disclosure is represented by the formula below:

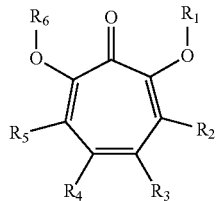
(I)

wherein:

R$_1$ and R$_6$ are each independently selected from hydrogen, alkyl$_{(C\leq 8)}$, substituted alkyl$_{(C\leq 8)}$, acyl$_{(C\leq 8)}$, or substituted acyl$_{(C\leq 8)}$;

R$_2$ and R$_5$ are each independently selected from hydrogen, hydroxy, alkyl$_{(C\leq 8)}$, substituted alkyl$_{(C\leq 8)}$, cycloalkyl$_{(C\leq 12)}$, substituted cycloalkyl$_{(C\leq 12)}$, aryl$_{(C\leq 8)}$, substituted aryl$_{(C\leq 8)}$, heteroaryl$_{(C\leq 8)}$, substituted heteroaryl$_{(C\leq 8)}$, alkoxy$_{(C\leq 8)}$, substituted alkoxy$_{(C\leq 8)}$, acyl$_{(C\leq 8)}$, or substituted acyl$_{(C\leq 8)}$; and R$_3$ and R$_4$ are each independently selected from hydrogen, hydroxy, alkyl$_{(C\leq 12)}$, substituted alkyl$_{(C\leq 12)}$, cycloalkyl$_{(C\leq 12)}$, substituted cycloalkyl$_{(C\leq 12)}$, aryl$_{(C\leq 18)}$, substituted aryl$_{(C\leq 18)}$, heteroaryl$_{(C\leq 12)}$, substituted heteroaryl$_{(C\leq 12)}$, acyl$_{(C\leq 12)}$, substituted acyl$_{(C\leq 12)}$, or —C(O)R$_a$, wherein:

R$_a$ is alkyl$_{(C\leq 8)}$, cycloalkyl$_{(C\leq 18)}$, aryl$_{(C\leq 18)}$, heteroaryl$_{(C\leq 18)}$, alkoxy$_{(C\leq 12)}$, aryloxy$_{(C\leq 18)}$, -alkanediyl$_{(C\leq 6)}$-cycloalkyl$_{(C\leq 12)}$; or a substituted version of any of these groups; or R$_3$ and R$_4$ are taken together and are a group of the formula:

—(CH$_2$)$_m$C(O)A(CH$_2$)$_n$—, wherein:

A is O or NR$_b$, wherein:

R$_b$ is hydrogen, alkyl$_{(C\leq 6)}$, or substituted alkyl$_{(C\leq 6)}$; and m and n are each independently selected from 0, 1, 2, or 3;

or a pharmaceutically acceptable salt or tautomer thereof.

TABLE 1

Exemplary Compounds of the Present Disclosure

| Compound Number | Compound |
|---|---|
| 106 | |
| 107 | |
| 108 | |
| 109 | |
| 110 | |
| 111 | |
| 112 | |

TABLE 1-continued
Exemplary Compounds of the Present Disclosure
| Compound Number | Compound |
|---|---|
| 113 | 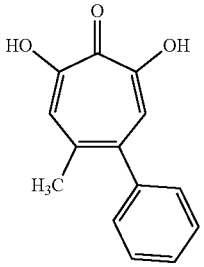 [SMILES: Cc1cc(O)c(=O)c(O)cc1-c1ccccc1] |
| 114 | 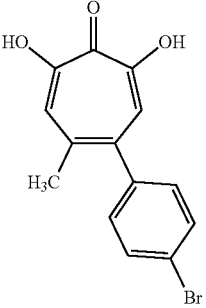 [SMILES: Cc1cc(O)c(=O)c(O)cc1-c1ccc(Br)cc1] |
| 115 | 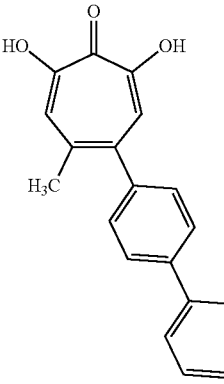 |
| 117 | 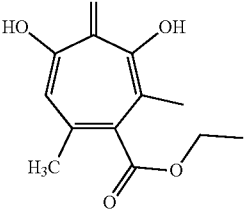 |
| 118 (Also 254) | 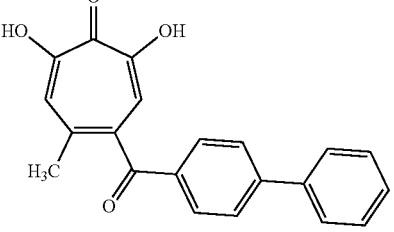 |
| 119 | 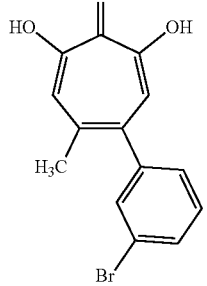 |
| 120 | 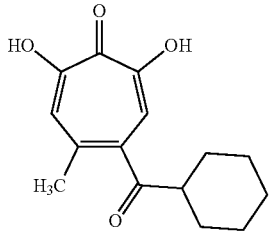 [SMILES: Cc1cc(O)c(=O)c(O)cc1C(=O)C1CCCCC1] |
| 143 | 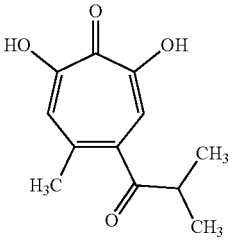 [SMILES: Cc1cc(O)c(=O)c(O)cc1C(=O)C(C)C] |
| 144 | 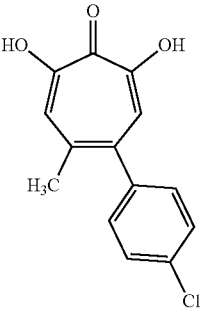 [SMILES: Cc1cc(O)c(=O)c(O)cc1-c1ccc(Cl)cc1] |
| 145 | 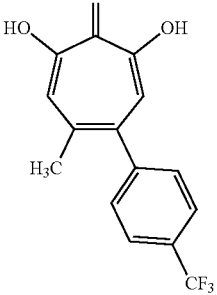 |

TABLE 1-continued

Exemplary Compounds of the Present Disclosure

| Compound Number | Compound |
|---|---|
| 146 | |
| 147 | |
| 172 | |
| 173 | |
| 195 | |
| 196 (Also 268) | |
| 210 | |
| 231 | |
| 232 | |
| 233 | |

TABLE 1-continued

Exemplary Compounds of the Present Disclosure

| Compound Number | Compound |
|---|---|
| 234 | |
| 235 | |
| 255 | |
| 256 | |
| 257 | |
| 258 | |
| 259 | |
| 260 | |
| 261 | |
| 262 | |

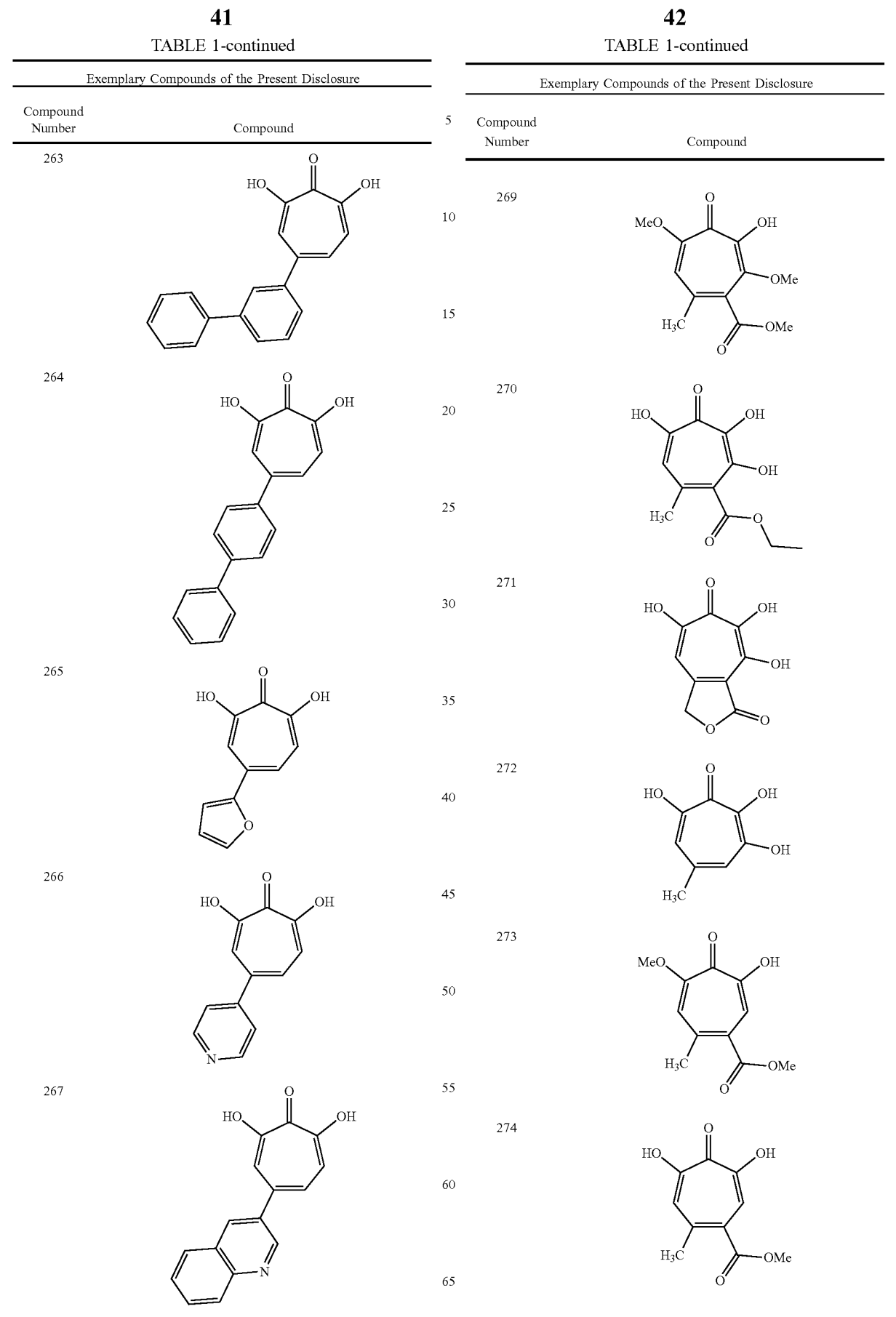

TABLE 1-continued

Exemplary Compounds of the Present Disclosure

| Compound Number | Compound |
|---|---|
| 263 | 2,7-dihydroxy-4-(3-phenylphenyl)cyclohepta-2,4,6-trien-1-one |
| 264 | 2,7-dihydroxy-4-(4-phenylphenyl)cyclohepta-2,4,6-trien-1-one |
| 265 | 2,7-dihydroxy-4-(furan-2-yl)cyclohepta-2,4,6-trien-1-one |
| 266 | 2,7-dihydroxy-4-(pyridin-4-yl)cyclohepta-2,4,6-trien-1-one |
| 267 | 2,7-dihydroxy-4-(quinolin-3-yl)cyclohepta-2,4,6-trien-1-one |
| 269 | methyl 2,3-dimethoxy-7-hydroxy-5-methyl-6-oxocyclohepta-1,3,5-triene-1-carboxylate |
| 270 | ethyl 2,6,7-trihydroxy-4-methyl-3-oxocyclohepta-1,4,6-triene-5-carboxylate (approx.) |
| 271 | trihydroxy furo-fused tropone lactone |
| 272 | 2,7-dihydroxy-4-methyl-... cycloheptatrienone |
| 273 | methyl 3-methoxy-2,7-dihydroxy-5-methyl-6-oxocyclohepta-1,3,5-triene-1-carboxylate |
| 274 | methyl 2,7-dihydroxy-4-methyl-3-oxocyclohepta-1,4,6-triene-5-carboxylate |

TABLE 1-continued

Exemplary Compounds of the Present Disclosure

| Compound Number | Compound |
|---|---|
| 280 | 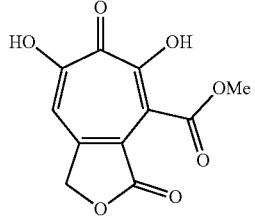 [SMILES: COC(=O)c1c2c(cc(O)c(=O)c1O)COC2=O] |

The compounds of the present disclosure may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

2. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; "hydroxylsulfonyl" means —SO$_2$OH; "aminosulfonyl" means —SO$_2$NH$_2$ and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol " ≡≡≡ " represents a single bond or a double bond. Thus, for example, the formula

includes

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫼⫼⫼" means a single bond where the group attached to the thick end of the wedge is "into the page". The symbol "⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

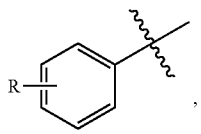

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

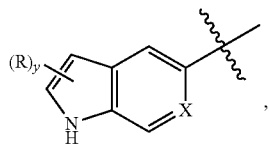

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and compound classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. Compare with "alkoxy$_{(C\leq 10)}$", which designates alkoxy groups having from 1 to 10 carbon atoms. Also compare "phosphine$_{(C\leq 10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning. Thus, the terms "C5 olefin", "C5-olefin", "olefin$_{(C5)}$", and "olefin$_{C5}$" are all synonymous. When any group or compound class below is used with the term "substituted", any carbon atoms of the chemical group replacing the hydrogen atom do not count towards the total carbon atom limit for that group or compound class.

The term "saturated" when used to modify a compound or an atom means the compound or atom has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

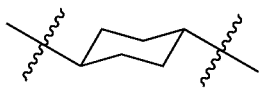 [SMILES: *C1CCC(*)CC1]

is a non-limiting example of cycloalkanediyl group. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

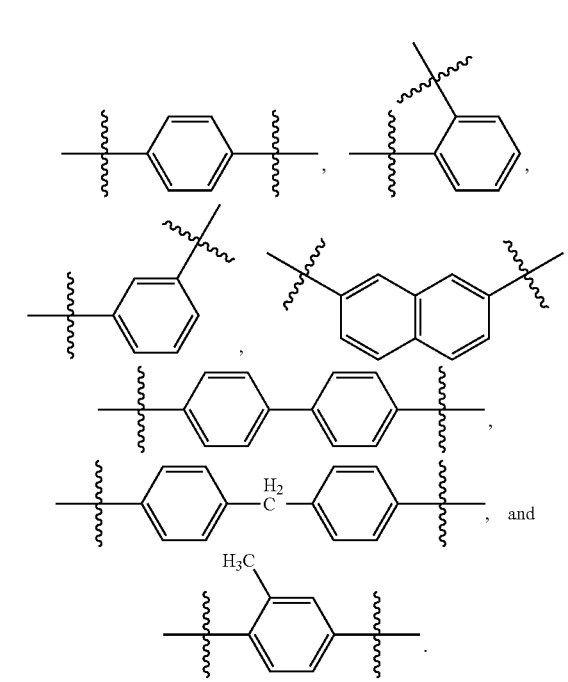

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_2OH$, or —$S(O)_2NH_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —$C(O)CH_3$ (acetyl, Ac), —$C(O)CH_2CH_3$, —$C(O)CH_2CH_2CH_3$, —$C(O)CH(CH_3)_2$, —$C(O)CH(CH_2)_2$, —$C(O)C_6H_5$, —$C(O)C_6H_4CH_3$, —$C(O)CH_2C_6H_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_{20}H$, or —$S(O)_2NH_2$. The groups, —$C(O)CH_2CF_3$, —$CO_2H$ (carboxyl), —$CO_2CH_3$ (methylcarboxyl), —$CO_2CH_2CH_3$, —$C(O)NH_2$ (carbamoyl), and —$CON(CH_3)_2$, are non-limiting examples of substituted acyl groups.

The term "alkoxy" when used without the "substituted" modifier refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —$OCH(CH_3)_2$ (isopropoxy), —$OC(CH_3)_3$ (tert-butoxy), —$OCH(CH_2)_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$NHCH_3$, —$NHCH_2CH_3$, —$N(CH_3)_2$, —$C(O)NH_2$, —$C(O)NHCH_3$, —$C(O)N(CH_3)_2$, —$OC(O)CH_3$, —$NHC(O)CH_3$, —$S(O)_{20}H$, or —$S(O)_2NH_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects, or +/−5% of the stated value.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living vertebrate organism, such as a human, monkey, cow, sheep, goat, dog, cat, mouse, rat, guinea pig, bird, fish or transgenic species thereof. In certain embodiments, the patient or subject is a primate. Non-limiting examples of human subjects are adults, juveniles, infants and fetuses.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of the compound of the present disclosure which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease, including reactivation.

"Prodrug" means a compound that is convertible in vivo metabolically into an inhibitor according to the present disclosure. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Effective amount," "therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease. In some embodiments, treatment of a patient afflicted with one of the pathological conditions described herein comprises administering to such a patient an amount of compound described herein which is therapeutically effective in controlling the condition or in prolonging the survivability of the patient beyond that expected in the absence of such treatment. As used herein, the term "inhibition" of the condition also refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

E. THERAPEUTIC METHODS

1. Pharmaceutical Formulations

In particular embodiments, where clinical application of an active ingredient is undertaken, it will be necessary to prepare a pharmaceutical composition appropriate for the intended application. Generally, this will entail preparing a pharmaceutical composition that is essentially free of pyrogens, as well as any other impurities or contaminants that could be harmful to humans or animals. One also will generally desire to employ appropriate buffers to render the complex stable and allow for uptake by target cells.

Aqueous compositions of the present disclosure comprise an effective amount of the active compound, as discussed above, further dispersed in pharmaceutically acceptable carrier or aqueous medium. Such compositions also are referred to as inocula. The phrase "pharmaceutically or pharmacologically acceptable" refers to compositions that do not produce an adverse, allergic or other untoward reaction when administered to an animal, or a human, as appropriate, as well as the requisite sterility for in vivo uses.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present disclosure are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, a controlled release patch, salve or spray. In some embodiments, the topical formulation by used for administration to the skin, to mucosa membranes such as the eye, the eye lids, the genitals, the anus, or the inside of the mouth or nose, or in particular to the cornea.

An effective amount of the therapeutic composition is determined based on the intended goal. The term "unit dose" or "dosage" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment and the potency, stability and toxicity of the particular therapeutic substance.

2. Routes of Administration

Formulations of the present disclosure are suitable for oral administration. However, the therapeutic compositions of the present disclosure may be administered via any common route so long as the target tissue is available via that route. This includes ocular, nasal, buccal, corneal, rectal, vaginal, or topical administration, and intradermal, subcutaneous, intramuscular, intraperitoneal or intravenous injection. As such, compositions would be formulated pharmaceutically in route-acceptable compositions that include physiologically acceptable carriers, buffers or other excipients.

As with dosing amounts, the timing of delivery (including intervals and total number of doses) depends on the judgment of the practitioner and are peculiar to each individual. Factors affecting dose include physical and clinical state of the patient, the route of administration, the intended goal of treatment and the potency, stability and toxicity of the particular therapeutic substance.

3. Combination Therapy

In many clinical situations, it is advisable to use a combination of distinct therapies. Thus, it is envisioned that, in addition to the therapies described above, one would also wish to provide to the patient more "traditional" pharmaceutical herpesvirus or hepatitis B therapies. Examples of standard therapies are described above. Combinations may be achieved by administering a single composition or pharmacological formulation that includes both agents, or with two distinct compositions or formulations, at the same time, wherein one composition includes the agents of the present disclosure and the other includes the standard therapy. Alternatively, standard therapy may precede or follow the present agent treatment by intervals ranging from minutes to weeks to months. In embodiments where the treatments are applied separately, one would generally ensure that a significant period of time did not expire between the time of each delivery, such that the agents would still be able to exert an advantageously combined effect on the subject. In such instances, it is contemplated that one would administer both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the agent of the present disclosure, or the standard therapy will be desired. Various combinations may be employed, where the present disclosure compound is "A" and the standard therapy is "B," as exemplified below:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated as well. Drugs suitable for such combinations are described above and include, but are not limited to, herpesvirus DNA polymerase inhibitors (nucleoside analogs), including acyclovir, famciclovir, valaciclovir, penciclovir, and ganciclovir. Additionally, it is contemplated that other antiviral agents such as a pegylated interferon, interferon alfa-2b, lamivudine, adefovir, telbivudine, entercavir, or tenofovir may be used in combination with the compounds described herein.

F. EXAMPLES

The following examples are included to further illustrate various aspects of the disclosure. It should be appreciated by those of skill in the art that the techniques disclosed in the examples which follow represent techniques and/or compositions discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

1. Materials and Methods

Cells and Viruses.

Figure 3:
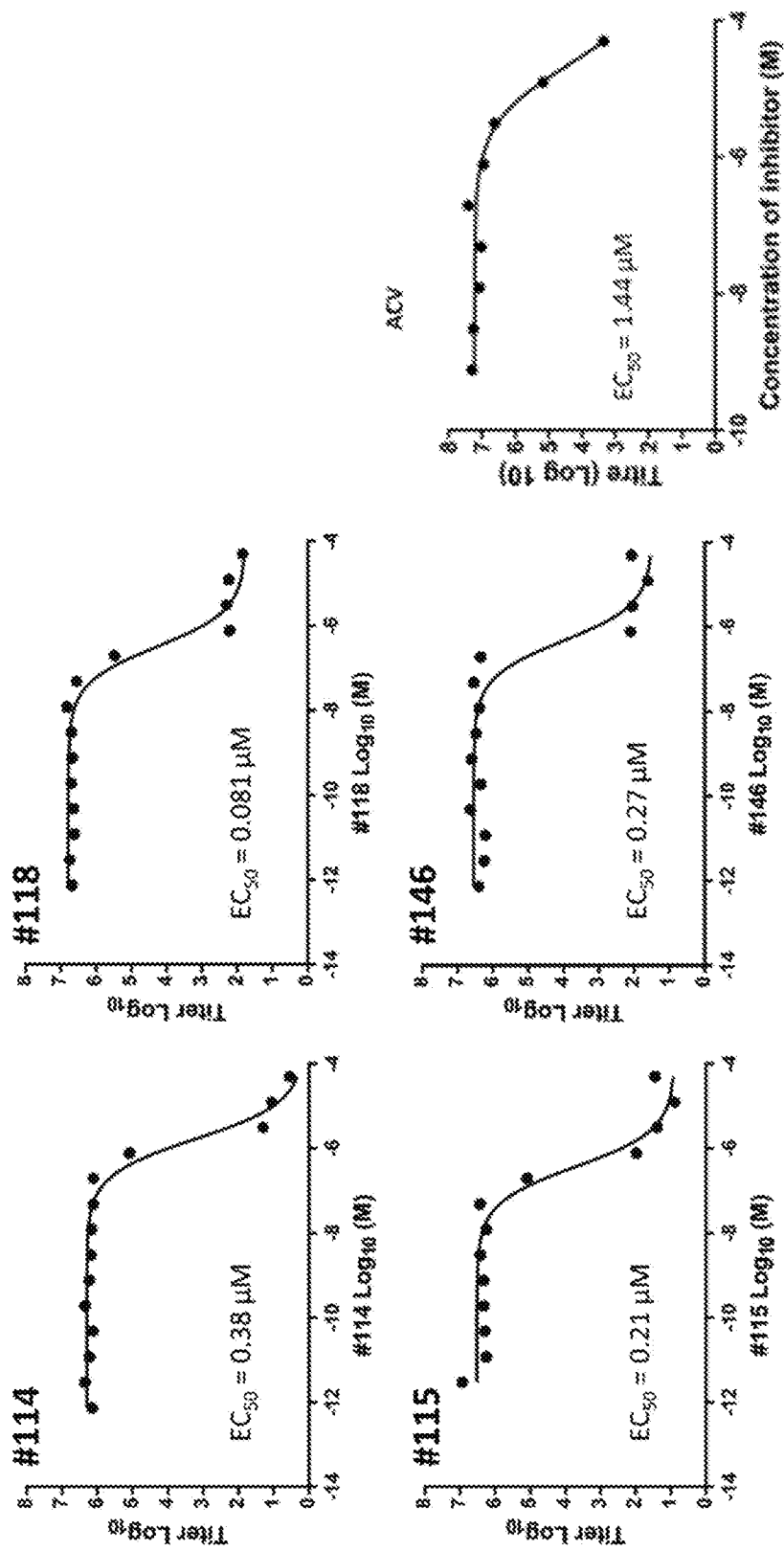
FIG. 3. $EC_{50}$ values against HSV-2 for select herpesvirus inhibitors. Serially diluted compounds were added to Vero cells simultaneously with HSV-1 or HSV-2 infection at moi of 0.1, and infectious virus titers in the cultures at 24 hours post-infection were determined by plaque assay. Effective concentration 50 ($EC_{50}$) values were determined by non-linear curve-fitting. The curves are for representative experiments and the $EC_{50}$ values are from one experiment per compound, each done in duplicate. The approved anti-herpes virus drug, ACV, was included for comparison purposes.

Vero cells were maintained in Dulbecco's modified Eagle's medium (DMEM) containing 3% newborn calf serum, 3% bovine growth serum, 2 mM L-glutamine and 100 IU/mL penicillin and 0.1 mg/mL streptomycin (P/S). HSV-1 #6 and HSV-2 #1 are de-identified clinical isolates from the Saint Louis University Hospital. Stocks were prepared after a single passage in cell culture and were titered by standard plaque assay (Knipe and Spang, 1982). Wild-type HSV-2 used in FIG. 3 was laboratory strain 333. The TK-deficient mutant of HSV-2 strain 333, ΔTK-, contains a 180-bp KpnI-KpnI deletion in the UL23 open reading frame that abrogates TK activity (McDermott, et al, 1984). ΔTK- was the generous gift of Jim Smiley. Virus stocks were grown and titered on Vero cells (Morrison and Knipe, 1996).

Anti-HSV-1 and -HSV-2 Replication Assay.

Compounds to be screened were diluted in PBS supplemented to contain 2% newborn calf serum and 1% glutamine, and added in 100 μL volume to confluent cell monolayers in 24-well cluster plates. Immediately thereafter HSV-1 and HSV-2, diluted in the supplemented PBS medium, were added to the wells in 50 μl volume such that the final concentration of compound was 50 μM and 5 μM and the multiplicity of infection was 0.1. The plates were incubated at 37° C. for 1 hour and then virus-containing inoculum was removed and the wells were washed once in PBS. Compounds, diluted to 50 μM and 5 μM in DMEM supplemented to contain 2% newborn calf serum and 1% each penicillin/streptomycin, were added at 0.5 mL/well. Plates were incubated at 37° C. an additional 23 hr, and then the plates were visually inspected through a phase contrast microscope for cytopathic effect, and for toxic effect. Only those wells in which the cell monolayer was substantially healthier than the DMSO-treated control wells were harvested, and also a sampling of additional wells which showed cytopathic effect. The entire contents of each well were collected by scraping. Samples were frozen at −80° C., and then subsequently thawed, sonicated, and infectious virus titer was determined by standard plaque assay on Vero cell monolayers. Because the compounds were dissolved at 10 mM in 100% DMSO, equivalent dilutions of DMSO were added to additional wells as a control for effects of the diluent. Each experiment was repeated once. $EC_{50}$ values were determined as above except that serial dilutions of the compound to be tested were prepared starting at 50 μM. The inhibitory values were calculated by non-linear curve-fitting in GraphPad Prism.

Toxicity Assays.

Qualitative assessments of cytotoxicity were done visually by inspecting the cells in the primary screening assays. For the quantitative assays, cells were plated in 96-well plates at $1.0 \times 10^4$ per well. The next day the compounds were added at 0.78 to 100 μM in a final concentration of 1% (v/v) DMSO, and the cells were incubated for 24 hours under conditions identical to those employed for the viral replication inhibition assays. Mitochondrial toxicity was measured by incubating the cells with 0.25 mg/mL thiazolyl blue tetrazolium bromide (MTT, Sigma Aldrich Chemical Co.), the cultures were incubated for 60 min, metabolites were solubilized in acidic isopropanol, and absorbance was read at 570 nm. $CC_{50}$ values were calculated by non-linear curve fitting using GraphPad Prism.

Mouse Liver Microsome Assays.

Microsomal incubations are run at a final P450 concentration of 0.25 μM. The microsomal mixture is composed of 0.1M potassium phosphate containing 3.3 mM MgCl and 1 μM compound (final concentration). The mixture is pre-warmed for 5 min at 37° C. To initiate the reaction a 12 mM stock of NAPDH (1.2 mM, final concentration) is added to the warmed microsomal mixture and aliquots are removed at 0, 5, 10, 20 and 30 min. Samples are quenched with ice cold acetonitrile containing internal standard and either 1.8 mM EDTA or EGTA (final concentration). Samples are vortexed and spun down at 3200 rpm for 5 min. The supernant is transferred to 96-deep well plates and run on LC/MS/MS.

Biochemical Inhibition of HBV RNaseH and Human RNaseH1 Activity.

Compounds were tested for activity against the HBV RNaseH and human RNaseH1 in vitro as previously described (Tavis, et al., 2013; Hu, et al., 2013) Briefly, recombinant hexahistidine-tagged enzymes were expressed in E. coli and partially purified by nickel affinity chromatography. RNaseH activity was measured using an oligonucleotide-directed RNA cleavage assay in which a DNA oligonucleotide is annealed to an internally $^{32}$P-labeled RNA, the RNA:DNA heteroduplex is incubated with the enzyme to permit cleavage, and then the RNA cleavage products are resolved by electrophoresis and detected by autoradiography. The compounds were included in the reaction mixes at 60, 20, or 10 μM and the amount of the RNA cleavage products in the compound-containing reactions was compared to reactions in which an equivalent concentration of DMSO was added as a vehicle control. The data were quantified using ImageJ.

HBV replication assay. Inhibition of HBV replication was measured in HepDES19 cells as previously described (Cai, et al., 2014). Cells were seeded into 6-well plates and incubated in DMEM/F12, 10% fetal bovine serum (FBS), 1% penicillin/streptomycin (P/S) with 1 μg/ml tetracycline. Tetracycline was withdrawn after 24 hours. The test compound was applied to duplicate wells 48 hours later in medium containing a final DMSO concentration of 1%, and medium containing the compound was refreshed daily for the following two days. Cells were harvested and nonencapsidated nucleic acids were digested with micrococcal nuclease (New England Biolabs). HBV DNA was purified from capsids using QIAamp Cador Pathogen Mini Kit (Qiagen) with proteinase K incubation overnight at 37° C. TaqMan PCR was performed for 40 cycles at an annealing temperature of 60° C. Primers and probe (IDT Inc.) for the plus-polarity strand were: 5'CATGAACAAGAGATGATT-AGGCAGAG3' (SEQ ID NO: 1); 5'GGAGGCTGTAGG-CATAAATTGG3' (SEQ ID NO: 2); 5'/56-FAM/CTGCGCACC/ZEN/AGCACCATGCA/3IABkFQ (SEQ ID NO: 3). Primers and probe for the minus-polarity strand were: 5'GCAGATGAGAAGGCACAGA3' (SEQ ID NO: 4); 5'CTTCTCCGTCTGCCGTT3' (SEQ ID NO: 5); 5'/56-FAM/AGTCCGCGT/ZEN/AAAGAGAGGTGCG/3IABkFQ (SEQ ID NO: 6).

2. Activity Against Herpes Simplex

Compound Selection Strategy.

Hydroxylated tropolone compounds were synthesized and evaluated for their ability to inhibit HSV-1 and HSV-2 replication based on one or more of the following criteria:
Ability to inhibit the HBV RNase H; or
Close chemical relatives of compounds that inhibit the HBV RNase H Compounds were selected for screening against the HBV RNase H based on their ability to inhibit the HIV RNase H and/or integrase, or due to being close chemical relatives of such compounds.

Twenty one α-hydroxylated tropolones were tested for binding to the pUL15C terminase (Masaoka et al., 2016). Ten of these interacted strongly with the terminase complex and disrupt its nuclease activity with sub-micromolar $IC_{50}$ values, and at least four of the 10 compounds (#111, 46, 120, 143) strongly suppress HSV-1 and HSV-2 replication in cell culture at 5 μM or less (Tavis et al., 2014; Ireland et al., 2016).

Primary Screening for Inhibition of HSV-1 and HSV-2 Replication.

Efficacy of 23 compounds against both HSV-1 and HSV-2 was initially assessed at 50 and 5 μM in a semi-quantitative replication inhibition assay. Inhibition was categorized as negligible (<1 $log_{10}$ at 50 μM relative to the DMSO-treated control), intermediate (1 to 3 $log_{10}$ suppression, which equals 10- to 1,000-fold reduction), or strong (3 to 6 $log_{10}$ suppression, or 1,000- to 1,000,000-fold reduction). Negligible activity at 50 μM was observed for 3 of the compounds (12%) against HSV-1 or HSV-2 (Table 1). At 5 μM, 11 of the compounds (48%) had negligible activity against HSV-1 or HSV-2 (Table 1). Intermediate suppression was observed for one compound (4%) against HSV-1 and two compounds (9%) against HSV-2 at 5 μM. Strong inhibition was observed for 19 compounds (86%) against HSV-1 and HSV-2 at 50 μM. Importantly, strong inhibition against HSV-1 was found for 12 compounds (52%) and against HSV-2 for 11 compounds (48%) even as low as 5 μM (Table 1). The strongest antagonist of both HSV-1 and HSV-2 was compound #146, which inhibited HSV-1 by 5.68 $log_{10}$ (478,600-fold) and HSV-2 by 5.66 $log_{10}$ (457,100-fold) at 5 μM. For comparison, the approved anti-HSV drug acyclovir inhibited HSV-1 replication in this assay by 4.22 $log_{10}$ (16,600-fold) and HSV-2 by 3.6 $log_{10}$ (3,980-fold) at 5 μM. Therefore, this screen of 23 hydroxylated tropolone compounds led to identification of nine compounds with comparable or better inhibition than acyclovir against both HSV-1 and HSV-2. This "hit" rate implies that this group of compounds has structural features that are useful for targeted inhibition of HSV-1 and HSV-2.

Figure 2:
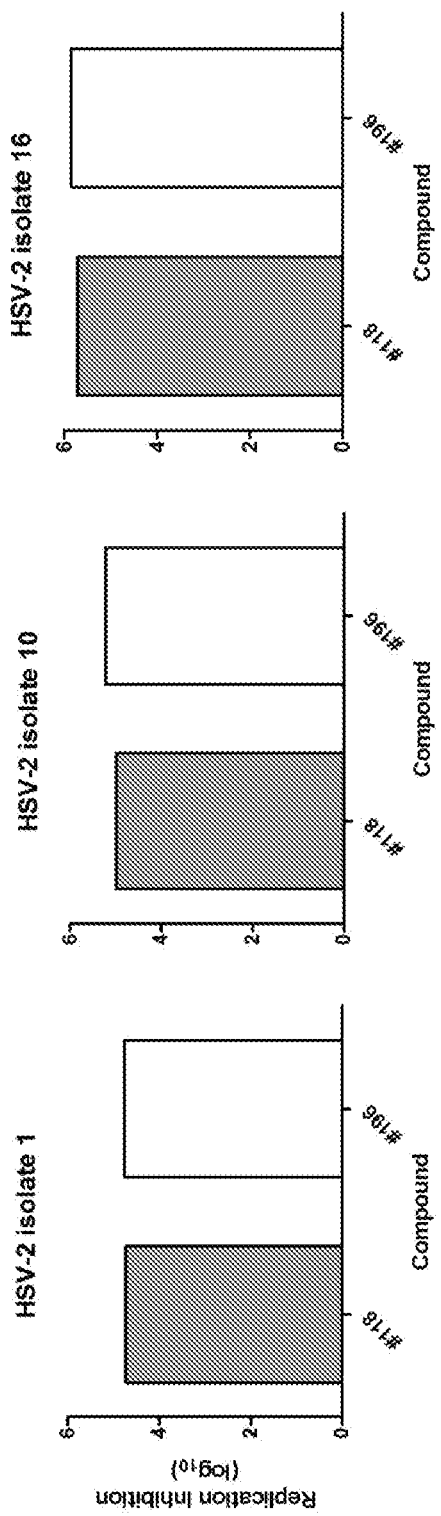
FIG. 2. αHT compounds inhibit HSV-2 primary clinical isolates. Vero cell monolayers were infected with the indicated patient isolate at moi of 0.1 in the presence of αHT inhibitors #115, 118 or 196 or DMSO control at 5 µM. Cultures were collected 24 hours post-infection and infectious virus titers were determined by plaque assay. Titers in compound-treated samples were subtracted from DMSO-treated samples. Values are the averages of duplicate cultures.

Two compounds (#118 and #196) were capable of suppressing replication of three primary clinical isolates of HSV-2 by >4.7 $log_{10}$ at 5 μM (FIG. 2), indicating that they are active against a range of clinically relevant virus strains. $EC_{50}$ values for αHT compounds tested ranged from 450 nM down to 130 nM against HSV-1, and 130 nM down to 80 nM against HSV-2 (Table 1). For comparison, the $EC_{50}$ for ACV against HSV-1 is 160 nM, and against HSV-2 is 1.44 μM.

Overall, the compounds that were active against HSV-1 had similar levels of inhibitory activity against HSV-2 (Table 2). This shared inhibitory pattern against the herpesviruses was different from the ability of the same compounds to inhibit the activity of the HBV RNase H enzyme (Table 2). Without wishing to be bound by any theory, it is believed that the structure-activity relationships (SARs) for inhibition of the various herpesviruses are likely to be more similar to each other than to SARs for inhibition of NTS enzymes from different viral families.

TABLE 2

HSV Suppression by Hydroxylated Tropolone Compounds

| | | HSV-1 | | | HSV-2 | | | | | | Vero cell toxicity | |
|---|---|---|---|---|---|---|---|---|---|---|---|---|
| | | Log suppression | | | Log suppression | | | | Anti- | | | |
| Number | Name | 50 μM | 5 μM | 1.5 μM | EC50 (μM) | 50 μM | 5 μM | 1.5 μM | EC50 (μM) | Anti-HBV | Human RNAseH1 | Qualitative | CC50 (μM) |
| Hydroxylated Tropolones | | | | | | | | | | | | |
| 106 | CM1012-6a | 4.11 | −0.07 | | | 2.87 | −0.55 | | | +++ | +++ | | |
| 108 | CM1012-6c | + | 0.00 | | | + | 0.00 | | | + | ++ | | |
| 109 | CM1012-6d | 3.99 | 0.21 | | | 4.15 | −0.22 | | | + | ++ | t | |
| 110 | CM1012-6e | 5.11 | −0.47 | | | 4.24 | −0.65 | | | + | +++ | t? | |
| 111 | CM1012-6f | T | 4.28 | | | T | 3.21 | | | − | +++ | T | >50 |
| 112 | CM1012-6i | 5.25 | 0.02 | | | 3.20 | −0.40 | | | ++ | +++ | | |
| 113 | RM-YM-1-0613 | 5.38 | 2.27 | | | 5.61 | 2.07 | | | ++ | ++ | | >100 |
| 114 | RM-YM-2-0613 | 4.75 | 4.80 | | | 5.26 | 3.92 | | | − | ++ | | >100 |
| 115 | RM-YM-3-0613 | 4.14 | 4.26 | 0.13 | | 5.11 | 4.52 | 0.13 | | − | − | | >100 |
| 117 | RM-CM-2-0613 | 4.66 | 0.76 | | | 4.97 | −0.16 | | | − | − | t? | |
| 118 | RM-MD-2-0813 | 6.27 | 5.14 | 0.085 | | 5.56 | 3.22 | 0.08 | | − | − | | >100 |
| 119 | RM-YM-3BrPh | 5.28 | 5.19 | | | 4.88 | 5.02 | | | − | − | | 72.37 |
| 120 | RM-MD-1-0713 | 5.53 | 4.84 | | | 5.07 | 5.41 | | | + | +++ | | ~50 |
| 141 | B2-10-1-8 | − | − | | | − | − | | | − | − | | |
| 142 | B26117 | − | − | | | − | − | | | − | − | | |
| 143 | MD-1-138 | 5.93 | 0.25 | | | 4.78 | 0.00 | | | + | + | | |

TABLE 2-continued

HSV Suppression by Hydroxylated Tropolone Compounds

| Number | Name | HSV-1 Log suppression 50 µM | 5 µM | 1.5 µM | EC50 (µM) | HSV-2 Log suppression 50 µM | 5 µM | 1.5 µM | EC$_{50}$ (µM) | Anti-HBV | Anti-Human RNAseH1 | Vero cell toxicity Qualitative | CC$_{50}$ (µM) |
|---|---|---|---|---|---|---|---|---|---|---|---|---|---|
| 144 | DH-1-148 | 3.83 | −0.34 | | | 5.18 | 0.65 | | | − | − | | |
| 145 | DH-1-163 | 3.97 | 3.96 | | | 4.33 | 4.05 | | | − | − | | >100 |
| 146 | DH-2-8 | 6.20 | 5.68 | | 0.45 | 5.29 | 5.66 | | | − | +++ | | >100 |
| 147 | DH-2-4 | 5.81 | 5.92 | | | 4.12 | 4.33 | | | − | − | | 74.78 |
| 172 | 7-HT | 4.11 | 3.31 | | | 4.64 | 1.80 | | | − | ++ | | >100 |
| 173 | MD-1-152 | 5.80 | 5.91 | | | 5.94 | 5.32 | | | − | ++ | | >100 |
| 195 | purpurogallin | 0.20 | 0.17 | | | 0.11 | −0.04 | | | − | | | |
| 196 | DH-3-37 | 3.99 | 4.17 | 3.82 | 0.10 | 4.56 | 4.05 | | 2.57 | − | ++ | t | >100 |
| 210 | | 4.56 | 4.32 | | | 5.55 | 4.04 | | | | | | |
| 231 | | | | | | | | | | | | | |
| 232 | | + | + | | | + | + | | | | | | |
| 233 | | + | + | 2.63 | | + | + | | | | | | |
| 234 | | + | + | 2.71 | | + | + | | | | | | |
| 235 | | + | + | | | + | + | | | | | | |
| 255 | | + | + | 5.02 | | + | + | | | | | | |
| 256 | | + | + | 5.18 | | + | + | | | | | | |
| 257 | | + | + | 4.82 | | + | + | | | | | | |
| 258 | | + | + | 5.04 | | + | + | | | | | | |
| 259 | | + | + | 5.05 | | + | + | | | | | | |
| 260 | | + | − | 0.50 | | + | − | | | | | | |
| 261 | | + | − | − | | | | | | | | | |
| 262 | | + | + | + | | | | | | | | | |
| 263 | | + | + | + | | | | | | | | | |
| 264 | | + | + | + | | | | | | | | | |
| 265 | | + | + | + | | | | | | | | | |
| 266 | | + | − | − | | | | | | | | | |
| 267 | | + | + | − | | | | | | | | | |
| 269 | | 3.76 | 1.48 | 0.24 | | 4.67 | − | 4.04 | | | | | |
| 270 | | 6.47 | 5.97 | | | 6.90 | 6.32 | | | | | | |
| 271 | | 1.87 | 0.47 | 0.21 | | 2.94 | 1.53 | | | | | | |
| 273 | | 6.05 | 5.75 | 2.12 | | 6.90 | 6.32 | | | | | | |
| 274 | | + | − | 0.59 | | + | − | | | | | | |
| Nucleos(t)ide Analogs | | | | | | | | | | | | | |
| ACV | Acyclovir | 5.39 | 3.61 | | 0.16 | 4.73 | 2.88 | | 1.44 | − | − | | >100 |
| CDV | Cidofovir | 2.67 | 0.77 | | | 1.19 | 0.38 | | | | − | | |

Compound Toxicity.

Compound toxicity was measured both subjectively and quantitatively. Subjective assessments were done by visually inspecting the infected cells at the end of the 24 h infection window through a phase-contrast microscope. Only those wells in which the cell monolayer had substantially less cytopathic effect (CPE) than the DMSO-treated control wells, and in which the uninfected cells had a normal appearance were harvested for determination of HSV titers. This indicates that all compounds for which numerical viral replication data were obtained were less toxic than uninhibited HSV replication under these conditions.

Quantitative toxicity measurements were conducted for all compounds that suppressed HSV replication by >2 log$_{10}$ at 5 µM plus a number of compounds with lesser inhibitory activity for comparison. Toxicity was assessed by measuring release of intracellular proteases into the culture medium due to cellular lysis. Cells were plated in 96-well plates at $1.0 \times 10^4$ per well. The next day compound was added in concentrations ranging from 0.78 to 100 µM in a final concentration of 1% (v/v) DMSO. The cells were incubated for 24 h under conditions identical to those employed for the viral replication inhibition assays, and then mitochondrial activity was measured with the MTT assay (Sigma Aldrich) according to the manufacturer's instructions. Percent viability was determined for each compound concentration from the luminosity data, and then 50% cytotoxic concentrations (CC$_{50}$) values were calculated by non-linear curve fitting using GraphPad Prism. Consistent with the subjective assessments of toxicity, all compounds selected for quantitative toxicity assessment had CC$_{50}$ values≥50 µM under these conditions (Table 1).

Inhibition of Acyclovir-Resistant HSV-2 Mutants.

Figures 4A, 4B:
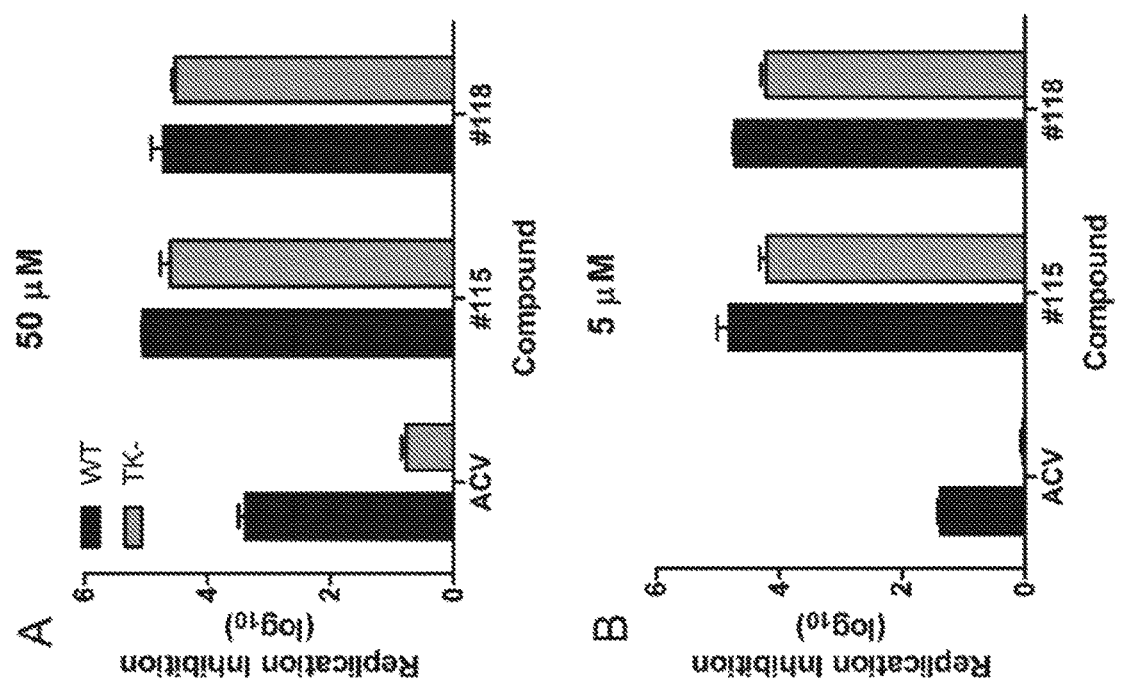
FIGS. 4A & 4B. Sensitivity of thymidine kinase-deficient HSV-2 to αHT compounds. Vero cell monolayers were infected with the indicated wild-type or mutant HSV-1 or HSV-2 strains at moi of 0.1 in the presence of DMSO control, ACV or αHT compounds #115, 118 or 196 at 5 µM. Duplicate cultures were collected 24 hours post-infection and infectious virus titers were determined by plaque assay. Titers in compound-treated samples were subtracted from DMSO-treated samples. Values are the averages±one standard error of the mean. α-Hydroxytropolones inhibit an ACV-resistant mutant of HSV-2. ACV or the indicated α-hydroxytropolone compound was added at 50 µM (FIG. 4A) or 5 µM (FIG. 4B) to cultures infected with wild-type HSV-2 or a TK-deficient mutant of the same strain. $Log_{10}$ suppression was determined relative to the diluent control. Data are the averages of data from duplicate samples±ranges from one of two independent experiments at each concentration.

ACV is a nucleoside analog prodrug that must be phosphorylated by the viral thymidine kinase (TK) for it to become a substrate for the viral DNA polymerase (Elion, et al., 1977). HSV TK-deficient mutants are therefore insensitive to ACV. Because viral resistance to ACV and other nucleoside analogs is a significant medical problem (Field and Biron, 1994; Coen, 1991; Wang, et al, 2011; Duan, et al., 2009; Duan, et al., 2008; Pelosi, et al., 1992), especially in immunocompromised patients (Reyes, et al., 2013; Levin, et al., 2004; Gilbert, et al., 2002; Schmit and Boivin, 1999), the inventors asked whether defined TK-deficient mutants of HSV-2 would be sensitive to αHT compounds. Vero cells were infected with a laboratory strain of HSV-2 and an engineered TK-deficient mutant of the same strain. The cells were treated with 5 µM ACV or compounds #115, 118, or 196 as was done in the primary screening assays, and viral yields 24 hr post-infection were measured by plaque assay. ACV 5 µM inhibited wild-type HSV-2 replication 100-fold, but it had little effect on the TK-mutant (FIG. 4). In marked contrast, compounds #115, 118, and 196 efficiently inhibited the wild-type HSV-2 and the TK-mutant strain. Therefore, these αHT compounds do not require phosphorylation by the viral TK gene to be active, confirming that the αHTs suppress HSV-2 replication in a different manner than ACV. These data also demonstrate that αHT compounds #115, 118 and 196 are stronger inhibitors of HSV-2 than ACV at 5 µM.

Preliminary Anti-HSV SAR Relationships within the Hydroxylated Tropolones.

Figure 5:
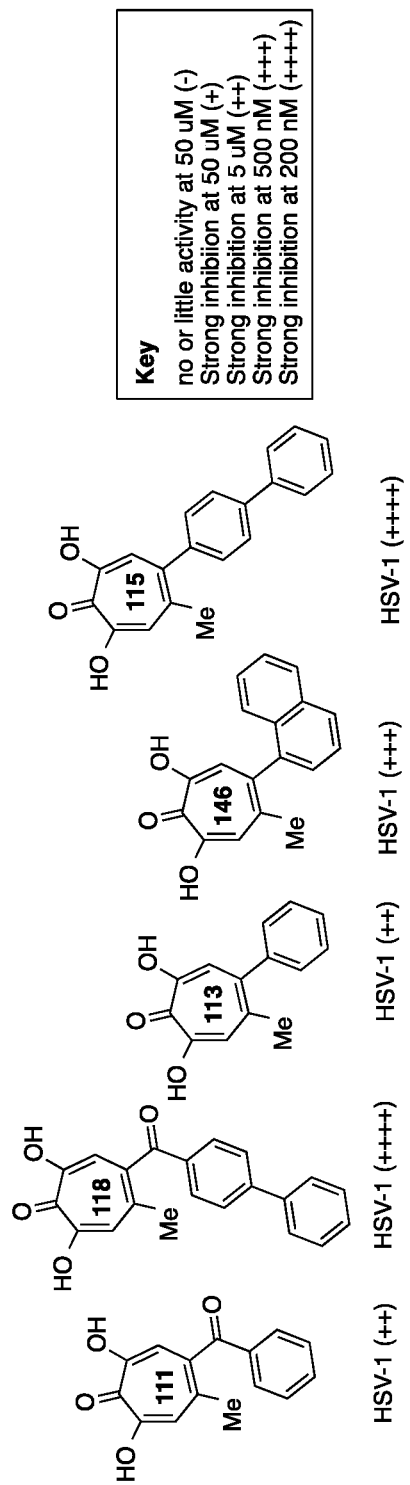
FIG. 5. Representative structure-function analysis of synthetic αHT compounds against HBV.

A series of over 20 synthetic αHTs were synthesized and tested to both confirm the initial SAR, and to provide leads for further optimization pursuits (FIG. 5). Every synthetic αHT tested had at least some antiviral activity for HSV-1 and HSV-2 at 50 µM, which demonstrates the distinctive nature of the αHT pharmacophore for HSV antivirals. While a few of the molecules are inactive at 5 µM, the majority remain highly active at these lower concentrations. Furthermore, a few of these molecules, namely #118, 146, and 115 remained highly inhibitory at much lower concentrations. Specifically, biphenyl-containing molecules #118 and 115 inhibit HSV replication by up to 4 $\log_{10}$ at 200 nM. The increased potency over close analogs #111 and 113 confirmed the importance of added lipophilicity.

The weakest inhibitors, which inhibit at 50 µM but not 5 µM (#106, 108, 109, 110, 112, 117, 143, 144), are also the inhibitors that are the most electronically poor. [All 3 diesters (106,108,109), two smallest ketones (100, 143), and the two monoesters (109, 117) are in this group.] These compounds also have short appendages.

Of the moderate inhibitors, which inhibit at 50 µM and 5 µM (#113 and 172), 113 has a neutral aromatic, so it is smaller than the compounds showing greater inhibition but is less electronically poor than #112. The compound #172 does not have the methyl group at the C5 position that all the other weaker and moderate inhibitors do, suggesting that adding appendages may increase activity.

Compounds fully inhibitory at 5 µM, include ketones (111, 118, 120, 173) that are more hydrophobic than the weaker Compounds #110 and 143. The majority of the aryl substituted compounds (114, 119, 145, 147), are in this group or the group of strongest inhibitors.

Compounds fully inhibitory at 0.5 µM include #115 and 146. These compounds have aryl substituents directly attached to the tropolone core. In addition, these compounds are the most sterically demanding and electronically rich of the troponoids.

Pharmacological Properties.

Several troponoid compounds tested in mouse liver microsomes had long half-lives, low extraction ratios, and no evidence of non-P450 turnover (Table 3), suggesting their capacity to resist rapid degradation and elimination by the liver.

Therapeutic Implications.

The high suppressive activities against the herpesviruses observed with these compounds (as much as 5.92 $\log_{10}$ at 5 µM) and their minimal short-term toxicity implies that the inhibitors, such as compounds #115, 118, 119, 120, 145, 146, 147, and 173, may be suitable for use as anti-viral drugs. This is true for the acute and/or topical therapies most commonly employed for the herpes simplex viruses. The compounds described herein are structurally distinct from the nucleoside analogs currently approved to treat herpesvirus. It is contemplated that based upon the presumed mechanism of action against nucleotidyl transferase superfamily enzymes that the compounds disclosed herein may be effective against viral strains that are resistant to the existing drugs and that combining the nucleoside analog drugs with the hydroxylated tropolone NTS inhibitors may result in additive or synergistic inhibition of viral replication.

TABLE 3

Various αHT compounds show favorable resistance to elimination in mouse liver microsomes.
αHT compounds at 1 µM in mouse liver microsomes

| Compound | t ½ (min) | CL'int (mL/min/kg) | CL 'hep (mL/min/kg) | ER | Non-P450 turn-over |
|---|---|---|---|---|---|
| 46 | 16 | 318 | 70 | 0.78 | No |
| 110 | >120 | 26 | 20 | 0.22 | No |
| 115 | 18 | 285 | 68 | 0.76 | No |
| 118 | 34 | 154 | 57 | 0.63 | Potential |
| 146 | >120 | −43 | −83 | <0.1 | No |
| 147 | >120 | −79 | −657 | <0.1 | No |

Summary.

The disclosure describes hydroxylated tropolone inhibitors of nucleotidyl-transferase superfamily enzymes that suppress replication of HSV-1 and HSV-2 with little or no measurable toxicity in a short-term cell culture assay. Inhibition by these primary screening hits is equal or superior to the approved anti-herpesvirus drug acyclovir. Without wishing to be bound by any theory, it is believed that a hydroxylated tropolone NTS inhibitor blocks at least two stages of the viral replication cycle. The existing compounds may already be superior to the drugs that are used for herpesvirus infection. Inhibitors of NTS enzymes may have a high barrier to development of antiviral resistance, and their different mode(s) of action than the nucleoside analogs implies that these compounds would be good candidates for combination therapy with the existing anti-herpesvirus drugs to improve efficacy of antiviral therapy.

3. Synthesis and Characterization of α-Hydroxytropolones

Scheme 1. General overview of the Synthesis of α-Hydroxytropolones 106-196.

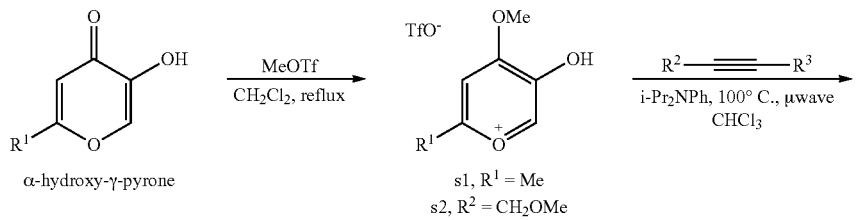

α-hydroxy-γ-pyrone s1, $R^1$ = Me
s2, $R^2$ = CH$_2$OMe

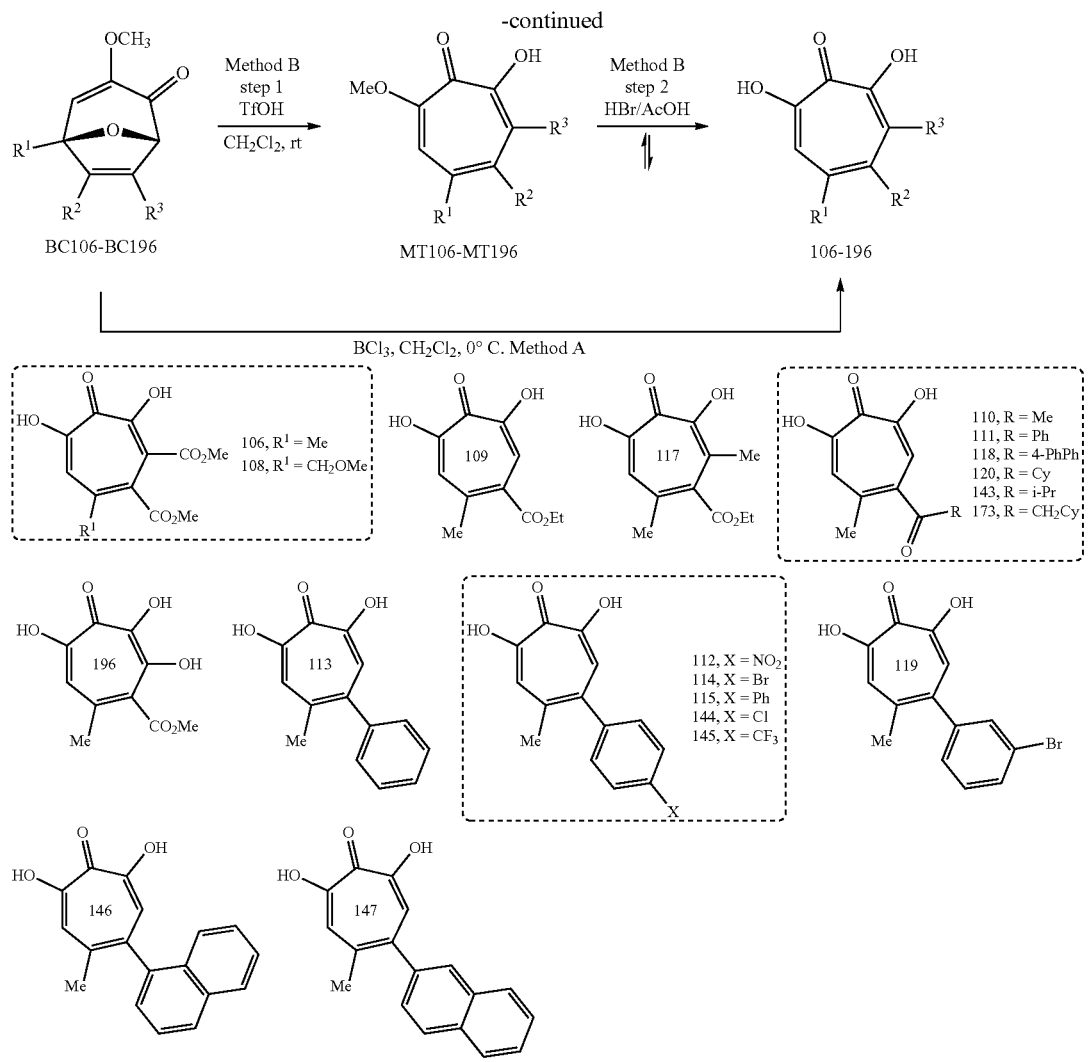

i. Synthesis of Oxidopyrylium Salts (s1 and s2)

5-hydroxy-4-methoxy-2-methylpryrylium triflate (s1)

To a solution of the α-hydroxy-γ-pyrone allomaltol (1.31 g, 10.3 mmol) in $CH_2Cl_2$ was added methyl trifluoromethanesulfonate (MeOTf), (1.77 mL, 15.6 mmol). The reaction was heated to reflux temperatures for 1 hr, at which time the reaction was cooled to room temperature and concentrated to a brown oil. Crystallization from ethyl acetate yielded pure s1 as a white to off-white solid (1.0 g, 33% yield). $^1$H NMR (400 MHz, D20) δ 8.78 (s, 1H), 7.65 (s, 1H), 4.33 (s, 3H), 2.79 (s, 3H). $^{13}$C NMR (100 MHz, $CDCl_3$) δ 176.52 (s), 170.34 (s), 148.59 (s), 143.72 (s), 107.80 (s), 59.94 (s), 20.91 (s).

5-hydroxy-4-methoxy-2-(methoxymethyl)pyrylium triflate (s2)

To a solution of 5-hydroxy-2-(methoxymethyl)-4H-pyran-4-one, (153 mg, 0.994 mmol) in $CH_2Cl_2$ (502 μL) was added methyl trifluoromethanesulfonate (MeOTf), (167 μL, 1.49 mmol). Reaction stirred at reflux for 3.5 hours, cooled to room temperature, and then evaporated under reduced pressure to yield crude s2 as an orange to red tinted oil (282 mg, 87%). The oil was taken up in hot chloroform, to which was added several drops of EtOAc while hot and solution became cloudy. Solution was placed on ice, and a white solid crystallized out 105c (20 mg, 6%). Decomposes at temperatures from 230-235° C. IR (thin film, KBr) 3486 (br), 1634 (m), 1259 (s), 1174 (m), 1035 (s), 764 (w), 643 (w) $cm^{-1}$. $^1$H NMR (400 MHz, $CDCl_3$) δ 8.99 (s, 1H), 7.53 (s, 1H), 4.72 (s, 2H), 4.42 (s, 3H), 3.60 (s, 3H). $^{13}$C NMR (100 MHz, $CDCl_3$) δ 174.37 (s), 171.16 (s), 149.51 (s), 145.13 (s), 105.07 (s), 69.82 (s), 60.01 (s), 59.96 (s). HRMS (ESI+) m/z calc'd for $C_8H_{11}O_4$: 171.0652. Found: 171.0653.

ii. Synthesis of Bicycles (BC106-BC196)

BC106.

5-hydroxy-4-methoxy-2-methylpyrylium triflate S1 (110.4 mg, 0.381 mmol) and DMAD (939 μL, 7.62 mmol) in $CHCl_3$ (762 μL) was added N,N-diisopropylaniline (88 μL, 0.457 mmol). After microwave irradiation at 100° C. for 5 minutes, reaction was purified by chromatography (silica gel, 18 cm×1.8 cm, solvent gradient: hexanes (50 mL); 10% EtOAc in hexanes (100 mL); 15% EtOAc in hexanes (100 mL); 20% EtOAc in hexanes (100 mL); 25% EtOAc in hexanes (200 mL)). Product fractions were concentrated to yield BC106 as an orange solid (96.8 mg, 90% yield). Melting Point (MP)=94-97° C. $R_f$=0.35 in 25% EtOAc in hexanes. IR (thin film, KBr) 2956 (m), 1723 (s), 1653 (m), 1608 (s), 1437 (s), 1323 (s), 1286 (s), 1129 (s), 1073 (m), 1031 (m), 980 (w), 866 (m) cm$^{-1}$. $^1$H NMR (400 MHz, CDCl$_3$) δ 6.03 (s, 1H), 5.26 (s, 1H), 3.91 (s, 3H), 3.80 (s, 3H), 3.61 (s, 3H), 1.68 (s, 3H). $^{13}$C NMR (100 MHz, CDCl$_3$) δ 186.86 (s), 163.72 (s), 161.38 (s), 153.46 (s), 145.20 (s), 135.82 (s), 118.03 (s), 87.79 (s), 86.54 (s), 54.82 (s), 52.76 (s), 52.61 (s), 20.80 (s). HRMS (ESI+) m/z calc'd for $C_{13}H_{14}O_7H+$: 283.08123, Found: 283.08170.

BC108.

5-hydroxy-4-methoxy-2-(methoxymethyl)pyrylium triflate S2 (114.6 mg, 0.358 mmol) and DMAD (870 μL, 7.16 mmol) in CHCl$_3$ (716 μL) was added N,N-diisopropylaniline (84 μL, 0.430 mmol). After microwave irradiation at 100° C. for 15 minutes, reaction was purified by chromatography (silica gel, 18 cm×1.8 cm, solvent gradient: hexanes (50 mL); 10% EtOAc in hexanes (100 mL); 15% EtOAc in hexanes (100 mL); 20% EtOAc in hexanes (100 mL); 25% EtOAc in hexanes (200 mL). Product fractions were concentrated to yield BC108 as a light yellow oil (68.3 mg, 58% yield). $R_f$=0.22 in 26% EtOAc in hexanes. IR (thin film, KBr) 2954 (w), 2841 (w), 1723 (s), 1610 (m), 1437 (m), 1263 (br/s), 1134 (m), 1110 (m), 1080 (w), 1029 (w), 977 (w), 809 (w) cm$^{-1}$. $^1$H NMR (400 MHz, CDCl$_3$) δ 6.03 (s, 1H), 5.31 (s, 1H), 3.87 (s, 3H), 3.81 (dd, J=3.1, 3.1 Hz, 2H), 3.78 (s, 3H), 3.60 (s, 3H), 3.42 (s, 3H). $^{13}$C NMR (100 MHz, CDCl$_3$) δ 186.75, 163.54, 161.11, 151.49, 146.19, 136.16, 114.06, 90.51, 86.73, 71.94, 59.81, 54.95, 52.73, 52.65. HRMS (ESI+) m/z calc'd for $C_{14}H_{16}O_8H^+$: 313.0918. Found: 313.0922.

BC109.

5-hydroxy-4-methoxy-2-methylpyrylium triflate S1 (104 mg, 0.359 mmol) and ethyl propiolate (726 μL, 7.18 mmol) in CHCl$_3$ (718 μl) was added N,N-diisopropylaniline (84 μL, 0.431 mmol). After microwave irradiation at 100° C. for 15 minutes, reaction was purified by chromatography (silica gel, 18 cm×1.8 cm, solvent gradient: hexanes (50 mL); 10% EtOAc in hexanes (100 mL); 15% EtOAc in hexanes (200 mL); Product fractions were concentrated to yield BC109 as an off white solid (75.5 mg, 88% yield). MP=52-55° C. $R_f$=0.38 in 25% EtOAc in hexanes. IR (thin film, KBr) 2982 (w), 2938 (w), 1711 (s), 1604 (m), 1452 (w), 1317 (m), 1128 (m), 1073 (m), 987 (w), 783 (w) cm$^{-1}$. $^1$H NMR (400 MHz, CDCl$_3$) δ 7.08 (d, J=2.5 Hz, 1H), 6.07 (s, 1H), 5.00 (d, J=2.5 Hz, 1H), 4.24 (q, J=7.2 Hz, 2H), 3.54 (s, 3H), 1.76 (s, 3H), 1.31 (t, J=7.1 Hz, 3H). $^{13}$C NMR (100 MHz, CDCl$_3$) δ 189.41, 163.46, 150.25, 145.64, 139.18, 119.99, 86.51, 86.13, 61.80, 55.30, 21.96, 14.78. HRMS (ESI+) m/z calc'd for $C_{12}H_{14}O_5H^+$: 239.0914. Found: 239.09073.

BC110.

5-hydroxy-4-methoxy-2-methylpyrylium triflate S1 (102.4 mg, 0.353 mmol) and 3-butyn-2-one (540 μL, 7.06 mmol) in CHCl$_3$ (706 μL) was added N,N-diisopropylaniline (82 μL, 0.424 mmol). After microwave irradiation at 100° C. for 15 minutes, reaction was purified by chromatography (silica gel, 18 cm×1.8 cm, solvent gradient: hexanes (50 mL); 10% EtOAc in hexanes (100 mL); 15% EtOAc in hexanes (200 mL). Product fractions were concentrated to yield BC110 as a white solid (71 mg, 97% yield). MP=146-150° C. $R_f$=0.23 in 25% EtOAc in hexanes. IR (thin film, KBr) 3074 (s), 2931 (w), 1708 (s), 1663 (s), 1608 (s), 1441 (w), 1228 (m). 1129 (m). 1063 (m), 990 (w), 881 (w), 660 (w) cm$^{-1}$. $^1$H NMR (400 MHz, CDCl$_3$) δ 7.07 (d, J=1.4 Hz. 1H), 6.08 (s, 1H), 5.03 (d, J=1.4 Hz, 1H), 3.52 (s, 3H), 2.36 (s, 3H), 1.71 (s, 3H). $^{13}$C NMR (100 MHz, CDCl$_3$) δ 194.63, 189.16, 156.78, 145.40, 139.26, 119.94, 86.40, 86.13, 55.03, 28.07, 21.63. HRMS (ESI+) m/z calc'd for $C_{11}H_{12}O_4Na^+$: 231.06278. Found: 231.06338.

BC111.

5-hydroxy-4-methoxy-2-methylpyrylium triflate S1 (100 mg, 0.340 mmol) and benzyl acetylene (225 mg, 1.72 mmol) in CHCl$_3$ (706 μL) was added N,N-diisopropylaniline (80 μL, 0.408 mmol). After microwave irradiation at 100° C. for 10 minutes, reaction was purified by chromatography (silica gel, 26 cm×2.6 cm, solvent gradient: hexanes (50 mL); 2% EtOAc in hexanes (100 mL), 5% EtOAc in hexanes (100 mL), 10% EtOAc in hexanes (100 mL); 20%-25% EtOAc in hexanes (200 mL). Product fractions were concentrated to yield BC111 as a light yellow solid (78 mg, 85% yield). In addition, the benzyl acetylene was re-isolated (125 mg, 70% yield; 180 mg would be 100% theoretical yield of un-reacted product). MP=93-95° C. $R_f$=0.50 in 30% EtOAc in hexanes. IR (thin film, KBr) 3068 (w), 2978 (w), 2936 (w), 1711 (s), 1643 (s), 1608 (s), 1448 (m), 1325 (s), 1227 (m), 1180 (m), 1126 (s), 1075 (m), 988 (m), 819 (m), 843 (m), 701 (m), 667 (m), 654 (m) cm$^{-1}$. $^1$H NMR (400 MHz, CDCl$_3$) δ 7.82 (d, J=7.2 Hz, 2H), 7.59 (t, J=7.4 Hz, 1H), 7.47 (dd, J=7.6, 7.6 Hz, 2H), 6.78 (d, J=2.3 Hz, 1H), 6.26 (s, 1H), 5.15 (d, J=2.5 Hz, 1H), 3.56 (s, 3H), 1.74 (s, 3H). $^{13}$C NMR (100 MHz, CDCl$_3$) δ 190.59, 188.44, 155.01, 145.05, 138.84, 136.82, 133.61, 129.01, 128.73, 120.31, 87.04, 86.70, 54.71, 20.80. HRMS (ESI+) m/z calc'd for $C16H14O4H^+$: 271.0965. Found: 271.0964.

BC112.

5-hydroxy-4-methoxy-2-methylpyrylium triflate S1 (100 mg, 0.355 mmol) and 1-ethynyl-4-nitrobenzene (1.05 g, 7.10 mmol) in CHCl$_3$ (2.80 ml) was added N,N-diisopropylaniline (83 μL, 0.426 mmol). After microwave irradiation at 100° C. for 30 minutes, reaction was purified by chromatography (silica gel, 26 cm×2.6 cm solvent gradient, dry loaded): hexanes (50 mL); 10% EtOAc in hexanes (100 mL); 15% EtOAc in hexanes (100 mL); 20% EtOAc in hexanes (100 mL); 25% EtOAc in hexanes (200 mL)). Product fractions were concentrated to yield BC112 as a yellow solid (65 mg, 64% yield). MP=145-148° C. $R_f$=0.27 in 16% EtOAc in hexanes. IR (thin film, KBr) 3075 (w), 2935 (w), 1712 (s), 1604 (m), 1516 (s), 1453 (w), 1341 (s), 1129 (m), 1108 (w), 987 (w), 865 (w), 851 (m), 750 (m) cm$^{-1}$. $^1$H NMR (400 MHz, CDCl$_3$) δ 8.24 (d, J=8.7 Hz, 2H), 7.44 (d, J=8.7, 2H), 6.51 (d, J=2.5 Hz, 1H), 6.18 (s, 1H), 5.03 (d, J=2.5 Hz, 1H), 3.61 (s, 3H), 1.67 (s, 3H). $^{13}$C NMR (100 MHz, CDCl$_3$) δ 189.08, 156.93, 147.67, 146.13, 139.53, 127.42, 126.77, 124.07, 118.26, 86.33, 86.00, 54.84, 21.95. HRMS (ESI+) m/z calc'd for $C_{15}H_{13}NO_5H^+$: 288.0866. Found: 288.0866.

BC113.

5-hydroxy-4-methoxy-2-methylpyrylium triflate S1 (102.8 mg, 0.354 mmol) and phenylacetylene (776 μL, 7.08 mmol) in CHCl$_3$ (708 μL) was added N,N-diisopropylaniline (83 μL, 0.425 mmol). After microwave irradiation at 100° C. for 30 minutes, reaction was purified by chromatography (silica gel, 18 cm×1.8 cm, solvent gradient): hexanes (50 mL); 10% EtOAc in hexanes (75 mL); 15% EtOAc in hexanes (200 mL); Product fractions were concentrated to yield BC113 as an off white solid (49 mg, 57% yield). MP=76-84° C. $R_f$=0.56 in 26% EtOAc in hexanes. IR (thin film, KBr) 2977 (w), 2934 (w), 2836 (w), 1711 (s), 1606 (m), 1491 (w), 1446 (w), 1130 (m), 1058 (w), 864 (m), 755 (m), 977 (w), 697 (w), 661 (w) cm$^{-1}$. $^1$H NMR (400 MHz, CDCl$_3$) δ 7.43-7.34 (m, 3H), 7.29 (dd, J=5.1, 2.8 Hz, 2H), 6.28 (d, J=2.4 Hz, 1H), 6.19 (s, 1H), 4.99 (d, J=2.5 Hz, 1H), 3.60 (s, 3H), 1.68 (s, 3H). $^{13}$C NMR (100 MHz, CDCl$_3$)

δ 189.89, 158.72, 145.91, 133.02, 128.73, 128.70, 125.97, 123.00, 119.13, 86.39, 85.81, 54.71, 22.08. HRMS (ESI+) m/z calc'd for $C_{15}H_{14}O_3Na^+$: 265.0835. Found: 265.0836.

BC114.

5-hydroxy-4-methoxy-2-methylpyrylium triflate S1 (100 mg, 0.34 mmol), and 1-ethynyl-4-bromobenzene (1.0 g, 6.9 mmol) were suspended in $CHCl_3$ (2 mL). N,N Diisopropylaniline (81 µL, 0.41 mmol) was added to the reaction, the reaction vessel was sealed, and the reaction mixture was heated under microwave irradiation at 100° C. (controlled temperature) for 30 min. The reaction mixture was then concentrated and purified by chromatography (silica gel, 18×1.8 cm, 50 mL Hexanes, 200 mL 2% EtOAc in hexanes, 100 mL 10% EtOAc in Hexanes, 200 mL 15% EtOAc in Hexanes) to lead to BC114 as a light yellow solid (68 mg, 61% yield). MP=192-200° C. $R_f$=0.17 in 16% EtOAc/Hexanes. FTIR (KBr, thin film) 525 (m), 714 (m), 1057 (w), 1132 (m), 1606 (s), 1708 (s), 1905 (w), 2978 (m) cm-1. $^1$H NMR (400 MHz, $CDCl_3$) δ 7.49 (d, J=8.5 Hz, 2H), 7.14 (d, J=8.5 Hz, 2H), 6.29 (d, J=2.5 Hz, 1H), 6.14 (s, 1H), 4.96 (d, J=2.5 Hz, 1H), 3.58 (s, 3H), 1.64 (s, J=3H). $^{13}$C NMR (100 MHz, $CD_3CN/CDCl_3$) δ 189.43, 157.75, 145.66, 132.19, 131.73, 127.99, 124.04, 122.10, 119.73, 86.16, 85.77, 54.47, 21.35. HRMS (ESI+): calc'd for $C_{15}H_{14}BrO_3$ (M+H): 321.0121; Found: 321.0114.

BC117.

5-hydroxy-4-methoxy-2-methylpyrylium triflate s1 (106.3 mg, 0.367 mmol) and ethyl but-2-ynoate (855 µL, 7.34 mmol) in $CHCl_3$ (734 µL) was added N,N-diisopropylaniline (78 µL, 0.440 mmol). After microwave irradiation at 100° C. for 60 minutes, reaction was purified by chromatography (silica gel, 18 cm×1.8 cm, solvent gradient: hexanes (50 mL); 2% EtOAc in hexanes (50 mL); 5% EtOAc in hexanes (200 mL); 10% EtOAc in hexanes (300 mL). Product fractions were concentrated to yield BC117 as a white solid (29.3 mg, 32% yield). MP=64-66° C. $R_f$=0.53 in 25% EtOAc in hexanes. IR (thin film, KBr) 2981 (w), 2937 (w), 1706 (s), 1606 (m), 1446 (w), 1328 (m), 1132 (m), 1083 (m), 1048 (m), 871 (w), 785 (w) cm$^{-1}$. $^1$H NMR (400 MHz, $CDCl_3$) δ 6.13 (s, 1H), 4.80 (s, 1H), 4.36-4.15 (m, 2H), 3.54 (s, 3H), 2.12 (s, 3H), 1.71 (s, 3H), 1.32 (t, J=6.9 Hz, 3H). $^{13}$C NMR (100 MHz, $CDCl_3$) δ 190.23, 164.58, 152.19, 145.66, 141.22, 121.66, 91.06, 87.45, 61.36, 55.25, 22.45, 14.86, 13.33. HRMS (ESI+) m/z calc'd for $C_{13}H_{16}O_5H^+$: 253.1071. Found: 253.1059.

BC118.

5-hydroxy-4-methoxy-2-methylpyrylium triflate s1 (100 mg, 0.345 mmol) and 1-([1,1'-biphenyl]-4-yl)prop-2-yn-1-one (712 mg, 3.45 mmol, 10 eq) in $CH_2Cl_2$ (5 mL) was added N,N-diisopropylaniline (81 µL, 0.414 mmol, 1.2 eq). After microwave irradiation at 100° C. for 1 hr, the reaction mixture was concentrated and purified by chromatography (Silica [10 g], 0% EtOAc/hexane to 35% EtOAc/hexane gradient over 20 column volumes), yielding BC118 as an orange solid (92.8 mg, 77% yield). MP=156-159° C. $R_f$=0.22 in 20% EtOAc in hexanes. IR (thin film, KBr) 3063 (w), 2979 (w), 2935 (w), 2837 (w), 1711 (s), 1641 (m), 1603 (s), 1449 (w), 1323 (m), 1127 (m), 1043 (w), 989 (w), 844 (m), 744 (s), 698 (m) cm$^{-1}$. $^1$H NMR (400 MHz, $CDCl_3$) δ 7.93 (d, J=8.3 Hz, 2H), 7.71 (d, J=8.3 Hz, 2H), 7.65-7.61 (m, 2H), 7.51-7.38 (m, 3H), 6.83 (d, J=2.4 Hz, 1H), 6.30 (s, 1H), 5.20 (d, J=2.5 Hz, 1H), 3.60 (s, 3H), 1.77 (s, 3H). $^{13}$C NMR (100 MHz, $CDCl_3$) δ 190.37, 188.72, 155.32, 146.66, 145.31, 139.84, 138.77, 135.73, 129.91, 129.29, 128.71, 127.63, 127.54, 120.67, 87.37, 87.01, 54.98, 21.07. HRMS (ESI+) m/z calc'd for $C_{22}H_{19}O_4^+$: 347.1278. Found: 347.1280.

BC119—

5-hydroxy-4-methoxy-2-methylpyrylium triflate s1 (100 mg, 0.345 mmol) and 1-bromo-3-ethynylbenzene (500 mg) in $CDCl_3$ (1.725 mL) was added N,N-diisopropylaniline (135 µL, 2 eq). After microwave irradiation at 100° C. for 4 hr, the reaction mixture was concentrated and purified by chromatography. (80.3 mg, 73% yield). $^1$H NMR (200 MHz, $CDCl_3$) δ7.62-7.01 (m, 6H), 6.33 (d, J=2.5 Hz, 1H), 6.16 (s, 1H), 4.99 (d, J=2.5 Hz, 1H), 3.61 (s, 3H), 1.66 (s, 3H). $^{13}$C NMR (100 MHz, $CDCl_3$) δ 189.56, 157.40, 146.00, 135.13, 131.63, 130.24, 128.96, 124.64; 124.54, 122.85, 118.73, 86.30, 85.79, 54.81, 22.00, 21.36.

BC120.

To a solution of salt 5-hydroxy-4-methoxy-2-methylpyrylium triflate s1 (94 mg, 0.324 mmol) and 1-cyclohexylprop-2-yn-1-one (220.5 mg, 1.62 mmol) in $CDCl_3$ (2 µL) was added N,N-diisopropylaniline (75.7 µL, 0.390 mmol). After microwave irradiation at 100° C. for 45 min, the reaction mixture was purified by chromatography (silica gel, 18 cm×1.8 cm, solvent gradient: 5% EtOAc in hexanes (100 mL); 10% EtOAc in hexanes (100 mL); 20% EtOAc in hexanes (200 mL); 30% EtOAc in hexanes (100 mL)). Product fractions were concentrated to yield BC120 as a yellow oil (78.23 mg, 87% yield). $R_f$=0.24 in 15% EtOAc in hexanes. IR (thin film, KBr) 3057 (w), 2933 (s), 2855 (s), 1712 (s), 1667 (s), 1609 (s), 1450 (m), 1341 (m), 1179 (m), 1128 (s), 871 (m), 746 (m) cm$^{-1}$. $^1$H NMR (200 MHz, $CDCl_3$) δ 6.91 (d, J 2.5 Hz, 1H), 6.05 (s, 1H), 4.97 (d, J 2.6 Hz, 1H), 3.45 (s, 3H), 2.73 (tt, J=11.2, 3.3 Hz, 1H), 1.59 (s, 3H), 1.84-1.05 (m, 10H). $^{13}$C NMR (100 MHz, $CDCl_3$) δ 200.87, 189.01, 155.74, 145.12, 136.64, 120.06, 86.40, 86.12, 54.78, 48.18, 30.12, 27.93, 26.01, 25.86, 25.26, 21.22. HRMS (ESI+) m/z calc'd for $C_{16}H_{21}O_4$ (M+H): 277.1434. Found: 277.1439.

BC143.

To a solution of 5-hydroxy-4-methoxy-2-methylpyrylium triflate s1 (258.3 mg, 0.890 mmol) and 4-methylpent-1-yn-3-one (427.64 mg, 4.45 mmol) in $CDCl_3$ (3 mL) was added N,N-diisopropylaniline (433 µL, 2.23 mmol). After microwave irradiation at 100° C. for 45 min, the reaction mixture was purified by chromatography (Biotage Isolera Prime, 10 g silica gel column, solvent gradient: 2% EtOAc in hexanes (3 CV); 2-5% EtOAc in hexanes (8 CV); 5-10% EtOAc in hexanes (12 CV); 10-15% EtOAc in hexanes (8 CV); 15-25% EtOAc in hexanes (10 CV); 25-35% EtOAc in hexanes (7 CV)). Product fractions were concentrated to yield BC143 as a yellow oil (148.1 mg, 70% yield). $R_f$=0.34 in 20% EtOAc in hexanes. IR (thin film, KBr) 3061 (s), 2974 (m), 2936 (w), 1713 (s), 1670 (s), 1610 (s), 1459 (w), 1343 (m), 1291 (m), 1180 (m), 1128 (m), 1048 (m), 873 (w) cm$^{-1}$. $^1$H NMR (200 MHz, $CDCl_3$) δ 6.93 (d, J 2.2 Hz, 1H), 6.06 (s, 1H), 4.98 (d, J 2.4 Hz, 1H), 3.46 (s, 3H), 3.09-2.94 (m, 1H), 1.61 (s, 3H), 1.07 (d, J 7.1 Hz, 3H), 1.03 (d, J 6.6 Hz, 3H). $^{13}$C NMR (100 MHz, $CDCl_3$) δ 201.47, 189.01, 155.67, 145.15, 136.90, 120.03, 86.42, 86.14, 54.81, 38.15, 21.22, 19.76, 17.79. HRMS (ESI+) m/z calc'd for $C_{13}H_{17}O_4$ (M+H): 237.1121. Found: 237.1124.

BC144.

To a solution of 5-hydroxy-4-methoxy-2-methylpyrylium triflate s1 (100.0 mg, 0.344 mmol) and 1-chloro-4-ethynylbenzene (469.83 mg, 3.44 mmol) in $CDCl_3$ (689 µL) was added N,N-diisopropylaniline (80 µL, 0.413 mmol). After microwave irradiation at 100° C. for 60 min, the reaction mixture was purified by chromatography (Biotage Isolera Prime, 10 g silica gel column, solvent gradient: 5% EtOAc in hexanes (3 CV); 2-5% EtOAc in hexanes (8 CV); 5-10% EtOAc in hexanes (10 CV); 10-20% EtOAc in hexanes (10

CV); 20-35% EtOAc in hexanes (8 CV)). Product fractions were concentrated to yield BC144 as a yellow solid (37.8 mg, 40% yield). Melting Point (MP)=138-141° C. Rf=0.27 in 25% EtOAc in hexanes. IR (thin film, KBr) 3066 (w), 2974 (w), 2935 (w), 2839 (w), 1711 (s), 1604 (m), 1490 (w), 1174 (w), 1131 (w), 1092 (w), 864 (w), 827 (w) cm$^{-1}$. $^1$H NMR (200 MHz, CDCl$_3$) δ 7.36 (d, J 8.7 Hz, 2H), 7.21 (d, J 8.7 Hz, 2H), 6.29 (d, J 2.3 Hz, 1H), 6.16 (s, 1H), 4.98 (d, J 2.5 Hz, 1H), 3.60 (s, 3H), 1.66 (s, 3H). $^{13}$C NMR (100 MHz, CDCl$_3$) δ 189.89, 157.91, 146.22, 134.83, 131.68, 129.23, 127.52, 123.89, 119.02, 86.52, 85.99, 55.01, 22.27. HRMS (ESI+) m/z calc'd for C$_{15}$H$_4$ClO$_3$ (M+H): 277.0626. Found: 277.0622.

BC145.

To a solution of 5-hydroxy-4-methoxy-2-methylpyrylium triflate s1 (100.2 mg, 0.345 mmol) and 1-ethynyl-4-(trifluoromethyl)benzene (563 µL, 3.45 mmol) in CDCl$_3$ (690 µL) was added N,N-diisopropylaniline (80 µL, 0.414 mmol). After microwave irradiation at 100° C. for 60 min, the reaction mixture was purified by chromatography (Biotage Isolera Prime, 25 g silica gel column, solvent gradient: 5% EtOAc in hexanes (3 CV); 2-5% EtOAc in hexanes (8 CV); 5-10% EtOAc in hexanes (10 CV); 10-20% EtOAc in hexanes (10 CV); 20-35% EtOAc in hexanes (8 CV)). Product fractions were concentrated to yield BC145 as a yellow oil (77.6 mg, 72% yield). R$_f$=0.30 in 25% EtOAc in hexanes. IR (thin film, KBr) 3063 (w), 2981 (w), 2938 (w), 2840 (w), 1713 (s), 1606 (m), 1410 (w), 1327 (s), 1129 (s), 1016 (m), 865 (w), 832 (w) cm$^1$. $^1$H NMR (200 MHz, CDCl$_3$) δ 7.63 (d, J 8.1 Hz, 2H), 7.38 (d, J 8.1 Hz, 2H), 6.40 (d, J 2.5 Hz, 1H), 6.16 (s, 1H), 5.01 (d, J 2.5 Hz, 1H), 3.60 (s, 1H), 1.66 (s, 1H). $^{13}$C NMR (100 MHz, CDCl$_3$) δ 189.76, 157.84, 146.31, 136.93, 130.89 (q, J 32.8 Hz), 126.60, 126.03 (q, J 3.8 Hz), 125.85, 124.18 (q, J 272.1 Hz), 118.92, 86.65, 86.20, 55.09, 22.27. HRMS (ESI+) m/z calc'd for C$_{16}$H$_{14}$F$_3$O$_3$ (M+H): 311.0890. Found: 311.0890.

BC146.

To a solution of 5-hydroxy-4-methoxy-2-methylpyrylium triflate s1 (108.2 mg, 0.373 mmol) and 1-ethynylnapthalene (527 µL, 3.73 mmol) in CDCl$_3$ (746 µL) was added N,N-diisopropylaniline (87 µL, 0.447 mmol). After microwave irradiation at 100° C. for 60 min, the reaction mixture was purified by chromatography (Biotage Isolera Prime, 10 g silica gel column, solvent gradient: 5% EtOAc in hexanes (3 CV); 2-5% EtOAc in hexanes (8 CV); 5-10% EtOAc in hexanes (10 CV); 10-20% EtOAc in hexanes (10 CV); 20-35% EtOAc in hexanes (8 CV)). Product fractions were concentrated to yield BC146 as an orange oil (85.7 mg, 79% yield). R$_f$=0.30 in 25% EtOAc in hexanes. IR (thin film, KBr) 3057 (w), 2978 (w), 2930 (w), 2836 (w), 1710 (s), 1605 (m) 1345 (w), 1268 (w), 1132 (m), 1117 (w), 989 (w), 778 (w) cm$^{-1}$. $^1$H NMR (200 MHz, CDCl$_3$) δ 8.05-7.94 (m, 1H), 7.91-7.67 (m, 2H), 7.58-7.35 (m, 3H), 7.22 (d, J 1.2 Hz, 1H), 6.39 (d, J 2.2 Hz, 1H), 6.16 (s, 1H), 5.18 (d, J 2.5 Hz, 1H), 3.67 (s, 3H), 1.51 (s, 3H). $^{13}$C NMR (100 MHz, CDCl$_3$) δ 190.22, 156.46, 145.93, 134.03, 131.60, 131.56, 128.84, 128.70, 126.76, 126.67, 126.47, 125.67, 125.09, 123.68, 120.19, 88.18, 86.77, 55.02, 21.64. HRMS (ESI+) m/z calc'd for C$_{19}$H$_{17}$O$_3$ (M+H): 293.1172. Found: 293.1175.

BC147.

To a solution of 5-hydroxy-4-methoxy-2-methylpyrylium triflate s1 (17.0 mg, 0.058 mmol) and 2-ethynylnapthalene (88.9 mg, 0.584 mmol) in CDCl$_3$ (117 µL) was added N,N-diisopropylaniline (13.7 µL, 0.070 mmol). After microwave irradiation at 100° C. for 60 min, the reaction mixture was purified by chromatography (Biotage Isolera Prime, 10 g silica gel column, solvent gradient: 5% EtOAc in hexanes (3 CV); 2-5% EtOAc in hexanes (8 CV); 5-10% EtOAc in hexanes (10 CV); 10-20% EtOAc in hexanes (10 CV); 20-35% EtOAc in hexanes (8 CV)). Product fractions were concentrated to yield BC147 as a yellow oil (14.4 mg, 84% yield). R$_f$=0.28 in 25% EtOAc in hexanes. IR (thin film, KBr) 3056 (w), 2963 (w), 2933 (w), 2837 (w), 1708 (m), 1605 (w), 1174 (w), 1344 (w), 1131 (m), 1101 (w), 867 (w), 694 (w) cm$^{-1}$. $^1$H NMR (200 MHz, CDCl$_3$) δ 7.89-7.80 (m, 3H), 7.71 (d, J 1.5 Hz, 1H), 7.55-7.48 (s, 1H), 7.44 (d, J 1.7 Hz, 1H), 7.40 (d, J 1.8 Hz, 1H), 6.41 (d, J 2.5 Hz, 1H), 6.30 (s, 1H), 5.05 (d, J 2.5 Hz, 1H), 3.64 (s, 3H), 1.76 (s, 3H). $^{13}$C NMR (50 MHz, CDCl$_3$) δ 190.17, 159.03, 146.36, 133.49, 133.39, 130.68, 128.88, 128.47, 128.10, 127.07, 127.02, 125.04, 124.44, 123.68, 119.45, 86.80, 86.16, 55.12, 22.65. HRMS (ESI+) m/z calc'd for C$_{19}$H$_{16}$O$_3$Na (M+Na): 315.0992. Found: 315.0997.

BC173.

To a solution of 5-hydroxy-4-methoxy-2-methylpyrylium triflate s1 (106 mg, 0.363 mmol) and 1-cyclohexylbut-3-yn-2-one (272.8 mg, 1.82 mmol) in CDCl$_3$ (4 mL) was added triethylamine (60.7 µL, 0.436 mmol). After microwave irradiation at 100° C. for 35 min, the reaction mixture was purified by chromatography (Biotage Isolera Prime, 10 g silica gel column, solvent gradient: 2% EtOAc in hexanes (3 CV); 2-5% EtOAc in hexanes (10 CV); 5-10% EtOAc in hexanes (15 CV); 10-20% EtOAc in hexanes (10 CV); 20-35% EtOAc in hexanes (8 CV)). Product fractions were concentrated to yield BC173 as a yellow/brown oil (67.7 mg, 64% yield). R$_f$=0.20 in 15% EtOAc in hexanes. IR (thin film, KBr) 3052 (w), 2924 (s), 2851 (m), 1713 (m), 1668 (m), 1609 (m), 1449 (w), 1178 (w), 1127 (m), 1047 (w), 987 (w), 869 (w), 773 (w) cm$^{-1}$. $^1$H NMR (200 MHz, CDCl$_3$) δ 6.96 (d, J 2.3 Hz, 1H), 6.07 (s, 1H), 5.01 (d, J 2.4 Hz, 1H), 3.50 (s, 3H), 2.55 (dd, J=15.3, 6.5 Hz, 1H), 2.44 (dd, J=15.3, 7.3 Hz, 1H), 1.87-1.74 (m, 1H), 1.67 (s, 3H), 1.65-1.55 (m, 4H), 1.31-0.81 (m, 6H). $^{13}$C NMR (100 MHz, CDCl$_3$) δ 197.12, 188.84, 156.63, 144.93, 137.58, 119.68, 86.12, 85.78, 54.60, 47.78, 34.58, 33.31, 33.04, 26.04, 26.00, 25.94, 21.17. HRMS (ESI+) m/z calc'd for C$_{17}$H$_{22}$NaO$_4$ (M+Na): 313.1410. Found: 313.1419 BC196. To a solution of salt s1 (185.0 mg, 0.6373 mmol) and methyl 3-iodopropiolate (1.3365 g, 6.3734 mmol) in CH$_2$Cl$_2$ (2 mL) was added N,N-diisopropylaniline (148.8 µL, 0.7649 mmol). After microwave irradiation at 120° C. for 20 min, the reaction mixture was purified by chromatography (Biotage Isolera Prime, 25 g silica gel column, solvent gradient: 5% EtOAc in hexanes (3 CV); 5-10% EtOAc in hexanes (8 CV); 10-15% EtOAc in hexanes (10 CV); 15-20% EtOAc in hexanes (10 CV); 20-25% EtOAc in hexanes (10 CV); 25-35% EtOAc in hexanes (8 CV)). Product fractions were concentrated to yield a yellow solid (126.2 mg, 57% yield). To a solution of this product (21.3 mg, 0.0608 mmol) in methanol (3 mL) was added 4-dimethylaminopryidine (19.92 mg, 0.1631 mmol). After microwave irradiation at 120° C. for 20 min, the reaction mixture was concentrated under reduced pressure, taken up in CH$_2$Cl$_2$ (10 mL) and washed with a saturated ammonium chloride solution (5×10 mL). The organic layer was isolated, dried over Na$_2$SO$_4$, filtered, and concentrated under reduced pressure to yield BC196 as a yellow oil (7.3 mg, 47% yield; 27% overall yield). $^1$H NMR (200 MHz, CDCl$_3$) δ 6.19 (s, 1H), 5.02 (s, 1H), 3.98 (s, 3H), 3.78 (s, 3H), 3.56 (s, 3H), 1.73 (s, 3H). $^{13}$C NMR (100 MHz, CDCl$_3$) δ 188.61, 168.46, 163.64, 144.93, 121.63, 113.99, 85.79, 83.17, 60.52, 54.72, 51.48, 22.84.

iii. Synthesis of α-Hydroxytropolones (106-196)

106.

A solution of $BCl_3$ (1.0 M in $CH_2Cl_2$) (588 μL, 0.588 mmol) was diluted with $CH_2Cl_2$ (6.0 mL) and cooled to 0° C. In a separate round bottom flask, BC106 (23.7 mg, 0.084 mmol) was dissolved in $CH_2Cl_2$ (6.0 mL), was cooled to 0° C. and was added to the BCl3 solution. After 10 minutes of stirring at 0° C., the reaction mixture was quenched with $H_2O$ (12.0 mL), stirred for 2 minutes at 0° C., and then warmed to room temperature where it continued to stir for 60 minutes. The organic layer was isolated and the aqueous layer was extracted with $CH_2Cl_2$, (5×10 mL). Combined organics were dried over $Na_2SO_4$, filtered, and concentrated under reduced pressure to yield 106 as a yellow solid (17.4 mg, 77%). MP=159-161° C. IR (thin film, KBr) 3260 (br), 2957 (w), 1738 (s), 1543 (m), 1436 (w), 1256 (br/s), 1154 (m), 1065 (w), 1029 (w), 962 (w), 754 (w) $cm^{-1}$. $^1H$ NMR (400 MHz, $CDCl_3$) δ 7.48 (s, 1H), 3.94 (s, 3H), 3.89 (s, 3H), 2.46 (s, 3H). $^{13}C$ NMR (100 MHz, $CDCl_3$) δ 169.27, 168.41, 166.90, 158.40, 154.56, 138.42, 132.18, 125.28, 124.48, 53.40, 53.20, 25.74. HRMS (ESI+) m/z calc'd for $C_{12}H_{12}O_7Na^+$: 291.04752. Found: 291.04831.

108.

A solution of BC13 (1.0 M in $CH_2Cl_2$) (459 μL, 459 mmol) was diluted with $CH_2Cl_2$ (4.7 mL) and cooled to 0° C. In a separate round bottom flask, BC108 (20.5 mg, 0.066 mmol) was dissolved in $CH_2Cl_2$ (4.7 mL), was cooled to 0° C. and was added to the BC13 solution. After 10 minutes of stirring at 0° C., the reaction mixture was quenched with $H_2O$ (9.4 mL), stirred for 2 minutes at 0° C., and then warmed to room temperature where it continued to stir for 1 hour. The organic layer was isolated and the aqueous layer was extracted with $CH_2Cl_2$, (5×10 mL). Combined organics were dried over $Na_2SO_4$, filtered, and concentrated under reduced pressure to yield 108 as a yellow oil (16.6 mg, 85%). IR (thin film, KBr) 3261 (br), 2953 (w), 1738 (s), 1548 (m), 1436 (m), 1343 (m), 1259 (s), 1148 (m), 1100 (m), 1061 (m), 890 (w), 734 (w), 668 (w) $cm^{-1}$. $^1H$ NMR (400 MHz, $CDCl_{13}$) δ 7.73 (s, 1H), 4.48 (s, 2H), 3.94 (s, 3H), 3.88 (s, 3H), 3.35 (s, 3H). $^{13}C$ NMR (100 MHz, $CDCl_3$) δ 169.26, 167.57, 166.58, 158.84, 155.45, 138.76, 131.26, 125.32, 121.17, 74.79, 58.47, 53.25, 53.13. HRMS (ESI+) m/z calc'd for $C_{13}H_{14}O_8H^+$: 299.0761. Found: 299.0757.

109.

A solution of BC13 (1.0 M in $CH_2Cl_2$) (627 μL, 0.627 mmol) was diluted with $CH_2Cl_2$ (6.4 mL) and cooled to 0° C. In a separate round bottom flask, BC109 (21.3 mg, 0.089 mmol) was dissolved in $CH_2Cl_2$ (6.4 mL), was cooled to 0° C. and was added to the $BCl_3$ solution. After 10 minutes of stirring at 0° C., the reaction mixture was quenched with $H_2O$ (12.8 mL), stirred for 2 minutes at 0° C., and then warmed to room temperature where it continued to stir for 30 minutes. The organic layer was isolated and the aqueous layer was extracted with $CH_2Cl_2$, (3×10 mL) and EtOAc (2×10 mL). Combined organics were dried over $Na_2SO_4$, filtered, and concentrated under reduced pressure. To the resulting solid was added $CHCl_3$ where a white solid precipitated out. The organic layer was decanted off and concentrated under reduced pressure to yield an ~10:1 ratio of 109:MT109 as a brownish green solid (7.9 mg, 39%). To the methoxytropolone-containing sample of 109 (7.9 mg, 0.033 mmol) was added acetic acid (192 μl) and 33% HBr in acetic acid (224 μl), and reaction was left to stir at 90° C. for 3 hours. After 3 hours, reaction mixture was let to cool to room temperature. The reaction was quenched with 7 pH phosphate buffer, and diluted with $CH_2Cl_2$. The organic layer was washed several times with the phosphate buffer. The organic layer was dried over $Na_2SO_4$, and evaporated under reduced pressure to yield a brown solid 109 (3.1 mg, 42% yield). Decomposes at temperatures above 80° C. IR (thin film, KBr) 3260 (br), 2917 (w), 2849 (w), 1718 (s), 1500 (w), 1462 (w), 1217 (br/s), 1094 (m), 922 (w), 785 (w) $cm^{-1}$. $^1H$ NMR (400 MHz, $CDCl_3$)$^1$ δ 7.68 (s, 1H), 7.45 (s, 1H), 4.37 (q, J=7.1 Hz, 2H), 2.53 (s, 3H), 1.38 (t, J=7.1 Hz, 3H). $^{13}C$ NMR (100 MHz, $CDCl_3$) δ 168.72, 168.65, 159.04, 156.74, 140.73, 132.94, 124.35, 120.54, 62.28, 25.67, 14.33. HRMS (ESI+) m/z calc'd for $C_{11}H_{12}O_5H^+$: 225.07575. Found: 225.07611.

110.

A solution of $BCl_3$ (1.0 M in $CH_2Cl_2$) (673 μL, 0.673 mmol) was diluted with $CH_2Cl_2$ (6.9 mL) and cooled to 0° C. In a separate round bottom flask, BC110 (20.0 mg, 0.096 mmol) was dissolved in $CH_2Cl_2$ (6.9 mL), was cooled to 0° C. and was added to the $BCl_3$ solution. After 10 minutes of stirring at 0° C., the reaction mixture was quenched with $H_2O$ (13.7 mL), stirred for 2 minutes at 0° C., and then warmed to room temperature where it continued to stir for 1 hour. The organic layer was isolated and the aqueous layer was extracted with $CH_2Cl_2$, (5×10 mL). Combined organics were dried over $Na_2SO_4$, filtered, and concentrated under reduced pressure to yield 110 as an orange solid (19.6 mg, >95% yield) which can be further purified by $C_{18}$ reverse phase column chromatography, with an AcCN/$H_2O$ (0.05% trifluoroacetic acid additive) gradient from 10%-30% acetonitrile over 20 column volumes. MP=106-110° C. IR (thin film, KBr) 3240 (br), 2918 (w), 2852 (w), 1700 (s), 1536 (s), 1446 (w), 1283 (m), 1203 (s), 1134 (m), 1031 (w), 893 (w), 785 (w) $cm^{-1}$. $^1H$ NMR (400 MHz, $CDCl_3$ δ 7.44 (s, 1H), 7.36 (s, 1H), 2.55 (s, 3H), 2.43 (s, 3H). $^{13}C$ NMR (100 MHz, $CDCl_3$) δ 204.08, 168.56, 159.03, 157.48, 141.72, 137.77, 125.04, 118.06, 30.92, 24.80. HRMS (ESI+) m/z calc'd for $C_{10}H_{10}O_4H^+$: 195.06519. Found: 195.06531.

111.

A solution of BC13 (1.0 M in $CH_2Cl_2$) (503 μL, 0.503 mmol) was diluted with $CH_2Cl_2$ (5.2 mL) and cooled to 0° C. In a separate round bottom flask, BC111 (19.4 mg, 0.072 mmol) was dissolved in $CH_2Cl_2$ (5.2 mL), was cooled to 0° C. and was added to the BC13 solution. After 10 minutes of stirring at 0° C., the reaction mixture was quenched with $H_2O$ (10.3 mL), stirred for 2 minutes at 0° C., and then warmed to room temperature where it continued to stir for 1 hour. The organic layer was isolated and the aqueous layer was extracted with $CH_2Cl_2$, (5×10 mL). Combined organics were dried over $Na_2SO_4$, filtered, and concentrated under reduced pressure to yield 111:MT111 as a yellow solid (19.6 mg, >95% yielded) in a 1:1 ratio. To the mixture of (16.9 mg, 0.062 mmol) was added acetic acid (364 μl) and 33% HBr in acetic acid (425 μl), and reaction was left to stir at 90° C. for 3 hours. After 3 hours, reaction mixture was let to cool to room temperature. The reaction was quenched with 7 pH phosphate buffer, and diluted with $CH_2Cl_2$. The organic layer was washed several times with the phosphate buffer. The organic layer was dried over $Na_2SO_4$, and evaporated under reduced pressure to yield a brown solid 111 (9.5 mg, 60% yield). Decomposed at temperatures from 45-50° C. IR (thin film, KBr) 3279 (br), 2918 (w), 2849 (w), 1674 (s), 1595 (w), 1536 (m), 1448 (m), 1284 (m), 1231 (s), 1084 (m), 829 (w), 725 (w), 688 (w) $cm^{-1}$. $^1H$ NMR (400 MHz, $CDCl_3$) δ 7.81 (d, J=7.7 Hz, 2H), 7.64 (t, J=7.3 Hz, 1H), 7.52 (s, 1H), 7.49 (dd, J=7.7, 7.7 Hz, 2H), 7.32 (s, 1H), 2.32 (s, 3H). $^{13}C$ NMR (101 MHz, $CDCl_3$) δ 197.09, 168.38, 158.69, 156.94, 139.71, 138.08, 135.58, 134.36, 130.10, 129.03, 124.31, 118.83, 24.48. HRMS (ESI+) m/z calc'd for $C_{15}H_{12}O_4H^+$: 257.0808. Found: 257.0806.

112.

A solution of BCl3 (1.0 M in $CH_2Cl_2$) (728 μL, 0.728 mmol) was diluted with $CH_2Cl_2$ (7.4 mL) and cooled to 0° C. In a separate round bottom flask, BC112 (29.8 mg, 0.104 mmol) was dissolved in $CH_2Cl_2$ (7.4 mL), was cooled to 0° C. and was added to the BCl3 solution. After 10 minutes of stirring at 0° C., the reaction mixture was quenched with $H_2O$ (15 mL), stirred for 2 minutes at 0° C., and then warmed to room temperature where it continued to stir for 1 hour. The organic layer was isolated and the aqueous layer was extracted with $CH_2Cl_2$, (5×10 mL). Combined organics were dried over $Na_2SO_4$, filtered, and concentrated under reduced pressure to yield 112:MT112 as a yellow solid (23.3 mg, 81%) in a 1:1 mixture. To the mixture was added acetic acid (473 μl) and 33% HBr in acetic acid (552 μl), and reaction was left to stir at 90° C. for 3 hours. After 3 hours, reaction mixture was let to cool to room temperature. The reaction was quenched with 7 pH phosphate buffer, and diluted with DCM. The organic layer was washed several times with the phosphate buffer. The organic layer was dried over $Na_2SO_4$, and evaporated under reduced pressure to yield a brown solid 112 (17.8 mg, 80% yield). Decomposes at temperatures between 194-200° C. IR (thin film, KBr) 3229 (br), 2917 (w), 1595 (m), 1518 (s), 1344 (s), 1279 (m), 1260 (m), 1194 (m), 1092 (m), 855 (w), 702 (w) cm$^{-1}$. $^1$H NMR (400 MHz, $CDCl_3$) δ 8.32 (d, J=8.3 Hz, 2H), 7.57 (s, 1H), 7.44 (d, J=8.3 Hz, 2H), 7.38 (s, 1H), 2.24 (s, 3H). $^{13}$C NMR (100 MHz, $CDCl_3$) δ 167.65, 158.14, 156.43, 149.96, 147.38, 140.57, 138.29, 129.53, 124.08, 123.99, 122.79, 26.25. HRMS (ESI+) m/z calc'd for $C_{14}H_{11}NO_5H^+$: 274.0710. Found: 274.0705.

113.

To a solution of BC113 (13.7 mg, 0.0566 mmol) in $CHCl_3$ (566 μL) was added triflic acid (20.0 μL, 0.226 mmol). The reaction was allowed to stir for 30 minutes at rt before quenching with sodium acetate (46.43 mg, 0.566 mmol). To this mixture was added 1.87 mL 33% HBr/AcOH solution (twice the solvent volume). The reaction was heated to 130° C. for 4 hours before being quenched to pH 5 with 10 mL of pH 7 phosphate buffer. The organic layer was isolated and the aqueous layer was extracted with $CH_2Cl_2$ (5×10 mL). Combined organics were dried over $Na_2SO_4$, filtered, and concentrated under reduced pressure to yield 113 as a black oil (13.0 mg, 95% yield). IR (thin film, KBr) 3727 (w), 3702 (w), 3625 (w), 3599 (w), 3247 (br), 2924 (w), 2854 (w), 1527 (m), 1392 (m), 1279 (m), 1129 (w), 768 (w), 669 (w) cm$^{-1}$. $^1$H NMR (200 MHz, $CDCl_3$) δ 7.58 (s, 1H), 7.50 (s, 1H), 7.48-7.33 (m, 3H), 7.23 (dd, J=7.6, 1.8 Hz, 2H), 2.26 (s, 3H). $^{13}$C NMR (200 MHz, $CDCl_3$) δ 167.11, 157.65, 156.39, 143.74, 143.60, 138.93, 128.59, 128.25, 127.68, 124.27, 124.11, 26.42. HRMS (ESI+) m/z calc'd for $C_{14}H_{13}O_3$ (M+H): 299.0859. Found: 299.0865.

MT114.

To a solution of BC114 (17.6 mg, 0.0548 mmol) in $CH_2Cl_2$ (548 μL) was added triflic acid (19.4 μL, 0.219 mmol). The reaction was allowed to stir for 30 minutes at rt before quenching to pH 6 with pH 7 phosphate buffer and extracting with $CH_2Cl_2$ (5×10 mL). Combined organics were dried over $Na_2SO_4$, filtered, and concentrated under reduced pressure to afford MT114. MP=110-115° C. FTIR (KBr, thin film) 815.4 (w), 1211.4 (s), 1264.2 (s), 1713.9 (w), 2939.4 (w), 3259.2 (b) cm$^{-1}$. $^1$H NMR (400 MHz, CDCl3) δ 7.56 (d, J=8.3 Hz, 2H), 7.32 (s, 1H), 7.14 (s, 1H), 7.12 (d, J=8.3 Hz, 2H), 4.02 (s, 3H), 2.25 (s, 3H). $^{13}$C NMR (100 MHz, $CDCl_3$) δ 170.1, 158.8, 158.5, 142.7, 141.8, 135.1, 132.1, 130.4, 122.4, 122.2, 121.7, 56.7, 26.9. HRMS (ESI+): calc'd for $C_{15}H_{14}BrO_3$ (M+H): 321.0121; Found: 321.0128.

114.

To MT114 (12.5 mg) was added 550 μL 33% HBr/AcOH solution. The reaction was heated to reflux (120° C.) for 4 hours before being quenched to pH 5 with 10 mL of pH 7 phosphate buffer. The organic layer was isolated and the aqueous layer was extracted with $CH_2Cl_2$ (5×10 mL). Combined organics were dried over $Na_2SO_4$, filtered, and concentrated under reduced pressure to yield 114 as an orange/brown oil (10.3 mg, 86% yield). IR (thin film, KBr) 3248 (br), 1528 (m), 1487 (w), 1447 (w), 1388 (w), 1279 (w), 1208 (w), 1128 (w), 1092 (w), 1072 (w), 1012 (w), 814 (w), 669 (w) cm$^{-1}$. $^1$H NMR (200 MHz, $CDCl_3$) δ 7.58 (d, J 6.8 Hz, 2H), 7.43 (s, 1H), 7.26 (s, 1H), 7.12 (d, J 8.4 Hz, 2H), 2.23 (s, 3H). $^{13}$C NMR (100 MHz, $CDCl_3$) δ 167.61, 158.35, 156.55, 142.76, 142.52, 139.09, 132.21, 130.36, 124.54, 124.00, 122.43, 26.79. HRMS (ESI+) m/z calc'd for $C_{14}H_{12}BrO_3$ (M+H): 306.9964. Found: 306.9966.

MT115.

MT114 (28 mg, 0.087 mmol) was suspended in toluene (1.75 mL) and trimethyl(phenyl)tin (47.6 uL, 62 mg, 0.25 mmol) and tetrakis(triphenylphosphine)palladium(0) (10.02 mg, 0.0088 mmol) were added. The reaction was stirred vigorously for 4 days at reflux under argon. The solution was cooled to room temperature and the solvent was removed under pressure. The resulting residue was dissolved in $CH_2Cl_2$ (2 mL). The solution was then treated with aqueous NaOH (1 M, 25 mL), aqueous KF (saturated, 25 mL) and stirred vigorously for 30 minutes. The solution was acidified with aqueous HCl (2M, 25 mL) to a pH of 3. The solution was extracted with $CH_2Cl_2$ (3×25 mL), dried over $Na_2SO_4$, filtered and concentrated. Chromatography ($C_{18}$ column [10 g], 35% MeCN/$H_2O$ [0.05% TFA] to 100% MeCN [0.05% TFA] gradient over 20 column volumes) followed by concentration of product peaks yielded MT114 as a light yellow solid (15 mg, 55% yield). MP=174-180° C. FTIR (thin film, KBr) 1113 (s), 1132 (w), 1211 (s), 1554 (s), 1774 (w), 2933 (w), 2986 (w), 3018 (w), 3257 (s) cm-1; 1H NMR (400 MHz, $CDCl_3$) δ 7.70-7.21 (m, 11H), 4.04 (s, 3H), 2.35 (s, 3H). 13C NMR (100 MHz, $CDCl_3$) δ 169.79, 158.77, 158.24, 143.03, 142.66, 140.69, 140.57, 135.29, 129.06, 128.97, 127.77, 127.40, 127.26, 122.54, 122.18, 56.61, 26.89. HRMS (ESI+): calc'd for $C_{21}H_{18}O_3$ mass: 318.1251; Found: 318.1256.

115.

MT115 (16.5 mg, 0.052 mmol) was dissolved in 33% HBr/AcOH (0.52 mL). The reaction was heated to reflux for 3 h with constant stirring. The solution was cooled to room temperature, quenched with phosphate buffer (pH 7), extracted with $CH_2Cl_2$ (3×20 mL), dried over $Na_2SO_4$, filtered and concentrated to yield 115 as a light yellow solid (16.1 mg, >95% yield). MP=170-175° C. FTIR (KBr, thin film) 1525 (s), 2923 (w), 3246 (br), cm$^{-1}$; $^1$H NMR (400 MHz, $CDCl_3$) δ 7.79-7.20 (m, 11H), 2.32 (s, 3H). $^{13}$C NMR (100 MHz, $CDCl_3$) δ 167.35, 158.12, 156.87, 143.80, 142.84, 140.92, 140.70, 139.41, 129.24, 129.13, 127.96, 127.58, 127.44, 126.51, 124.79, 26.86. HRMS (ESI+): calc'd for $C_{20}H_{16}O_3$ mass: 304.1099; Found: 304.1105.

117.

A solution of $BCl_3$ (1.0M in $CH_2Cl_2$)(486 μL, 0.486 mmol) was diluted with $CH_2Cl_2$ (5 mL) and cooled to 0° C. In a separate round-bottom flask, BC117 was dissolved in $CH_2Cl_2$ (5 mL), was cooled to 0° C., and was added to the BCl3 solution. After 10 min at 0° C., reaction was quenched with $H_2O$ (10 mL), stirred for 2 minutes at 0° C., and then warmed to rt and stirred for 1 hr. The organic layer was isolated and the aqueous layer was extracted with $CH_2Cl_2$ (5×10 mL). Combined organics were dried over $Na_2SO_4$, filtered, and concentrated under reduced pressure to generate MT117 as a yellow solid (13.4 mg, 77% yield). MP=64-70° C. IR (thin film, KBr) 3381 (w), 2917 (w), 2848 (w), 1727

(s), 1551 (w), 1454 (w), 1317 (m), 1223 (s), 1146 (m), 1037 (m), 876 (2), 791 (w) cm$^{-1}$. $^1$H NMR (400 MHz, CDCl$_3$) δ 6.95 (s, 1H), 4.40 (q, J=7.1 Hz, 2H), 3.97 (s, 3H), 2.4 (s, 3H), 1.39 (t, J=7.1 Hz, 3H)$^{13}$C NMR (100 MHz, CDCl$_3$) δ 6.95169.70, 168.91, 160.01, 158.30, 137.98, 131.45, 126.86, 120.88, 62.14, 56.87, 25.79, 18.32, 14.41. HRMS (ESI+): calc'd for C$_{13}$H$_{16}$O$_5$Na$^+$ mass: 275.08899; Found: 275.08788. MT117 was converted to 117 by demethylation with HBr/AcOH analogous to other reactions.

118.

To BC118 (46.4 mg, 0.134 mmol) in CH$_2$Cl$_2$ (1.5 mL) was added trifluoromethanesulfonic acid (47.3 μL, 0.536 mmol, 4 eq). The reaction was allowed to stir for 30 minutes, at which time it was quenched with sodium acetate (110 mg, 1.34 mmol, 10 eq), stirred for 20 min, and concentrated under reduced pressure to generate methoxytropolone MT118. The methoxytropolone was then dissolved in 25% HBr in acetic acid (2 mL), and heated to 90° C. for 4 hr. The reaction was cooled to room temperature, quenched with pH 7 phosphate buffer (10 mL), and diluted with CH$_2$Cl$_2$ (5 mL). The organic layer was washed with phosphate buffer (3×10 mL), dried over Na$_2$SO$_4$, filtered, and concentrated to yield 118 as a brown oil (26.2 mg, 59% yield). IR (thin film, KBr) 3262 (br), 3060 (w), 2961 (w), 1669 (s), 1601 (s), 1534 (s), 1398 (m), 1284 (s), 1232 (s), 1191 (s), 1083 (s), 906 (m), 859 (m), 750 (s), 696 (m) cm-1. $^1$H NMR (400 MHz, CDCl$_3$) δ 7.88 (d, J=8.2 Hz, 2H), 7.71 (d, J=8.2 Hz, 2H), 7.63 (d, J=7.4 Hz, 2H), 7.54 (s, 1H), 7.52-7.39 (m, 3H), 7.36 (s, 1H), 2.36 (s, 3H). $^{13}$C NMR (100 MHz, CDCl$_3$) δ 197.02, 168.70, 159.03, 157.33, 147.49, 140.15, 139.85, 138.42, 134.57, 131.05, 129.41, 128.96, 128.01, 127.70, 124.67, 119.18, 24.86. HRMS (ESI+) m/z calc'd for C$_{21}$H$_{17}$O$_4^+$: 333.1121. Found: 333.1124.

119—

To a solution of BC119 (70.5 mg, 0.22 mmol) in CDCl$_3$ (2.2 mL) was added trifouoromethanesulfonic acid (78 μL, 0.88 mmol). The reaction stirred for 30 min, and then was quenched with phosphate bufferer (pH=7, 2 mL). Organic Layers collected, and aqueous layer washed with CH$_2$Cl$_2$ (3×2 mL). Combined organics dried over MgSO4 and concentrated to generate MT119 (67 mg, >95%). 10 mg of MT119 was dissolved in 33% HBr in Acetic Acid (310 μL) and heated to 90° C. for 3 hours. The reaction was cooled to room temperature, quenched with phosphate buffer (pH=7, 10 mL), and extracted with CH$_2$Cl$_2$ (3×10 mL). Organic layers combined and dried over Na$_2$SO$_4$ and concentrated to generate 119 (1 mg, 12% yield)$^1$H NMR (200 MHz, CDCl$_3$) δ 7.86-6.91 (m, 7H), 2.25 (s, 3H).

120.

To a solution of bicycle BC120 (30.0 mg, 0.103 mmol) in CH$_2$Cl$_2$ (900 μL) was added triflic acid (37.0 μL, 0.413 mmol). The reaction was allowed to stir for 30 minutes at rt before quenching with sodium acetate (85 mg, 1.03 mmol). After stirring for an additional 15 minutes, the solution was concentrated under reduced pressure. To this mixture was added 900 μL AcOH and 1.1 mL 33% HBr/AcOH solution. The reaction was heated to 90° C. for 4 hours before being quenched with pH 7 phosphate buffer and washed 3× with buffer. Combined organics were allowed to stir with solid potassium carbonate (72 mg, 0.515 mmol) for 10 minutes before washing with an equivalent volume of water. Aqueous layer was acidified with HCl dropwise to pH 5 and extracted with CH$_2$Cl$_2$. Combined organics were dried over Na$_2$SO$_4$, filtered, and concentrated under reduced pressure to yield 120 as brown oil (23.3 mg, 82% yield). IR (thin film, KBr) 3256 (br), 2924 (s), 2852 (m), 1704 (w), 1538 (w), 1447 (w), 1397 (w), 1280 (s), 1156 (m), 1090 (w), 906 (w), 788 (w), 733 (w) cm$^{-1}$. $^1$H NMR (200 MHz, CDCl$_3$) δ 7.46 (s, 1H), 7.27 (s, 1H), 2.67 (d, J=6.7 Hz, 2H), 2.40 (s, 3H), 1.99 (m, 1H), 1.85-1.62 (m, 5H), 1.39-0.91 (m, 5H). $^{13}$C NMR (50 MHz, CDCl$_3$) δ 205.95, 167.92, 158.66, 157.26, 142.10, 137.27, 124.89, 117.91, 50.75, 33.49, 33.20, 26.10, 26.03, 24.22. HRMS (ESI+) m/z calc'd for C$_{16}$H$_{21}$O$_4$ (M+H): 277.1434. Found: 277.1441.

143.

To a solution of BC143 (30.0 mg, 0.127 mmol) in CH$_2$Cl$_2$ (86.7 μL) was added triflic acid (45.0 μL, 0.507 mmol). The reaction was allowed to stir for 30 minutes at rt. To this mixture was added 3.07 mL AcOH and 834 μL of 33% HBr/AcOH solution. The reaction was heated to 90° C. for 4 hours before being quenched with pH 7 phosphate buffer and washed 3× with buffer. Combined organics were dried over Na$_2$SO$_4$, filtered, and concentrated under reduced pressure to yield 143 as a brown oil (21.7 mg, 77% yield). IR (thin film, KBr) 3261 (br), 2971 (w), 2933 (w), 2873 (w), 1701 (m), 1538 (m), 1397 (w), 1282 (m), 1189 (w), 1147 (w), 1092 (w), 904 (w), 669 (w) cm$^{-1}$. $^1$H NMR (200 MHz, CDCl$_3$) δ 7.47 (s, 1H), 7.28 (s, 1H), 3.19-3.04 (m, 1H), 2.38 (s, 3H), 1.21 (d, J=6.9 Hz, 6H). $^{13}$C NMR (50 MHz, CDCl$_3$) δ 210.15, 168.03, 158.66, 157.14, 141.39, 137.70, 124.64, 117.96, 40.57, 24.50, 18.05. HRMS (ESI+) m/z calc'd for C$_{12}$H$_{15}$O$_4$ (M+H): 223.0965. Found: 223.0965.

144.

To a solution of BC144 (19.2 mg, 0.0694 mmol) in CH$_2$Cl$_2$ (694 μL) was added triflic acid (24.5 μL, 0.278 mmol). The reaction was allowed to stir for 30 minutes at rt before quenching with sodium acetate (56.9 mg, 0.693 mmol). After stirring for an additional 15 minutes, the solution was concentrated under reduced pressure. To the mixture was added 696 μL AcOH and 151 μL 33% HBr/AcOH solution. The reaction was heated to 90° C. for 4 hours before being quenched to pH 5 with 10 mL of pH 7 phosphate buffer. The organic layer was isolated and the aqueous layer was extracted with CH$_2$Cl$_2$ (5×10 mL). Combined organics were dried over Na$_2$SO$_4$, filtered, and concentrated under reduced pressure. Upon finding clean conversion to the methoxytropolone, the product was resubjected to the HBr/AcOH reflux conditions (847 μL 33% HBr/AcOH solution, 120° C.) for two hours to yield 144 as a black oil (16.5 mg, 90% yield). IR (thin film, KBr) 3066 (w), 2974 (w), 2935 (w), 2839 (w), 1711 (s), 1604 (m), 1490 (w), 1174 (w), 1131 (w), 1092 (w), 864 (w), 827 (w) cm$^{-1}$. $^1$H NMR (200 MHz, CDCl$_3$) δ 7.56 (s, 1H), 7.43 (s, 1H), 7.42 (d, J=8.3 Hz, 2H), 7.18 (d, J=8.4 Hz, 2H), 2.24 (s, 3H). $^{13}$C NMR (100 MHz, CDCl$_3$) δ 167.62, 158.11, 156.78, 142.55, 139.09, 134.04, 130.14, 129.31, 124.55, 124.04, 29.99, 26.83. HRMS (ESI+) m/z calc'd for C$_{14}$H$_{12}$C$_{1}$O$_3$ (M+H): 263.0469. Found: 263.0474.

145.

To a solution of BC145 (27.3 mg, 0.0880 mmol) in CH$_2$Cl$_2$ (880 μL) was added triflic acid (31.1 μL, 0.352 mmol). The reaction was allowed to stir for 30 minutes at rt before quenching to pH 7 with pH 7 phosphate buffer and extracting with CH$_2$Cl$_2$ (5×10 mL). Combined organics were dried over Na$_2$SO$_4$, filtered, and concentrated under reduced pressure. To the isolated methoxytropolone (10.5 mg) was added 461 μL 33% HBr/AcOH solution. The reaction was heated to reflux (120° C.) for 7 hours before being quenched to pH 5 with 10 mL of pH 7 phosphate buffer. The organic layer was isolated and the aqueous layer was extracted with CH$_2$Cl$_2$ (5×10 mL). Combined organics were dried over Na$_2$SO$_4$, filtered, and concentrated under reduced pressure to yield 145 as a brown oil (6.3 mg, 63% yield). IR (thin film, KBr) 3247 (br), 1617 (w), 1530 (m), 1392 (w), 1324 (s), 1281 (w), 1166 (w), 1126 (m), 1068 (m), 1017 (w), 822 (w) cm$^{-1}$. $^1$H NMR (200 MHz, CDCl$_3$) δ 7.72 (d, J=8.5 Hz, 2H), 7.58 (s, 1H), 7.41 (s, 1H), 7.38 (d, J=8.5 Hz, 2H), 2.24 (s, 3H). $^{13}$C NMR (100 MHz, CDCl$_3$) δ 167.82, 158.28, 156.75, 147.43, 142.07, 138.91, 130.41 (q, J=32.7 Hz), 129.14, 126.04 (q, J=3.7 Hz), 124.47, 124.33 (q, J=270.0 Hz) 123.67, 26.66. HRMS (ESI+) m/z calc'd for $C_{15}H_{12}F_3O_3$ (M+H): 297.0733. Found: 297.0739.

146.

To a solution of BC146 (35.6 mg, 0.1218 mmol) in $CH_2Cl_2$ (1.22 mL) was added triflic acid (43.1 μL, 0.487 mmol). The reaction was allowed to stir for 30 minutes at rt before quenching to pH 7 with pH 7 phosphate buffer and extracting with $CH_2Cl_2$ (5×10 mL). Combined organics were dried over $Na_2SO_4$, filtered, and concentrated under reduced pressure. To the isolated methoxytropolone (18.2 mg) was added 800 μL 33% HBr/AcOH solution. The reaction was heated to reflux (120° C.) for 7 hours before being quenched to pH 6 with 10 mL of pH 7 phosphate buffer. The organic layer was isolated and the aqueous layer was extracted with $CH_2Cl_2$ (5×10 mL). Combined organics were dried over $Na_2SO_4$, filtered, and concentrated under reduced pressure to yield 146 as a brown oil (13.4 mg, 77% yield). IR (thin film, KBr) 3248 (br), 1526 (m), 1447 (w), 1383 (m), 1278 (w), 1239 (w), 1220 (w), 1086 (w), 783 (w), 730 (w) cm$^{-1}$. $^1$H NMR (200 MHz, CDCl$_3$) δ 7.92 (dd, J=7.8, 4.3 Hz, 2H), 7.63 (s, 1H), 7.52 (s, 1H), 7.61-7.27 (m, 5H), 2.08 (s, 3H). $^{13}$C NMR (100 MHz, CDCl$_3$) δ 167.87, 158.28, 156.75, 147.44, 142.07, 138.91, 130.97, 130.57, 130.25, 129.23, 129.10, 126.02, 125.68, 124.47, 123.67, 122.98, 29.97, 26.51. HRMS (ESI+) m/z calc'd for $C_{18}H_{15}O_3$ (M+H): 279.1016. Found: 279.1017.

147.

To a solution of BC147 (42.4 mg, 0.145 mmol) in $CH_2Cl_2$ (1.45 mL) was added triflic acid (51.3 μL, 0.580 mmol). The reaction was allowed to stir for 30 minutes at rt before quenching to pH 6 with pH 7 phosphate buffer and extracting with $CH_2Cl_2$ (5×10 mL). Combined organics were dried over $Na_2SO_4$, filtered, and concentrated under reduced pressure. To the isolated methoxytropolone (15.6 mg) was added 686 μL 33% HBr/AcOH solution. The reaction was heated to reflux (120° C.) for 8 hours before being quenched to pH 6 with 10 mL of pH 7 phosphate buffer. The organic layer was isolated and the aqueous layer was extracted with $CH_2Cl_2$ (5×10 mL). Combined organics were dried over $Na_2SO_4$, filtered, and concentrated under reduced pressure to yield 147 as a brown oil (12.5 mg, 85% yield). IR (thin film, KBr) 3248 (br), 1526 (w), 1446 (w), 1392 (w), 1284 (w), 1231 (w), 1205 (w), 1122 (w), 1092 (w), 907 (w), 858 (w) 795 (w), 730 (w) cm$^{-1}$. $^1$H NMR (200 MHz, CDCl$_3$) δ 7.89 (m, 3H), 7.71 (s, 1H), 7.61 (s, 1H), 7.59 (s, 1H), 7.55 (dd, J=2.9 Hz, 1H), 7.55 (d, J=9.5 Hz, 1H), 7.36 (dd, J=8.4, 1.6 Hz, 1H), 2.29 (s, 3H). $^{13}$C NMR (100 MHz, CDCl$_3$) δ 167.62, 158.13, 156.79, 143.95, 141.39, 139.43, 133.58, 132.87, 128.64, 128.40, 128.14, 127.52, 127.06, 126.87, 126.76, 124.59, 53.75, 26.82. HRMS (ESI+) m/z calc'd for $C_{18}H_{15}O_3$ (M+H): 279.1016. Found: 279.1022.

173.

To a solution of BC173 (30.0 mg, 0.103 mmol) in $CH_2Cl_2$ (900 μL) was added triflic acid (37.0 μL, 0.413 mmol). The reaction was allowed to stir for 30 minutes at rt before quenching with sodium acetate (85 mg, 1.03 mmol). After stirring for an additional 15 minutes, the solution was concentrated under reduced pressure. To this mixture was added 900 μL AcOH and 1.1 mL 33% HBr/AcOH solution. The reaction was heated to 90° C. for 4 hours before being quenched with pH 7 phosphate buffer and washed 3× with buffer. Combined organics were allowed to stir with solid potassium carbonate (72 mg, 0.515 mmol) for 10 minutes before washing with an equivalent volume of water. Aqueous layer was acidified with HCl dropwise to pH 5 and extracted with $CH_2Cl_2$. Combined organics were dried over $Na_2SO_4$, filtered, and concentrated under reduced pressure to yield 173 as brown oil (23.3 mg, 82% yield). IR (thin film, KBr) 3256 (br), 2924 (s), 2852 (m), 1704 (w), 1538 (w), 1447 (w), 1397 (w), 1280 (s), 1156 (m), 1090 (w), 906 (w), 788 (w), 733 (w) cm$^{-1}$. $^1$H NMR (200 MHz, CDCl$_3$) δ 7.46 (s, 1H), 7.27 (s, 1H), 2.67 (d, J=6.7 Hz, 2H), 2.40 (s, 3H), 1.99 (m, 1H), 1.85-1.62 (m, 5H), 1.39-0.91 (m, 5H). $^{13}$C NMR (50 MHz, CDCl$_3$) δ 205.95, 167.92, 158.66, 157.26, 142.10, 137.27, 124.89, 117.91, 50.75, 33.49, 33.20, 26.10, 26.03, 24.22. HRMS (ESI+) m/z calc'd for $C_{16}H_{21}O_4$ (M+H): 277.1434. Found: 277.1441.

196.

To a solution of BC196 (6.0 mg, 0.0236 mmol) in $CH_2Cl_2$ (1.69 mL) was added a 1M solution of $BCl_3$ in $CH_2Cl_2$ (165.2 μL, 0.1652 mmol). The reaction was allowed to stir at room temperature for 10 minutes before being quenched to pH 7 with pH 7 phosphate buffer. The organic layer was isolated and the aqueous layer was extracted with $CH_2Cl_2$ (5×10 mL). Combined organics were dried over $Na_2SO_4$, filtered, and concentrated under reduced pressure to yield a red oil (5.8 mg, 97% yield). Of this material, 3.3 mg (0.0130 mmol) was treated to 145 μL of 33% HBr/AcOH. The reaction was heated to reflux at 120° C. for 35 minutes before being quenched to pH 4 with pH 7 phosphate buffer. The organic layer was isolated and the aqueous later was extracted with $CH_2Cl_2$ (5×10 mL). Combined organics were dried over $Na_2SO_4$, filtered, and concentrated under reduced pressure to yield 196 as a red/brown oil (1.6 mg, 55%; 53% overall yield). $^1$H NMR (200 MHz, CD$_3$OD) δ 7.00 (s, 1H), 3.91 (s, 3H), 2.32 (s, 3H). $^{13}$C NMR (100 MHz, CDCl$_3$) δ 167.19, 157.30, 154.48, 153.35, 152.28, 136.81, 125.03, 120.75, 52.08, 24.69.

4. Activity Against HBV

TABLE 4

Activity in HBV Assay

| Compound Number | Compound | $EC_{50}$ (μM) | $CC_{50}$ (μM) | Activity in qualitative HBV replication inhibition assay |
|---|---|---|---|---|
| 106 | 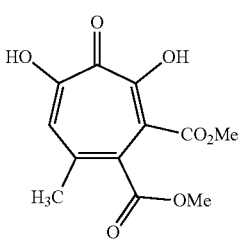 [SMILES: COC(=O)c1c(C)cc(O)c(=O)c(O)c1C(=O)OC] | 2.7 | 38 | ** |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 107 | (structure: tropone with HO, OH, CO$_2$Me, C(O)OMe, CH$_2$Cl substituents) | ND | 71 | ** |
| 108 | (structure: tropone with HO, OH, CO$_2$Me, C(O)OMe, CH$_2$OMe substituents) | ND | 81 | ** |
| 109 | (structure: tropone with HO, OH, H$_3$C, C(O)OEt substituents) | ND | 93 | ** |
| 110 | (structure: tropone with HO, OH, H$_3$C, C(O)CH$_3$ substituents) | 0.34 | 32 | ** |
| 111 | (structure: tropone with HO, OH, H$_3$C, C(O)phenyl substituents) | ND | 31 | ** |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 112 | (cycloheptatrienone with 2,7-diOH, 3-methyl, 4-(4-nitrophenyl)) | 2.5 | 79 | ** |
| 113 | (cycloheptatrienone with 2,7-diOH, 3-methyl, 4-phenyl) | 4.2 | 47 | ** |
| 120 | (cycloheptatrienone with 2,7-diOH, 3-methyl, 4-(cyclohexylcarbonyl)) | ND | 24 | * |
| 146 | (cycloheptatrienone with 2,7-diOH, 3-methyl, 4-(1-naphthyl)) | 2.3 | 12 | * |
| 196 | (cycloheptatrienone with 2,7-diOH, 3-OH, 4-methyl, 5-(methoxycarbonyl)) | 6.5 | 13 | ** |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 231 | | 10 | 16 | * |
| 232 | | 9.6 | 55 | * |
| 235 | | 5.2 | 30 | * |
| 143 | | 6.0 | >100 | ** |
| 172 | | 2.1 | >100 | ** |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 173 | | 6.7 | 22 | ** |
| 118 | | 6.0 | 21 | * |
| 119 | | 6.4 | 81 | * |
| 257 | | 8.3 | 32 | * |
| 258 | | 8.8 | 28 | * |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 259 | | 2.8 | 21 | * |
| 261 | | ND | >100 | ** |
| 262 | | ND | 96 | ** |
| 263 | | ND | ND | * |
| 264 | | ND | 28 | * |

TABLE 4-continued

Activity in HBV Assay

| Compound Number | Compound | EC$_{50}$ (μM) | CC$_{50}$ (μM) | Activity in qualitative HBV replication inhibition assay |
|---|---|---|---|---|
| 265 | (structure: 2,7-dihydroxy-4-(furan-2-yl)tropone) | ND | 40 | ** |
| 266 | (structure: 2,7-dihydroxy-4-(pyridin-4-yl)tropone) | ND | 32 | * |
| 267 | (structure: 2,7-dihydroxy-4-(quinolin-3-yl)tropone) | ND | 25 | ** |
| 269 | (structure: methoxy/OMe/methyl-substituted tropone with methyl ester) | ND | >100 | * |
| 270 | (structure: trihydroxy methyl-substituted tropone with ethyl ester) | ND | T | ** |

TABLE 4-continued

Activity in HBV Assay

| Compound Number | Compound | $EC_{50}$ (μM) | $CC_{50}$ (μM) | Activity in qualitative HBV replication inhibition assay |
|---|---|---|---|---|
| 271 | [structure] | ND | T | * |
| 272 | [structure] | ND | T | * |
| 274 | [structure] | ND | >100 | ** |
| 280 | [structure] | ND | 32 | ** |

** +DNA suppression <25% and −DNA suppression >60%
* +DNA suppression <50% of −DNA suppression
ND, not determined
T, visually toxic to hepatoma cells

3. Synergistic Activity of HBV RNAseH with Nucleoside Analog Drug

Figures 6A, 6B:
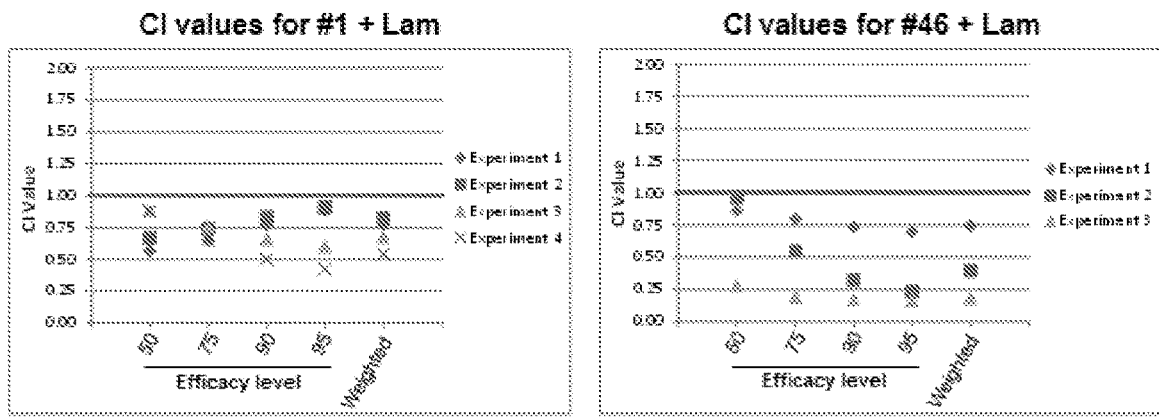
FIGS. 6A & 6B show the RNAseH inhibitors work synergistically with Lamivudine against HBV replication. Chou-Talaly combination indexes for compounds #1 (FIG. 6A) and #46 (FIG. 6B) together with Lamivudine. Additive interactions are shown with the red line, synergistic interactions below the line, and antagonistic interactions are above the line.

Current nucleos(t)ide analog therapy for HBV has converted hepatitis type B from an implacably progressing illness to a controllable disease. However, patients are only very rarely cured, in part due to the incomplete inhibition of HBV replication. The inventors hypothesized that the novel RNaseH inhibitors would work synergistically with the existing nucleos(t)ide analogs because the two classes of drugs target physically distinct active sites on the viral polymerase protein. Therefore, potential synergy between the RNAseH inhibitors and the nucleoside analog Lamivudine was analyzed using the Chou-Talalay method (Chou 2010). RNAseH inhibitors from two different chemical classes were employed, compound #1 [2-hydroxyisoquinoline-1,3(2H,4H)-dione], an HID, and #46 (β-thujaplicinol), an α-hydroxytropolone, were tested. Chou-Talaly analysis yields a combination index (CI). CI values<1.0 indicate synergy, CIs of approximately 1.0 indicate additive interactions, and CI values>1.0 indicate antagonism. CI values are calculated at various efficacy levels ($EC_{50}$, $EC_{75}$, $EC_{90}$, and $EC_{95}$), and a weighted CI value favoring higher efficacy levels is also generated. FIGS. 6A & 6B show the results of four experiments employing compound #1 and three with compound #46. All experiments revealed synergistic interactions between the RNAseH inhibitors and Lamivudine, and the weighted CI values were 0.70±0.1 for the HID compound #1 and 0.44±0.3 for the α-hydroxytropolone #46. Therefore, RNAseH inhibitors act strongly synergistically with an approved nucleos(t)ide analog drug against HBV. This demonstrates feasibility for employing RNAseH inhibitors in combination therapy with the nucleos(t)ide analogs during HBV treatment.

4. RNAseH Inhibitor Sensitivity is Insensitive to High Genetic Variation

Figures 7A, 7B:
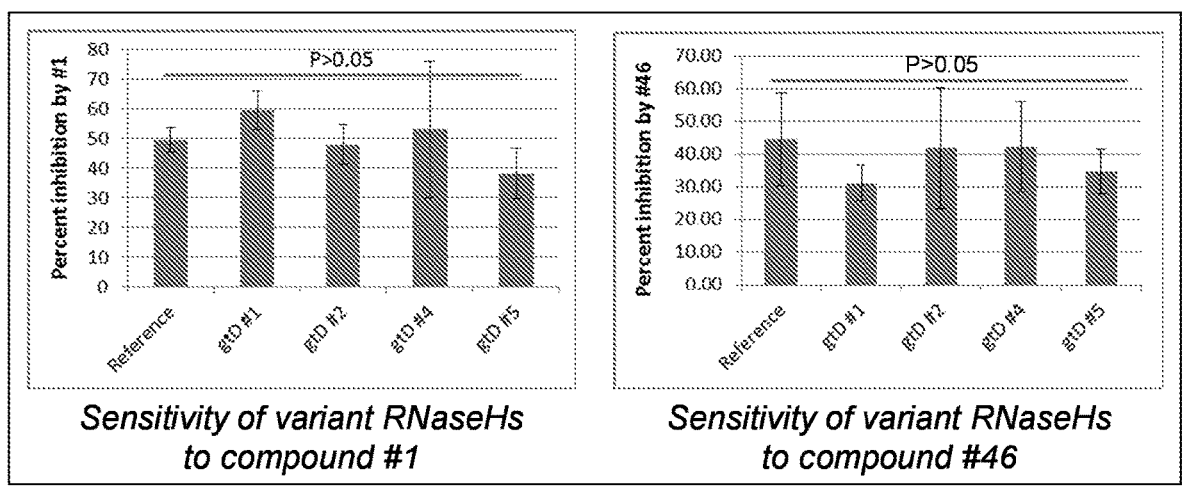
FIGS. 7A & 7B show that HBV's genetic variation is unlikely to present a barrier to RNAseH drug development. Four variant patient-derived RNAseH enzymes were expressed as recombinant enzymes, purified, and tested in an RNAseH assay with compounds #1 (FIG. 7A) and #46 (FIG. 7B) at their respective $IC_{50}$s.
Figure 8A:
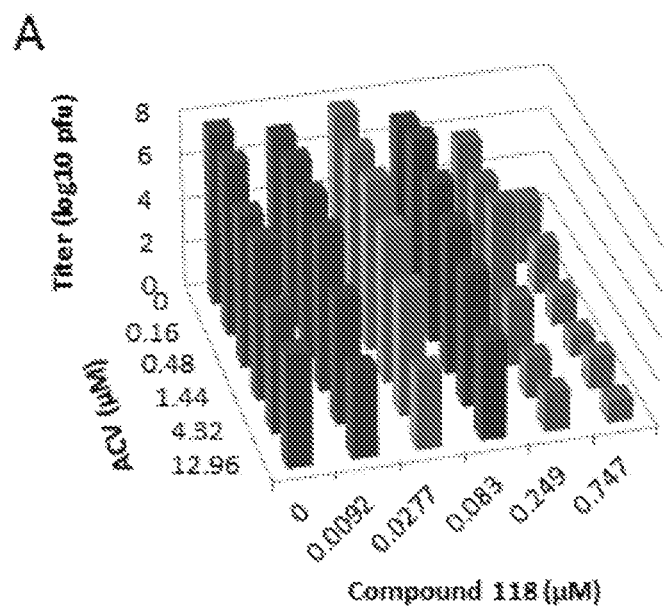
FIGS. 8A-8C show ACV and compound 118 synergistically inhibit HSV-2 replication and DNA accumulation. ACV and compound 118 were diluted in 3-fold steps and added alone or together in constant ratios to Vero cell monolayers infected with HSV-2 at an MOI of 0.1. After 24 h, the cultures were collected and divided into two aliquots. Shown are a representative volume plot of viral titers for combinations of ACV and/or compound 118 against HSV-2, as determined by a plaque assay (FIG. 8A), and isobolograms for qPCR for HSV-2 genomic DNA (FIG. 8B) and viral titer (FIG. 8C) data, as analyzed by the Chou-Talalay method.
Figure 8B:
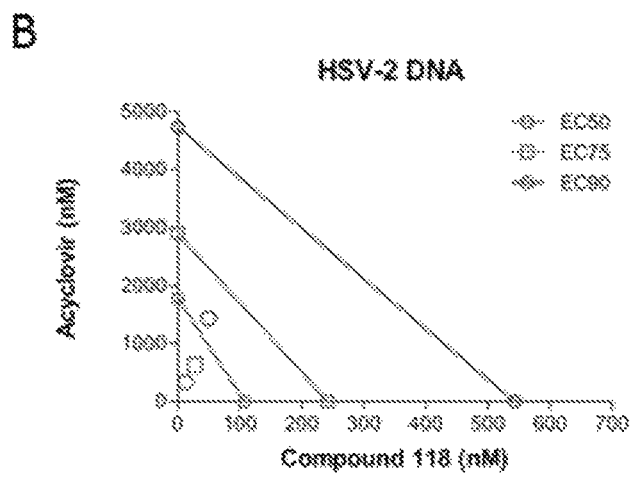
Figure 8C:
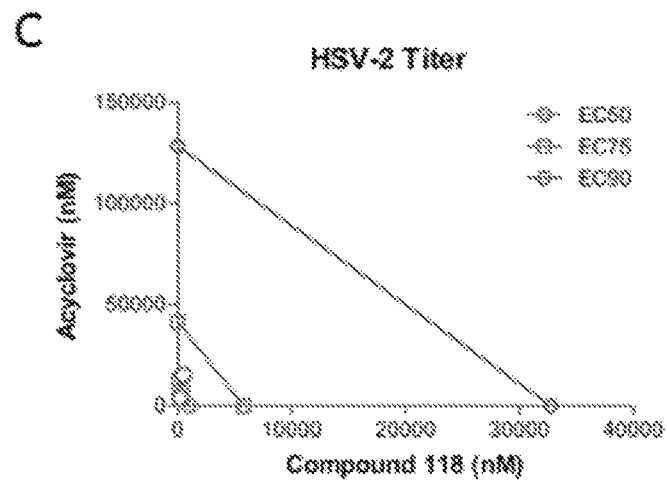

HBV has at least 8 genotypes differing in sequence by 8%. Genetic diversity in the RNAseH domain is about 6%, which is easily high enough to modulate viral sensitivity to RNAseH inhibitors. Therefore, the inventors tested the RNAseH inhibitors #1 [2-hydroxyisoquinoline-1,3(2H,4H)- dione], an HID, and #46 (β-thujaplicinol), an α-hydroxytropolone, for the ability to inhibit variant RNAseHs. Twelve purified, patient-derived RNAseH enzymes (4 from each genotypes B, C and D) were tested with the compounds at their respective $IC_{50}$ values in a biochemical RNAseH assay. FIGS. 7A & 7B demonstrate that the four genotype D enzymes each inhibited the HBV RNAseH by about 50% at the compounds $IC_{50}$ values as expected. Equivalent results were obtained for all 12 enzymes against compounds #1 and #46. Therefore, HBV's high genetic variation is unlikely to present a substantial barrier to drug development.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

F. REFERENCES

The following references, to the extent that they provide exemplary procedural or other details supplementary to those set forth herein, are specifically incorporated herein by reference:

Alba et al., *Genome Res.*, 11:43-54, 2001.
Andrei and Snoeck, *Curr Opin Infect Dis.* 26:551-560, 2013.
Aoki et al., *Antimicrob Agents Chemother.* 39:846-849, 1995.
Ariyoshi et al., *Cell* 78:1063-1072, 1994.
Arvin & Gilden, Varicella-Zoster *Virus*, 2015-2057, 2013.
Balzarini et al., *PLoS Pathog.* 9:e1003456, 2013.
Bernstein et al., *Antiviral Res* 92:386-388, 2011.
Billamboz et al., *J. Med. Chem.* 54:1812-1824, 2011.
Bogner et al., *J Virol.*, 72:2259-2264, 1998.
Bogner, *Rev Med Virol.*, 12:115-127, 2002.
Bokesch et al., *J. Nat. Prod.* 71, 1634-1636, 2008.
Bortner et al., *J Mol Biol.* 231:241-250, 1993.
Budihas et al., *Nucleic Acids Res.* 33, 1249-1256, 2005.
Cai, et al., *Antiviral Res.*, 108:48-55, 2014.
Chen et al., *J. Neurovirology* 8:204-210, 2002.
Choi et al., *Antiviral Res.* 55: 279-290, 2002.
Chono et al., *J. Antimicrob. Chemother.* 65:1733-1741, 2010.
Chou, et al., *Cancer Res.*, 70:440-446, 2010.
Chung et al., *J. Med. Chem.* 54, 4462-4473, 2011.
Chung et al., *Antimicrob. Agents Chemother.* 54, 3913-3921, 2010.
Clement et al., *Int J Cancer* 100:491-498, 2002.
Coen, *Antiviral Res*, 15:287-300, 1991.
Coen, *Viral DNA polymerases*, p. 495-523, 1996.
Cohen, *The New England journal of medicine* 369:255-263, 2013.
Damania & Cesarman, *Kaposi's Sarcoma-Associated Herpesvirus*, 2080-2128, 2013.
De et al., *Curr. Opin. Infect. Dis.*, 28:589-595, 2015.
Decaro et al., *The Veterinary clinics of North America. Small animal practice* 38:799-814, viii, 2008.
Derse et al., *J Biol Chem*, 257:10251-10260, 1982.
Di et al., *Bioorg. Med. Chem. Lett.* 20, 398-402, 2010.
Didierjean et al., *Antimicrob. Agents Chemother.* 49, 4884-4894, 2005.
Drew et al., *Clin Diagn Virol.* 1:179-185, 1993.
Drew et al., *J Infect Dis.* 179:1352-1355, 1999.
Drew et al., *Am J Transplant* 1:307-312, 2001.
Dolan et al., *J Virol* 72:2010-2021, 1998.
Duan et al., *J Infect Dis*, 200:1402-1414, 2009.
Duan, et al. *J Infect Dis*, 198:659-663, 2008.
Dyda et al., *Science* 266:1981-1986, 1994.
Eberhard et al., *Blood* 114:3064-3073, 2009.
Elion et al., *Proc Natl Acad Sci USA*, 74:5716-5720, 1977
Fenner et al., *Veterinary Virology*, 2 ed. Academic Press, 1993.
Field and Biron, *Clin Microbiol Rev*, 7:1-13, 1994.
Field and Vere Hodge, *Br Med Bull.* 106:213-249, 2013.
Fortier et al., *Veterinary J.* 186:148-156, 2010.
Frank et al., *Biol. Chem.* 379:1407-1412, 1998.
Frank et al., *Proc. Natl. Acad. Sci. USA* 95:12872-12877, 1998.
Freed et al., "HIVs and their replication," in: Knipe, D. M., Howley, P. M., Griffin, D. E., Lamb, R. A., Martin, M. A., Roizman, B., Straus, S. E. (Eds.), FIELDS VIROLOGY. Lippincott Williams & Wilkins, Philadelphia, pp. 2107-2185, 2007.
Fuji et al., *J. Med. Chem.* 52, 1380-1387, 2009.
Gao et al., *Virology* 249:460-470, 1998.
Gaskell et al., *Feline herpesvirus. Veterinary research* 38:337-354, 2007.
Gerelsaikhan et al., *J. Virol.* 70, 4269-4274, 1996.
Gilbert et al., *Canadian journal of public health=Revue canadienne de sante publique*, 2011.
Gilbert, et al., *Drug Resist Updat*, 5:88-114, 2002.
Gimeno, *Vaccine* 26 Suppl 3:$C_{31}$-41, 2008.
Goedken et al., *J. Biol. Chem.* 276, 7266-7271, 2001.
Hanauske-Abel et al., *PloS One* 8:e74414. doi: 10.1371, 2013.
Hanel et al., *Mycoses* 34 Suppl 1:91-93, 1991.
Hanson et al., *Viruses* 3(11): 2160-2191, 2011.
Higaki et al., *Cornea* 25(10 Suppl 1):564-67, 2006.
Himmel et al., *ACS Chem. Biol.* 1:702-712, 2006.
Himmel et al., *Structure* 17: 1625-1635, 2009.
Hirari, *Current Topics in Microbiology and Immunology: Marek's Disease*, 2001.
Hoffman et al., *Cytometry* 12:26-32, 1991.
Horowitz et al., *Journal of American college health: J of ACH* 59:69-74, 2011.
Hostomsky et al., *Nulceases*, vol. 2, 1993b.
Hostomsky et al., "Ribonuclease H," in: Linn, S. M., Lloyd, R. S., Roberts, R. J. (Eds.), Nulceases. Cold Spring Harbor Laboratory Press, Plainview, N.Y., pp. 341-376, 1993a.
Hostomsky et al., *Structure* 3:131-134, 1993c.
Hu et al., *Antiviral Res* 99:221-229, 2013.
Hwang and Bogner, *J Biol Chem.*, 277:6943-6948, 2002.
Imai et al., *J Infect Dis.* 189:611-615, 2004.
James et al., *Antiviral Res* 83:207-213, 2009.
Johnston et al., *Lancet* 379:641-647, 2012.
Kamali et al., *Sexually transmitted infections* 75:98-102, 1999.
Katayanagi et al., *Nature* 347: 306-309, 1990.
Keck et al., *J Biol. Chem.* 273, 34128-34133, 1998.
Kim et al., *In Vivo* 25:887-893, 2011.
Kimberlin, *Seminars in perinatology* 31:19-25, 2007.
Kirschberg et al., *J Med. Chem.* 52:5781-5784, 2009.
Klarmann et al., *AIDS Rev* 4: 183-194, 2002.
Klumpp et al., *Nucleic Acids Res.* 31, 6852-6859, 2004.
Klumpp and Mirzadegan, *Curr. Pharm. Des* 12:1909-1922, 2006.
Knipe and Spang *J Virol*, 43:314-324, 1982.
Ko et al., *PLoS One* 6:e27844. doi: 10.1371, 2011.

Komatsu et al., *Antiviral Res* 101:12-25, 2014.
Korom et al., *J Virol*, 87:5882-5894, 2013.
Kwun et al., *J Gen. Virol.* 82, 2235-2241, 2001.
Lai et al., *Structure* 8:897-904, 2000.
Levin et al., *Clin Infect Dis*, 39 Suppl 5:S248-257, 2004.
Li et al., *Mol. Biol. Evol.* 12:657-670, 1999.
Lima et al., *Methods Enzymol.* 341:430-440, 2001.
Linden et al., *Faseb J.*, 17:761-763, 2003.
Liu et al., *J Biol. Chem.* 281:18193-18200, 2006.
Longnecker et al., *Epstein-Barr Virus*, 1898-1959, 2013.
Looker et al., *Bull World Health Organ* 86:805-812, A, 2008.
Lu, et al., *Antimicrob. Agents Chemother.*, 59(2):1070-1079, 2015.
Luzuriaga & Sullivan, *N Eng J Med.* 362:1993-2000, 2010.
Manicklal et al., *Clinical Microbiology Rev.* 26: 86-102, 2013.
Marcellin et al., *N Engl. J. Med.* 359: 2442-2455, 2008.
Marchand, Tchesnokov, and Gotte. *J Biol Chem* 282: 3337-3346, 2007.
Marfori et al., *J Clin Virol.* 38:120-5, 2007.
Masaoka, et al., *Biochem.*, 55(5):809-819, 2016.
McDermott et al., *J Virol*, 51:747-753, 1984.
Mettenleiter et al., *Virus Res.* 143:222-234, 2009.
Mohni et al., *J. Virol.* 85:12241-12253, 2011.
Morfin and Thouvenot, *J Clin Virol.*, 26:29-37, 2003.
Morrison and Knipe, *Virology*, 220:402-413, 1996.
Nakagawa and Tayama, *Chem Biol Interact*, 116:45-60, 1998.
Nandi et al., *Animal health research reviews/Conference of Research Workers in Animal*, 2009.
Nauwynck et al., *Veterinary Res.* 38:229-241, 2007.
Nimonkar and Boehmer, *J Biol Chem.* 278:9678-9682, 2003.
Nowotny et al., *Cell* 121: 1005-1016, 2005.
Nowotny, *EMBO Rep.* 10:144-151, 2009.
Obasi et al., *J. Infectious Dis.* 179:16-24, 1999.
Parker et al., *EMBO J.* 23: 4727-4737, 2004.
Pellet & Roizman, Herpesviridae 1802-1822, 2013.
Pelosi et al., *Adv Exp Med Biol*, 312:151-158, 1992.
Pena et al., *J. Clin. Microbiol.* 48:150-153, 2010.
Popovic et al., *J. Thrombosis Thrombolysis* 33:160-172, 2012.
Potenza et al., *Protein Expr. Purif* 55: 93-99, 2007.
Prichard et al., *Antimicrob. Agents Chemother.* 55:4728-4734, 2011.
Quenelle et al., *Antivir Chem Chemother* 22:131-137, 2011.
Quinlan et al., *Cell* 36:857-868, 1984.
Reyes et al., *Arch Intern Med*, 163:76-80, 2003.
Roizman et al., *Herpes Simplex Viruses*, 1823-1897, 2013.
Rosen et al., *Int J Dermatol.*, 36:788-792, 1997.
Scheffczik et al., *Nucleic Acids Res.*, 30:1695-1703, 2002.
Schmit and Boivin, *J Infect Dis*, 180:487-490, 1999.
Scholz et al., *Nucleic Acids Res.*, 31:1426-1433, 2003.
Schumacher et al., *PLoS Pathog.* 8:e1002862, 2012.
Sehgal, *Br J Dermatol.* 95:83-88, 1976.
Selvarajan et al., *J. Virol.* 87:7140-7148, 2013.
Semenova et al., *Mol. Pharmacol.* 69:1454-1460, 2006.
Shaw-Reid et al., *J. Biol. Chem.* 278, 2777-2780, 2003.
Smith & Roberts, J. *ACH* 57:389-394, 2009.
Smith et al., *J. Virol.* 68, 5721-5729, 1994.
Smith, *Veterinary J.* 153:253-268, 1997.
Snydman, *Clin Infect Dis.* 47:883-884, 2008.
Song et al., *Science* 305: 1434-1437, 2004.
Su et al., *J. Virol.* 84:7625-7633, 2010.
Takada et al., *J. Nat. Prod.* 70, 1647-1649, 2007.
Tavis and Lomonosova, *Antiviral Res.*, 118:132-138, 2015.
Tavis et al., *PLoS Pathogens* 9:e1003125, 2013.
Tyring et al., *J. Infect. Dis.* 205:1100-1110, 2012.
Wald et al., *N Engl J Med.* 370:201-210, 2014.
Wang et al., *J. Virol.* 79:14079-14087, 2005.
Wang et al., *J Clin Virol*, 52:107-112, 2011.
Weizman & Weller, *Interactions between HSV-1 and the DNA damage response*, p. 257-268, 2011.
Weller & Coen, *Cold Spring Harbor Perspectives in Biology* 4:a013011, 2012.
Weller and Kuchta, *Expert Opin Ther Targets*, 17:1119-1132, 2013.
Wendeler et al., *ACS Chem. Biol.* 3, 635-644, 2008.
Williams et al., *Bioorg. Med. Chem. Lett.* 20:6754-6757, 2010.
Xu et al., *JAMA* 296:964-973, 2006.
Yamanishi et al., *Human Herpesviruses 6 and 7*, p. 2058-2079, 2013.
Yan et al., *MBio* 5:e01318-14, 2014.
Yang et al., *Science* 249: 1398-1405, 1990.
Yang and Steitz, *Structure*, 3, 131-134, 1995.
Yao et al., *Antimicrob Agents Chemother.* 58:2807-2815, 2014.
Zhou et al., *Int J Cancer* 127:2467-2477, 2010.
Zhou et al., *J Virol.* 88:11121-11129, 2014.
Zhu et al., *J. Virol.* 84:7459-7472, 2010.

What is claimed:

1. A compound of the formula:

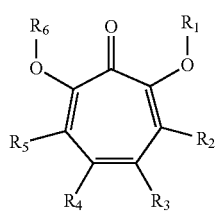

(I)

wherein:
- $R_1$ and $R_6$ are each independently selected from hydrogen, $acyl_{(C\leq 8)}$, or substituted $acyl_{(C\leq 8)}$;
- $R_2$ and $R_5$ are each independently selected from hydrogen, hydroxy, $alkyl_{(C\leq 8)}$, substituted $alkyl_{(C\leq 8)}$, $cycloalkyl_{(C\leq 12)}$, substituted $cycloalkyl_{(C\leq 12)}$, $aryl_{(C\leq 8)}$, substituted $aryl_{(C\leq 8)}$, $heteroaryl_{(C\leq 8)}$, substituted $heteroaryl_{(C\leq 8)}$, $alkoxy_{(C\leq 8)}$, substituted $alkoxy_{(C\leq 8)}$, $acyl_{(C\leq 8)}$, or substituted $acyl_{(C\leq 8)}$;
- $R_3$ is hydroxy, $cycloalkyl_{(C\leq 12)}$, substituted $cycloalkyl_{(C\leq 12)}$, $aryl_{(C7-18)}$, substituted $aryl_{(C7-18)}$, $heteroaryl_{(C\leq 12)}$, substituted $heteroaryl_{(C\leq 12)}$, or $-C(O)R_a$, wherein:
  - $R_a$ is $alkenyl_{(C\leq 11)}$, $aryl_{(C\leq 18)}$, $aralkyl_{(C\leq 11)}$, $heteroaryl_{(C\leq 18)}$, $aryloxy_{(C\leq 18)}$, or a substituted version of any of these groups; and
- $R_4$ is hydroxy, $alkyl_{(C\leq 12)}$, substituted $alkyl_{(C\leq 12)}$, $cycloalkyl_{(C\leq 12)}$, substituted $cycloalkyl_{(C\leq 12)}$, $aryl_{(C\leq 18)}$, substituted $aryl_{(C\leq 18)}$, $heteroaryl_{(C\leq 12)}$, substituted $heteroaryl_{(C\leq 12)}$, or $-C(O)R_a$, wherein:
  - $R_a$ is $alkyl_{(C\leq 18)}$, $cycloalkyl_{(C\leq 18)}$, $alkenyl_{(C\leq 11)}$, $aryl_{(C\leq 18)}$, $aralkyl_{(C\leq 11)}$, $heteroaryl_{(C\leq 18)}$, $aryloxy_{(C\leq 18)}$, $-alkanediyl_{(C\leq 6)}-cycloalkyl_{(C\leq 12)}$; or a substituted version of any of these groups; or
- $R_3$ and $R_4$ are taken together and are a group of the formula:

$-(CH_2)_mC(O)A(CH_2)_n-$, wherein:

- A is O or $NR_b$, wherein:
  - $R_b$ is hydrogen, $alkyl_{(C\leq 6)}$, or substituted $alkyl_{(C\leq 6)}$; and
- m and n are each independently selected from 0, 1, 2, or 3;

provided that the compound is not a compound of the following structures:

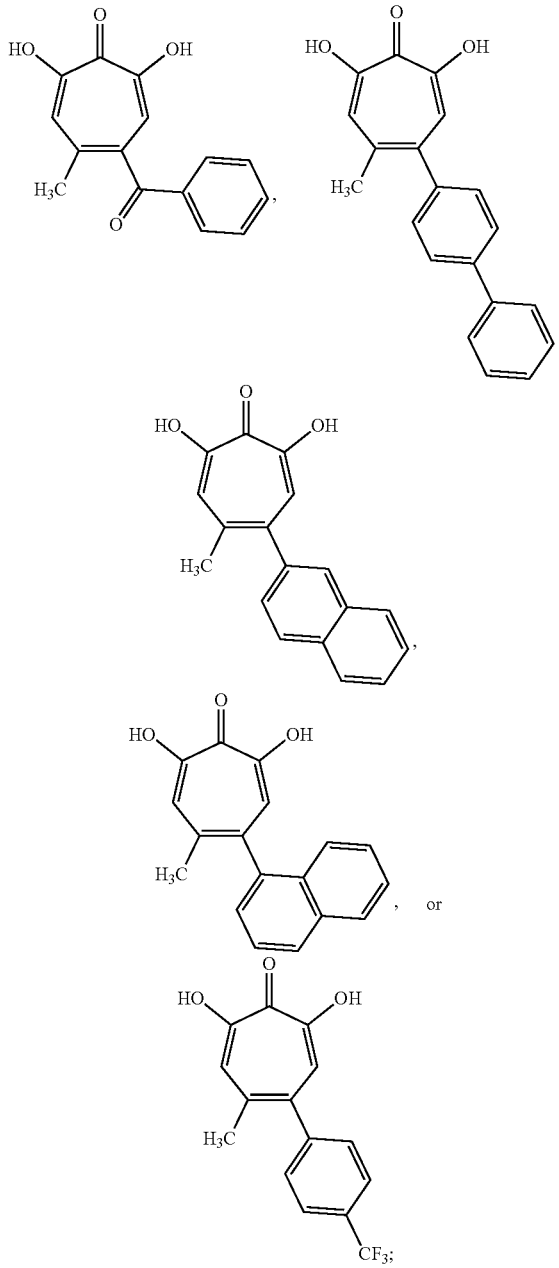

or a pharmaceutically acceptable salt or tautomer thereof.

2. The compound of claim 1 further defined as:

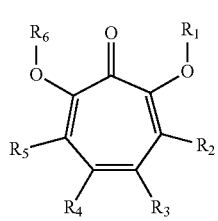

wherein:

$R_1$ and $R_6$ are each independently selected from hydrogen, acyl$_{(C \leq 8)}$, or substituted acyl$_{(C \leq 8)}$;

$R_2$ and $R_5$ are each independently selected from hydrogen, hydroxy, alkyl$_{(C \leq 8)}$, substituted alkyl$_{(C \leq 8)}$, cycloalkyl$_{(C \leq 12)}$, substituted cycloalkyl$_{(C \leq 12)}$, aryl$_{(C \leq 8)}$, substituted aryl$_{(C \leq 8)}$, heteroaryl$_{(C \leq 8)}$, substituted heteroaryl$_{(C \leq 8)}$, alkoxy$_{(C \leq 8)}$, substituted alkoxy$_{(C \leq 8)}$, acyl$_{(C \leq 8)}$, or substituted acyl$_{(C \leq 8)}$;

$R_3$ is hydroxy, cycloalkyl$_{(C \leq 12)}$, substituted cycloalkyl$_{(C \leq 12)}$, aryl$_{(C7-18)}$, substituted aryl$_{(C7-18)}$, heteroaryl$_{(C \leq 8)}$, substituted heteroaryl$_{(C \leq 8)}$, or —C(O)R$_a$, wherein:

$R_a$ is alkenyl$_{(C \leq 11)}$, aryl$_{(C \leq 18)}$, aralkyl$_{(C \leq 11)}$, heteroaryl$_{(C \leq 18)}$, aryloxy$_{(C \leq 18)}$, or a substituted version of any of these groups; and $R_4$ is hydroxy, alkyl$_{(C \leq 12)}$, substituted alkyl$_{(C \leq 12)}$, cycloalkyl$_{(C \leq 12)}$, substituted cycloalkyl$_{(C \leq 12)}$, aryl$_{(C \leq 18)}$, substituted aryl$_{(C \leq 18)}$, heteroaryl$_{(C \leq 8)}$, substituted heteroaryl$_{(C \leq 8)}$, or —C(O)R$_a$, wherein:

$R_a$ is alkyl$_{(C \leq 18)}$, cycloalkyl$_{(C \leq 18)}$, alkenyl$_{(C \leq 11)}$, aryl$_{(C \leq 18)}$, aralkyl$_{(C \leq 11)}$, heteroaryl$_{(C \leq 18)}$, aryloxy$_{(C \leq 18)}$, -alkanediyl$_{(C \leq 6)}$-cycloalkyl$_{(C \leq 12)}$; or a substituted version of any of these groups;

or a pharmaceutically acceptable salt or tautomer thereof.

3. The compound of claim 1 further defined as:

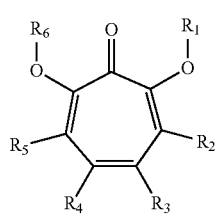

wherein:

$R_1$ and $R_6$ are each independently selected from hydrogen, acyl$_{(C \leq 8)}$, or substituted acyl$_{(C \leq 8)}$;

$R_2$ and $R_5$ are each independently selected from hydrogen, hydroxy, alkyl$_{(C \leq 8)}$, substituted alkyl$_{(C \leq 8)}$, cycloalkyl$_{(C \leq 12)}$, substituted cycloalkyl$_{(C \leq 12)}$, aryl$_{(C \leq 8)}$, substituted aryl$_{(C \leq 8)}$, heteroaryl$_{(C \leq 8)}$, substituted heteroaryl$_{(C \leq 8)}$, alkoxy$_{(C \leq 8)}$, substituted alkoxy$_{(C \leq 8)}$, acyl$_{(C \leq 8)}$, or substituted acyl$_{(C \leq 8)}$;

$R_3$ is hydroxy, cycloalkyl$_{(C \leq 12)}$, substituted cycloalkyl$_{(C \leq 12)}$, aryl$_{(C7-18)}$, substituted aryl$_{(C7-18)}$, heteroaryl$_{(C \leq 8)}$, substituted heteroaryl$_{(C \leq 8)}$, or —C(O)R$_a$, wherein:

$R_a$ is alkenyl$_{(C \leq 11)}$, aryl$_{(C \leq 18)}$, aralkyl$_{(C \leq 11)}$, heteroaryl$_{(C \leq 8)}$, aryloxy$_{(C \leq 12)}$, or a substituted version of any of these groups; and $R_4$ is hydroxy, alkyl$_{(C \leq 12)}$, substituted alkyl$_{(C \leq 12)}$, cycloalkyl$_{(C \leq 12)}$, substituted cycloalkyl$_{(C \leq 12)}$, aryl$_{(C \leq 12)}$, substituted aryl$_{(C \leq 12)}$, heteroaryl$_{(C \leq 8)}$, substituted heteroaryl$_{(C \leq 8)}$, or —C(O)R$_a$, wherein:

$R_a$ is alkenyl$_{(C \leq 11)}$, aryl$_{(C \leq 18)}$, aralkyl$_{(C \leq 11)}$, heteroaryl$_{(C \leq 8)}$, aryloxy$_{(C \leq 12)}$, or a substituted version of any of these groups;

or a pharmaceutically acceptable salt or tautomer thereof.

4. The compound of claim 1, wherein the compound is further defined as:

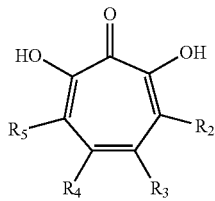

(II)

wherein: $R_2$, $R_3$, $R_4$, and $R_5$ are as defined above;

or a pharmaceutically acceptable salt or tautomer thereof.

5. The compound of claim 1, wherein $R_2$ is hydrogen, hydroxy, alkyl$_{(C \leq 8)}$, substituted alkyl$_{(C \leq 8)}$, acyl$_{(C \leq 8)}$, or substituted acyl$_{(C \leq 8)}$.

6. The compound of claim 1, wherein $R_5$ is hydrogen.

7. The compound of claim 1, wherein $R_4$ is alkyl$_{(C \leq 12)}$ or substituted alkyl$_{(C \leq 12)}$.

8. The compound of claim 1, wherein $R_3$ is aryl$_{(C7-18)}$, substituted aryl$_{(C7-18)}$, or —C(O)$R_a$, wherein: $R_a$ is aryl$_{(C \leq 18)}$, heteroaryl$_{(C \leq 18)}$, aryloxy$_{(C \leq 12)}$, or a substituted version of any of these groups.

9. The compound of claim 8, wherein $R_3$ is aryl$_{(C7-12)}$ or substituted aryl$_{(C7-12)}$.

10. The compound of claim 8, wherein $R_3$ is —C(O)$R_a$, wherein:

$R_a$ is aryl$_{(C \leq 18)}$, heteroaryl$_{(C \leq 18)}$, or a substituted version of either of these groups.

11. The compound of claim 1, wherein the compound is further defined as:

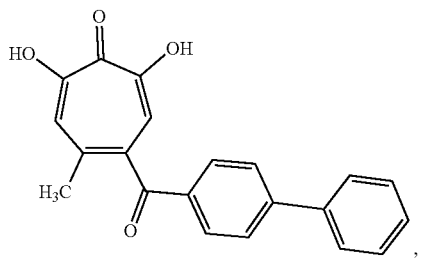 [SMILES: Cc1cc(O)c(=O)c(O)cc1C(=O)c1ccc(-c2ccccc2)cc1]

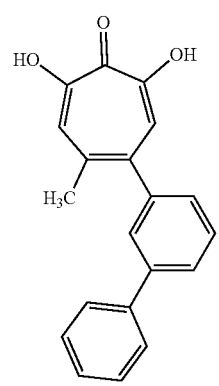

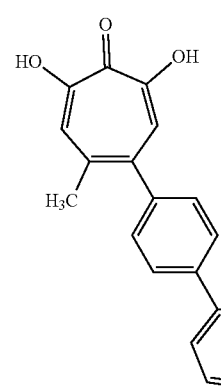

-continued

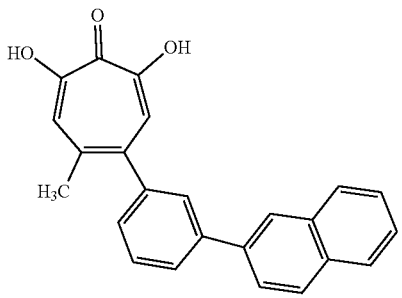

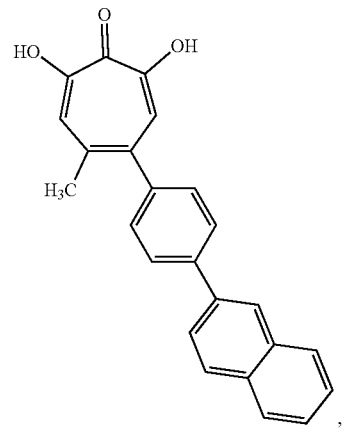

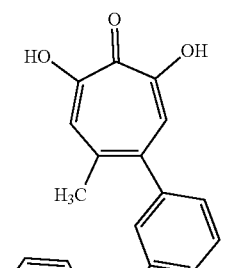

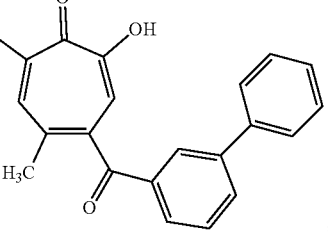

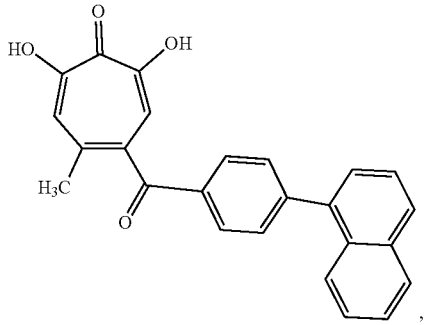

-continued

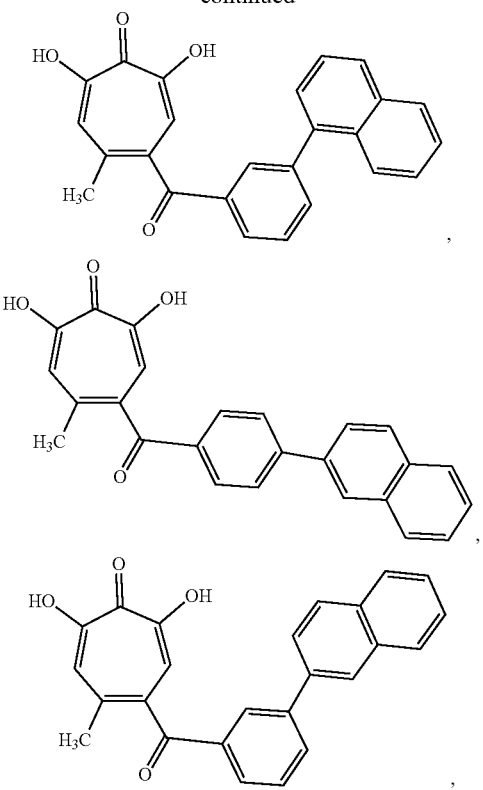

-continued

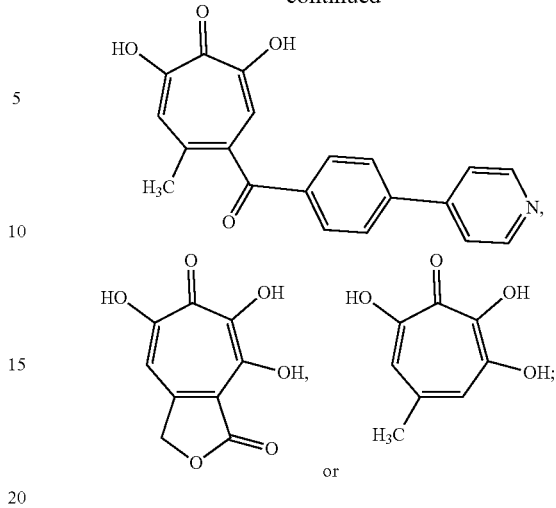

or a pharmaceutically acceptable salt or tautomer thereof.

12. A pharmaceutical composition comprising:
(a) a compound of claim 1; and
(b) a pharmaceutically acceptable carrier.

13. The pharmaceutical composition of claim 12, wherein the pharmaceutical composition is formulated for administration: intravenously, intra-arterially, orally, buccally, nasally, rectally, vaginally, ocularly, topically, intramuscularly, intradermally, cutaneously or subcutaneously.

14. The pharmaceutical composition of claim 13, wherein the pharmaceutical composition is formulated for topical administration to the cornea.

* * * * *

UNITED STATES PATENT AND TRADEMARK OFFICE
CERTIFICATE OF CORRECTION

PATENT NO. : 11,420,922 B2  
APPLICATION NO. : 15/735195  
DATED : August 23, 2022  
INVENTOR(S) : John Edwin Tavis, Lynda Anne Morrison and Ryan P. Murelli Page 1 of 1

It is certified that error appears in the above-identified patent and that said Letters Patent is hereby corrected as shown below:

In the Claims

Claim 14, Column 104, Line 15, delete " 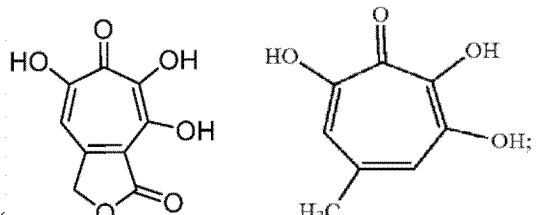 ;" and insert -- 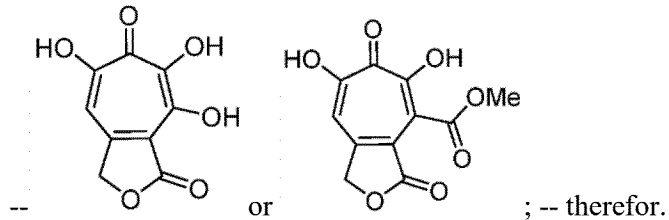 ; -- therefor.

Signed and Sealed this  
Eighth Day of November, 2022

Katherine Kelly Vidal  
*Director of the United States Patent and Trademark Office*

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial sequence
<220> FEATURE:
<223> OTHER INFORMATION: Synthetic primer

<400> SEQUENCE: 1
catgaacaag agatgattag gcagag                                            26

<210> SEQ ID NO 2
<211> LENGTH: 22
<212> TYPE: DNA
<213> ORGANISM: Artificial sequence
<220> FEATURE:
<223> OTHER INFORMATION: Synthetic primer

<400> SEQUENCE: 2
```

-continued

```
ggaggctgta ggcataaatt gg                                              22

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
ctgcgcacca gcaccatgca                                                 20

<210> SEQ ID NO 4
<211> LENGTH: 19
<212> TYPE: DNA
<213> ORGANISM: Artificial sequence
<220> FEATURE:
<223> OTHER INFORMATION: Synthetic primer

<400> SEQUENCE: 4
gcagatgaga aggcacaga                                                  19

<210> SEQ ID NO 5
<211> LENGTH: 17
<212> TYPE: DNA
<213> ORGANISM: Artificial sequence
<220> FEATURE:
<223> OTHER INFORMATION: Synthetic primer

<400> SEQUENCE: 5
cttctccgtc tgccgtt                                                    17

<210> SEQ ID NO 6
<211> LENGTH: 22
<212> TYPE: DNA
<213> ORGANISM: Artificial sequence
<220> FEATURE:
<223> OTHER INFORMATION: Synthetic primer

<400> SEQUENCE: 6
agtccgcgta aagagaggtg cg                                              22
```